US010557116B2

(12) United States Patent
Colter et al.

(10) Patent No.: US 10,557,116 B2
(45) Date of Patent: Feb. 11, 2020

(54) TREATMENT OF LUNG AND PULMONARY DISEASES AND DISORDERS

(75) Inventors: David C. Colter, Hamilton, NJ (US); Anthony J. Kihm, Princeton, NJ (US); Christine K. Ward, Gaithersburg, MD (US); Anna Gosiewska, Skillman, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 459 days.

(21) Appl. No.: 12/642,774

(22) Filed: Dec. 19, 2009

(65) Prior Publication Data
US 2010/0158877 A1 Jun. 24, 2010

Related U.S. Application Data

(60) Provisional application No. 61/139,425, filed on Dec. 19, 2008.

(51) Int. Cl.
| C12N 5/073 | (2010.01) |
| A61K 35/12 | (2015.01) |
| A61K 35/44 | (2015.01) |
| A61K 35/42 | (2015.01) |
| A61K 35/51 | (2015.01) |
| A61K 45/06 | (2006.01) |

(52) U.S. Cl.
CPC ............ *C12N 5/0605* (2013.01); *A61K 35/42* (2013.01); *A61K 35/51* (2013.01); *A61K 45/06* (2013.01); *A61K 35/12* (2013.01); *A61K 35/44* (2013.01)

(58) Field of Classification Search
CPC combination set(s) only.
See application file for complete search history.

(56) References Cited

U.S. PATENT DOCUMENTS

| 3,665,061 A | 5/1972 | Eberly, Jr. |
| 3,930,954 A | 1/1976 | Irie |
| 4,193,992 A | 3/1980 | Fontaine |
| 4,216,144 A | 8/1980 | Ashmead |
| 4,290,962 A | 9/1981 | Tachi et al. |
| 4,352,883 A | 10/1982 | Lim |
| 4,487,865 A | 12/1984 | Balazs et al. |
| 4,657,866 A | 4/1987 | Kumar |
| 4,882,162 A | 11/1989 | Ikada et al. |
| 4,925,667 A | 5/1990 | Fellows et al. |
| 4,963,489 A | 10/1990 | Naughton et al. |
| 5,004,681 A | 4/1991 | Boyse et al. |
| 5,192,553 A | 3/1993 | Boyse et al. |
| 5,248,608 A | 9/1993 | Van Dooren et al. |
| 5,286,632 A | 2/1994 | Jones |
| 5,320,962 A | 6/1994 | Stiles et al. |
| 5,342,761 A | 8/1994 | MacLeod |
| 5,437,994 A | 8/1995 | Emerson et al. |
| 5,443,950 A | 8/1995 | Naughton et al. |
| 5,456,835 A | 10/1995 | Castino et al. |
| 5,486,359 A | 1/1996 | Caplan et al. |
| 5,580,777 A | 12/1996 | Bernard et al. |
| 5,589,376 A | 12/1996 | Anderson et al. |
| 5,670,483 A | 9/1997 | Zhang et al. |
| 5,677,181 A | 10/1997 | Parish |
| 5,684,032 A | 11/1997 | Elliott et al. |
| 5,698,518 A | 12/1997 | Carson et al. |
| 5,707,643 A | 1/1998 | Ogura et al. |
| 5,736,516 A | 4/1998 | Louis |
| 5,811,094 A | 9/1998 | Caplan et al. |
| 5,827,735 A | 10/1998 | Young et al. |
| 5,834,308 A | 11/1998 | Peck et al. |
| 5,840,580 A | 11/1998 | Terstappen et al. |
| 5,842,477 A | 12/1998 | Naughton et al. |
| 5,843,780 A | 12/1998 | Thomson |
| 5,855,619 A | 1/1999 | Caplan et al. |
| 5,869,079 A | 2/1999 | Wong et al. |
| 5,902,598 A | 5/1999 | Chen et al. |
| 5,902,741 A | 5/1999 | Purchio et al. |
| 5,906,934 A | 5/1999 | Grande et al. |
| 5,919,702 A | 7/1999 | Purchio et al. |
| 5,928,214 A | 7/1999 | Rubinstein et al. |
| 5,942,225 A | 8/1999 | Bruder et al. |
| 5,955,343 A | 9/1999 | Holmes et al. |
| 5,962,325 A | 10/1999 | Naughton et al. |
| 5,994,094 A | 11/1999 | Hötten et al. |
| 6,001,647 A | 12/1999 | Peck et al. |
| 6,022,743 A | 2/2000 | Naughton et al. |
| 6,140,039 A | 10/2000 | Naughton et al. |
| 6,171,610 B1 | 1/2001 | Vacanti et al. |
| 6,200,606 B1 | 3/2001 | Peterson et al. |
| 6,200,806 B1 | 3/2001 | Thomson |
| 6,214,369 B1 | 4/2001 | Grande et al. |
| 6,221,904 B1 | 4/2001 | Agus et al. |
| 6,251,090 B1 | 6/2001 | Avery et al. |
| 6,261,841 B1 | 7/2001 | Cohen et al. |
| 6,291,240 B1 | 9/2001 | Mansbridge et al. |
| 6,323,188 B1 | 11/2001 | Weissman |
| 6,326,201 B1 | 12/2001 | Fung et al. |
| 6,331,313 B1 | 12/2001 | Wong et al. |
| 6,333,029 B1 | 12/2001 | Vyakarnam et al. |

(Continued)

FOREIGN PATENT DOCUMENTS

| CN | 1407088 | 2/2003 |
| JP | 2003-235549 | 8/2003 |

(Continued)

OTHER PUBLICATIONS

Tian et al. Influence of human bone marrow-derived mesenchymal stem cells on the lung of newborn rats damaged by hyperoxia. Zhonghua er ke za Zhi. Chinese Journal of Pediatrics. 2008, 46(1):4-8. Abstract only.*

(Continued)

*Primary Examiner* — Taeyoon Kim

(57) ABSTRACT

Compositions and methods of using cells derived from umbilical cord tissue to stimulate and support lung tissue angiogenesis, to improve blood flow to lung tissue, to regenerate, repair, and improve lung tissue damaged by lung disease, disorder and/or injury, and to protect lung tissue from damage caused by lung disease, disorder and/or injury in a patient.

32 Claims, 5 Drawing Sheets

Specification includes a Sequence Listing.

(56) References Cited

U.S. PATENT DOCUMENTS

| | | |
|---|---|---|
| 6,355,239 B1 | 3/2002 | Bruder et al. |
| 6,355,699 B1 | 3/2002 | Vyakarnam et al. |
| 6,372,494 B1 | 4/2002 | Naughton et al. |
| 6,375,972 B1 | 4/2002 | Guo et al. |
| 6,387,367 B1 | 5/2002 | Davis-Sproul et al. |
| 6,391,297 B1 | 5/2002 | Halvorsen |
| 6,429,013 B1 | 8/2002 | Halvorsen et al. |
| 6,436,704 B1 | 8/2002 | Roberts et al. |
| 6,444,205 B2 | 9/2002 | Dinsmore |
| 6,497,875 B1 | 12/2002 | Sorrell et al. |
| 6,511,511 B1 | 1/2003 | Slivka et al. |
| 6,528,245 B2 | 3/2003 | Sanchez-Ramos et al. |
| 6,534,084 B1 | 3/2003 | Vyakarnam et al. |
| 6,555,374 B1 | 4/2003 | Gimble et al. |
| 6,599,323 B2 | 7/2003 | Melican et al. |
| 6,610,535 B1 | 8/2003 | Lu et al. |
| 6,638,765 B1 | 10/2003 | Rosenberg |
| 6,673,606 B1 | 1/2004 | Tennekoon et al. |
| 6,680,198 B1 | 1/2004 | Snyder et al. |
| 6,686,198 B1 | 2/2004 | Melton et al. |
| 6,699,837 B2 | 3/2004 | Nakamura |
| 6,703,017 B1 | 3/2004 | Peck et al. |
| 6,916,655 B2 | 7/2005 | Yasumoto et al. |
| 7,413,734 B2 | 8/2008 | Mistry et al. |
| 7,510,873 B2 | 3/2009 | Mistry et al. |
| 7,524,489 B2 | 4/2009 | Messina et al. |
| 7,560,276 B2 | 7/2009 | Harmon et al. |
| 7,875,272 B2 | 1/2011 | Messina et al. |
| 7,875,273 B2 | 1/2011 | Messina et al. |
| 8,277,796 B2 | 10/2012 | Messina et al. |
| 8,318,483 B2 | 11/2012 | Mistry et al. |
| 8,658,152 B2 | 2/2014 | Messina et al. |
| 8,703,121 B2 | 4/2014 | Harris et al. |
| 8,815,587 B2 | 8/2014 | Harris et al. |
| 9,125,906 B2 | 9/2015 | Buensuceso et al. |
| 2001/0024824 A1 | 9/2001 | Moss et al. |
| 2001/0031256 A1 | 10/2001 | Edge |
| 2001/0046489 A1 | 11/2001 | Habener et al. |
| 2002/0022676 A1 | 2/2002 | He et al. |
| 2002/0028510 A1 | 3/2002 | Sanberg et al. |
| 2002/0062151 A1 | 5/2002 | Altman et al. |
| 2002/0064519 A1 | 5/2002 | Bruder et al. |
| 2002/0081725 A1 | 6/2002 | Tsang et al. |
| 2002/0098584 A1 | 7/2002 | Palmer et al. |
| 2002/0119565 A1 | 8/2002 | Clarke et al. |
| 2002/0123141 A1 | 9/2002 | Hariri |
| 2002/0150986 A1 | 10/2002 | Lau |
| 2002/0151056 A1 | 10/2002 | Sasai et al. |
| 2002/0160471 A1 | 10/2002 | Kisiday et al. |
| 2002/0160510 A1 | 10/2002 | Hariri |
| 2002/0164307 A1 | 11/2002 | Habener et al. |
| 2002/0164791 A1 | 11/2002 | Van Der Kooy et al. |
| 2002/0168763 A1 | 11/2002 | Yan et al. |
| 2002/0182728 A1 | 12/2002 | Ramiya et al. |
| 2002/0187550 A1 | 12/2002 | Dinsmore et al. |
| 2002/0192816 A1 | 12/2002 | Roberts et al. |
| 2003/0003574 A1 | 1/2003 | Toma et al. |
| 2003/0007954 A1 | 1/2003 | Naughton et al. |
| 2003/0022369 A1 | 1/2003 | Fillmore et al. |
| 2003/0031657 A1 | 2/2003 | Habener et al. |
| 2003/0032178 A1 | 2/2003 | Williams et al. |
| 2003/0032179 A1 | 2/2003 | Hariri |
| 2003/0032183 A1 | 2/2003 | Sheridan |
| 2003/0049837 A1 | 3/2003 | Weiss et al. |
| 2003/0059939 A1 | 3/2003 | Page et al. |
| 2003/0082155 A1 | 5/2003 | Habener et al. |
| 2003/0082160 A1 | 5/2003 | Yu et al. |
| 2003/0096409 A1 | 5/2003 | Yasumoto et al. |
| 2003/0104997 A1 | 6/2003 | Black et al. |
| 2003/0109036 A1 | 6/2003 | Wu |
| 2003/0113910 A1 | 6/2003 | Levanduski |
| 2003/0118566 A1 | 6/2003 | Neuman et al. |
| 2003/0124721 A1 | 7/2003 | Cheatham et al. |
| 2003/0138948 A1 | 7/2003 | Fisk et al. |
| 2003/0138951 A1 | 7/2003 | Yin |
| 2003/0148513 A1 | 8/2003 | Sugaya et al. |
| 2003/0161818 A1 | 8/2003 | Weiss et al. |
| 2003/0162290 A1 | 8/2003 | Inoue et al. |
| 2003/0170215 A1 | 9/2003 | Tsang et al. |
| 2003/0175963 A1 | 9/2003 | Rosenberg |
| 2003/0180269 A1 | 9/2003 | Hariri |
| 2003/0186439 A1 | 10/2003 | Nakauchi et al. |
| 2003/0199447 A1 | 10/2003 | Goldman et al. |
| 2003/0203483 A1 | 10/2003 | Seshi |
| 2003/0203484 A1 | 10/2003 | Black et al. |
| 2003/0207450 A1 | 11/2003 | Young et al. |
| 2003/0211087 A1 | 11/2003 | Goldman |
| 2003/0211603 A1 | 11/2003 | Earp et al. |
| 2003/0211605 A1 | 11/2003 | Lee et al. |
| 2003/0212024 A1 | 11/2003 | Keating et al. |
| 2003/0219894 A1 | 11/2003 | Seino et al. |
| 2003/0228295 A1 | 12/2003 | Svendsen |
| 2003/0235563 A1 | 12/2003 | Strom et al. |
| 2003/0235909 A1 | 12/2003 | Hariri et al. |
| 2004/0005704 A1 | 1/2004 | Csete et al. |
| 2004/0009593 A1 | 1/2004 | Keirstead et al. |
| 2004/0014206 A1 | 1/2004 | Robl et al. |
| 2004/0014210 A1 | 1/2004 | Jessell et al. |
| 2004/0014211 A1 | 1/2004 | Ogle et al. |
| 2004/0014662 A1 | 1/2004 | Lindquist et al. |
| 2004/0028660 A1 | 2/2004 | Hariri et al. |
| 2004/0029269 A1 | 2/2004 | Goldman et al. |
| 2004/0033597 A1 | 2/2004 | Toma et al. |
| 2004/0037818 A1 | 2/2004 | Brand et al. |
| 2004/0048372 A1 | 3/2004 | Hariri |
| 2004/0058412 A1 | 3/2004 | Ho et al. |
| 2004/0063202 A1 | 4/2004 | Petersen et al. |
| 2004/0072344 A1 | 4/2004 | Inoue et al. |
| 2004/0136967 A1 | 7/2004 | Weiss et al. |
| 2004/0224409 A1 | 11/2004 | Pradier et al. |
| 2004/0265283 A1 | 12/2004 | Morishita |
| 2005/0019865 A1 | 1/2005 | Kihm et al. |
| 2005/0032209 A1 | 2/2005 | Messina et al. |
| 2005/0037491 A1 | 2/2005 | Mistry et al. |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper et al. |
| 2005/0089513 A1 | 4/2005 | Sakuragawa et al. |
| 2005/0124003 A1 | 6/2005 | Atala et al. |
| 2005/0148074 A1 | 7/2005 | Davies et al. |
| 2005/0249731 A1 | 11/2005 | Aslan et al. |
| 2006/0128014 A1 | 6/2006 | Haggblad et al. |
| 2006/0147415 A1 | 7/2006 | Mousa et al. |
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009494 A1 | 1/2007 | Mistry et al. |
| 2007/0014771 A1 | 1/2007 | Mistry et al. |
| 2007/0036767 A1 | 2/2007 | Mistry et al. |
| 2007/0141700 A1 | 6/2007 | Harmon |
| 2007/0160588 A1 | 7/2007 | Kihm |
| 2007/0178073 A1 | 8/2007 | Chang et al. |
| 2007/0264269 A1 | 11/2007 | Harmon et al. |
| 2007/0275362 A1 | 11/2007 | Edinger et al. |
| 2008/0050349 A1 | 2/2008 | Stewart |
| 2008/0112939 A1 | 5/2008 | Colter et al. |
| 2008/0145934 A1 | 6/2008 | Harris et al. |
| 2008/0152624 A1* | 6/2008 | Paludan et al. ............ 424/93.7 |
| 2008/0159995 A1* | 7/2008 | Spiteri et al. ............. 424/93.7 |
| 2008/0166328 A1 | 7/2008 | Harmon et al. |
| 2008/0226595 A1 | 9/2008 | Edinger et al. |
| 2008/0274087 A1 | 11/2008 | Li et al. |

(56) References Cited

U.S. PATENT DOCUMENTS

| | | |
|---|---|---|
| 2008/0305148 A1 | 12/2008 | Fu |
| 2009/0092653 A1 | 4/2009 | Colter et al. |
| 2009/0166178 A1 | 7/2009 | Harmon et al. |
| 2009/0169597 A1 | 7/2009 | Brown et al. |
| 2010/0143312 A1 | 6/2010 | Hariri et al. |
| 2010/0158880 A1 | 6/2010 | Seyda et al. |
| 2010/0159025 A1 | 6/2010 | Kramer et al. |
| 2010/0159588 A1 | 6/2010 | Harmon et al. |
| 2010/0210013 A1 | 8/2010 | Mistry et al. |
| 2010/0215714 A1 | 8/2010 | Messina et al. |
| 2010/0247499 A1 | 9/2010 | Kihm et al. |
| 2010/0260843 A1 | 10/2010 | Messina et al. |
| 2010/0272803 A1 | 10/2010 | Mistry et al. |
| 2012/0014921 A1 | 1/2012 | Kramer et al. |
| 2012/0213743 A1 | 8/2012 | Buensuceso et al. |
| 2012/0315251 A1 | 12/2012 | Harris et al. |
| 2013/0022585 A1 | 1/2013 | Messina et al. |
| 2013/0216508 A1 | 8/2013 | Anversa et al. |
| 2014/0045263 A1 | 2/2014 | Mistry et al. |
| 2014/0154226 A1 | 6/2014 | Messina et al. |
| 2015/0064781 A1 | 3/2015 | Mistry et al. |

FOREIGN PATENT DOCUMENTS

| | | |
|---|---|---|
| JP | 2004-254682 | 9/2004 |
| WO | WO 90/11354 | 10/1990 |
| WO | WO 92/03917 | 3/1992 |
| WO | WO 93/04169 | 3/1993 |
| WO | WO 94/25584 | 11/1994 |
| WO | WO 95/17911 | 7/1995 |
| WO | WO 95/23216 | 8/1995 |
| WO | WO 96/01316 | 1/1996 |
| WO | WO 96/05309 | 2/1996 |
| WO | WO 98/17791 | 4/1998 |
| WO | WO 98/51317 | 11/1998 |
| WO | WO 99/03973 | 1/1999 |
| WO | WO 00/09666 | 2/2000 |
| WO | WO-00/053795 A1 | 9/2000 |
| WO | WO 00/073421 | 12/2000 |
| WO | WO 01/011011 | 2/2001 |
| WO | WO 01/019379 | 3/2001 |
| WO | WO 01/034775 | 5/2001 |
| WO | WO 02/046373 | 6/2002 |
| WO | WO 02/059278 | 8/2002 |
| WO | WO 02/062969 | 8/2002 |
| WO | WO 02/063962 | 8/2002 |
| WO | WO 02/064748 | 8/2002 |
| WO | WO 02/064755 | 8/2002 |
| WO | WO 02/086107 | 10/2002 |
| WO | WO 03/023020 | 3/2003 |
| WO | WO 03/025149 | 3/2003 |
| WO | WO 03/029443 | 4/2003 |
| WO | WO 03/029445 | 4/2003 |
| WO | WO 03/039489 | 5/2003 |
| WO | WO 03/042405 | 5/2003 |
| WO | WO 03/048336 | 6/2003 |
| WO | WO 03/055992 | 7/2003 |
| WO | WO 03/064601 | 8/2003 |
| WO | WO 03/066832 | 8/2003 |
| WO | WO 03/068937 | 8/2003 |
| WO | WO 03/070922 | 8/2003 |
| WO | WO 03/072728 | 9/2003 |
| WO | WO 03/080822 | 10/2003 |
| WO | WO 03/087333 | 10/2003 |
| WO | WO 03/087392 | 10/2003 |
| WO | WO 03/089619 | 10/2003 |
| WO | WO 03/100038 | 12/2003 |
| WO | WO 03/102134 | 12/2003 |
| WO | WO 03/102151 | 12/2003 |
| WO | WO 03/104442 | 12/2003 |
| WO | WO 04/011012 | 2/2004 |
| WO | WO 04/011621 | 2/2004 |
| WO | WO 04/016747 | 2/2004 |
| WO | WO 04/023100 | 3/2004 |
| WO | WO 04/072273 | 8/2004 |
| WO | WO-04/111207 A1 | 12/2004 |
| WO | WO 05/001076 | 1/2005 |
| WO | WO 05/001077 | 1/2005 |
| WO | WO 05/001078 | 1/2005 |
| WO | WO 05/001079 | 1/2005 |
| WO | WO 05/001080 | 1/2005 |
| WO | WO 05/003334 | 1/2005 |
| WO | WO 05/021738 | 3/2005 |
| WO | WO 05/038012 | 4/2005 |
| WO | WO 05/042703 | 5/2005 |
| WO | WO-05/085421 A2 | 9/2005 |
| WO | WO 06/055685 | 5/2006 |
| WO | WO 06/071773 | 7/2006 |
| WO | WO 06/071777 | 7/2006 |
| WO | WO 06/071778 | 7/2006 |
| WO | WO 06/071794 | 7/2006 |
| WO | WO 06/071802 | 7/2006 |
| WO | WO 06/083394 | 8/2006 |
| WO | WO 06/105152 | 10/2006 |
| WO | WO 06/117237 | 11/2006 |
| WO | WO-07/051625 A2 | 5/2007 |
| WO | WO 07/070870 | 6/2007 |
| WO | WO 07/073552 | 6/2007 |
| WO | WO 07/076522 | 7/2007 |
| WO | WO-07/079184 A2 | 7/2007 |
| WO | WO 07/108003 | 9/2007 |
| WO | WO-07/142651 A1 | 12/2007 |
| WO | WO-08/002250 A1 | 1/2008 |
| WO | WO-08/008229 A2 | 1/2008 |
| WO | WO 08/045498 | 4/2008 |
| WO | WO 08/060541 | 5/2008 |
| WO | WO 08/085221 | 7/2008 |
| WO | WO 09/046335 | 4/2009 |
| WO | WO 09/085860 | 7/2009 |
| WO | WO 10/071862 | 6/2010 |
| WO | WO 10/071863 | 6/2010 |
| WO | WO 10/071864 A1 | 6/2010 |
| WO | WO 10/080364 | 7/2010 |
| WO | WO 10/111663 | 9/2010 |
| WO | WO 10/071864 R | 6/2011 |
| WO | WO 07/124594 | 11/2011 |
| WO | WO-13/173376 A1 | 11/2013 |

OTHER PUBLICATIONS

Weiss and Troyer. Stem Cells in the Umbilical Cord. Stem Cell Rev. 2006 ; 2(2): 155-162.*

Yen et al. Stem cells in the lung parenchyma and prospects for lung injury therapy. European Journal of Clinical Investigation (2006) 36, 310-319.*

Warburton et al. Stem/Progenitor Cells in Lung Development, Injury Repair, and Regeneration. Proc Am Thorac Soc. Aug. 15, 2008; 5(6): 703-706.*

Sueblinvong et al. Derivation of Lung Epithelium from Human Cord Blood-derived Mesenchymal Stem Cells. Am J Respir Crit Care Med vol. 177. pp. 701-711, 2008 (Year: 2008).*

Bhandari et al. Hyperoxia causes angiopoietin 2-mediated acute lung injury and necrotic cell death. Nature Medicine. vol. 12, No. 11. p. 1286-1293 (Year: 2006).*

Cooper et al. Modulation of Monocyte Chemotactic Protein-1 Production by Hyperoxia: Importance of RNA Stability in Control of Cytokine Production. Am. J. Respir. Cell Mol. Biol. 18:521-525. (Year: 1998).*

Liu et al. Telomerase activity is required for bleomycin-induced pulmonary fibrosis in mice. J Clin Invest. Dec. 3, 2007; 117(12): 3800-3809. (Year: 2007).*

Abbas, A.K. et al., *Cellular and Molecular Immunology*, 5th Ed. (2003) Saunders, Philadelphia, p. 171.

Aboody, K.S. et al., "Neural Stem Cells Display Extensive Tropism for Pathology in Adult Brain: Evidence From Intracranial Gliomase," *PNAS*, 2000; 97(23):12846-12851.

Agbulut, O. et al., "Comparison of Human Skeletal Myoblasts and Bone Marrow-Derived CD133+ Progenitors for the Repair of Infarcted Myocardium," *Journal of the American College of Cardiology*, 2004; 44(2):458-463.

(56) References Cited

OTHER PUBLICATIONS

Age-Related Eye Disease Study Research. Group, "A Randomized, Placebo-Controlled, Clinical Trial of High-Dose Supplementation With Vitamins C and E, Beta Carotene, and Zinc for Age-Related Macular Degeneration and Vision Loss," AREDS Report No. 8, *Arch. Op.*
Aggarwal et al., "Human Mesenchymal Stem Cells Modulate Allogeneic Immune Cell Responses," *Blood*, 2005; 105(4):1815-1822.
Aldskogius, H. et al., "Strategies for Repair of the Deafferented Spinal Cord," *Brain Res. Rev.*, 2002; 40:301-308.
Alini, M. et al., "A Biological Approach to Treating Disc Degeneration: Not for Today, But Maybe for Tomorrow," Eur. Spine J., 2002; 11 (Supp. 2 ): S215-220.
Allcock, H.R. et al., "Synthesis of Poly[(Amino Acid Alkyl Ester)Phosphazenes]1-3," *Macromolecules*, 1977; 10(4):824-830.
Altman, G.H. et al., "Advanced Bioreactor With Controlled Application of Multi-Dimensional Strain for Tissue Engineering," *J. Biomech. Eng.*, 2002; 124:742-749.
Altman, R.D. et al., "Radiographic Assessment of Progression in Osteoarthritis," *Arthritis & Rheum.*, 1987; 30(11):1214-1225.
Anseth, K.S. et al., "In Situ Forming Degradable Networks and Their Application in Tissue Engineering and Drug Delivery," *J. of Controlled Release*, 2002; 78:199-209.
Armulik, A. et al., "Endothelial/Pericyte Interactions," *Circ. Res.*, 2005; 97:512-523.
Aston, J. E., et al., "Repair of Articular Surfaces by Allografts of Articular and Growth-Plate Cartilage," *Journal of Bone and Joint Surgery*, 1986; 68-B(1):29-35.
Auda-Boucher, G. et al., "Staging of the Commitment of Murine Cardiac Cell Progenitors," *Dev. Bio.*, 2000; 225(1):214-225.
Avital, I. et al., "Isolation, Characterization, and Transplantation of Bone Marrow-Derived Hepatocyte Stem Cells," *Biochem. & Biophys. Res. Comm.*, 2001; 288:156-164.
Azizi, S.A. et al., "Engraftment and Migration of Human Bone Marrow Stromal Cells Implanted in The Brains of Albino Rats—Similarities to Astrocyte Grafts," *Proc. Natl. Acad. Sci. USA*, 1998; 95:3908-3913.
Bai, M., et al, "Dimerization of the Extracellular Calcium-sensing Receptor (CaR) on the Cell Surface of CaR-Transfected HEK293 Cells," *J. Biol Chem.*, 1998; 273(36): 23605-23610.
Baker, K.A. et al., "Intrastriatal and Intranigral Grafting of hNT Neurons in the 6-OHDA Rat Model of Parkinson's Disease," *Exper. Neurol.*, 2000; 162:350-360.
Bakhshi, et al. "Mesenchymal stem cells from the Wharton's jelly of umbilical cord segments provide stromal support for the maintenance of cord blood hematopoietic stem cells during long-term ex vivo culture", Transfusion, 2008; 48: 2638-2644.
Balis, F. et al., "Central Nervous System Pharmacology of Antileukemic Drugs," *Am. J. of Pediatric Hematol. Oncol.*, 1989; 11(1):74-86.
Balkema, G.W. et al., "Impaired Visual Thresholds in Hypopigmented Animals," *Visual Neuroscience*, 1991; 6:577-585.
Bao, Z.Z. et al., "Regulation of Chamber-Specific Gene Expression in the Developing Heart by IrX 4," *Science*, 1999; 283(5405):1161-1164.
Barberi, T. et al., "Neural Subtype Specification of Fertilization and Nuclear Transfer Embryonic Stem Cells and Application in Parkinsonian Mice," *Nature Biotechnology*, 2003; 21(10):1200-1207.
Beck, R.W. et al., "A Clinical Comparison of Visual Field Testing With a New Automated Perimeter, The Humphrey Field Analyzer, and the Goldmann Perimeter," *Ophthalmology*, 1985; 92(1):77-82.
Bennett et al., "A Peripheral Mononeuropathy in Rate that Produces Disorders of Pain Sensation Like Those Seen in Man," Pain, 1988; 33:87-107.
Bergers, G. et al., "The Role of Pericytes in Blood-Vessel Formation and Maintenance," *Neuro-Oncology*, 2005; 7:452-464.
Bhindi, R. et al., "Rat Models of Mycocardial Infarction," *Thromb Haemost*, 2006; 96:602-610.

Björklund, L.M. et al., "Embryonic Stem Cells Develop Into Functional Dopaminergic Neurons After Transplantation in a Parkinson Rat Model," *PNAS*, 2002; 99(4):2344-2349.
Blakemore et al., "Modelling Large Areas of Demyelination in the Rat Reveals the Potential and Possible Limitations of Transplanted Glial Cells for Remyelination in the CNS," *GLIA*, 2002; 38:155-168.
Bradley, B.A., "The Role of HLA Matching in Transplantation," *Immunol. Lett.*, 1991; 29:55-59.
Brodsky, S.V., "Coagulation, Fibrinolysis and Angiogenesis: New Insights From Knockout Mice," *Exp. Nephrol.*, 2002; 10:299-306.
Brooks, P., "Inflammation as an Important Feature of Osteoarthritis," *Bull. World Health Org.*, 2003; 81(9):689-690.
Brown, J.A. et al., "Blockade of Programmed Death-1 Ligands on Dendritic Cells Enhances T Cell Activation and Cytokine Production," *J. Immunology*, 2003; 170:1257-1266.
Bruder et al., "Mesenchymal Stem Cell Surface Antigen SB-10 Corresponds to Activated Leukocyte Cell Adhesion Molecule and Is Involved in Osteogenic Differentiation," *Journal of Bone and Mineral Research*, 1998; 13(4):655-663.
Bunge et al., "The Role of the Schwann Cell in Trophic Support and Regeneration," Journal of Neurology, 1994; 241:536.
Burnstein, R.M. et al., "Differentiation and Migration of Long Term Expanded Human Neural Progenitors in a Partial Lesion Model of Parkinson's Disease," *Intern. J. of Biochem. & Cell Biology*, 2004; 36:702-713.
Bussolati et al., "Isolation of Renal Progenitor Cells from Adult Human Kidney," *American Journal of Pathology*, 2005; 166(2):545-555.
Caballero, S. et al., "The Many Possible Roles of Stem Cells in Age-Related Macular Degeneration," *Graefe's Arch. Clin. Exp. Ophthalmol.*, 2004; 242:85-90.
Campbell, I.K. et al., "Human Articular Cartilage and Chondrocytes Produce Hemopoietic Colony-Stimulating Factors in Culture in Response to IL-1," *J. of Immun.*, 1991; 147(4):1238-1246.
Can et al., "Concise Review: Human Umbilical Cord Stroma with Regard to the Source of Fetus-Derived Stem Cells," Stem Cells, 2007; 25:2886-2895.
Cao, Q. et al., "Stem Cell Repair of Central Nervous System Injury," *J. of Neuroscience Res.*, 2002; 68:501-510.
Caplan, A.I. et al., "Mesenchymal Stem Cells: Building Blocks for Molecular Medicine in the 21st Century," *Trends in Molecular Med.*, 2001; 7(6):259-264.
Carter, D. et al., "Characterization of MSC Potential to Treat GVHD Using Molecular Markers Linked to MSC-Mediated Immunosuppression In Vitro," *Blood*, 2005; 106(11) part 2, Abstract No. 4322, 160B.
"Cell Lysis, p. 2" http://www.piercenet.com/objects/view.cfm?type=Page&ID=1904ED25-8FA4-475C-8068-C2E813D5F4E7; accessed Aug. 7, 2008.
Chagraoui, J. et al., "Fetal Liver Stroma Consists of Cells in Epithelial-to-Mesenchymal Transition," *Blood*, 2003; 101(8):2973-2982.
Chen, D. et al. "Differential Roles for Bone Morphogenic Protein (BMP) Receptor Type IB and IA in Differentiation and Specification of Mesenchymal Precursor Cells to Osteoblast and Adipocyte Lineages," *J. Cell Biol.*, 1998; 142(1):295-305.
Chen, H. et al., "The Effect of Hypothermia on Transient Middle Cerebral Artery Occlusion in the Rat," *J. Cereb. Blood Flow Metab.*, 1992; 12(4):621-628.
Chen, J. et al., "Intravenous Administration of Human Umbilical cord Blood Reduces Behavioral Deficits After Stroke in Rats," *Stroke*, 2001; 32:2682-2688.
Chen, J. et al., "Therapeutic Benefit of Intravenous Administration of Bone Marrow Stromal Cells after Cerebral Ischemia in Rats," *Stroke*, 2001; 32(4):1005-1011.
Cheng, A. et al. "Nitric Oxide Acts in a Positive Feedback Loop With BDNF to Regulate Neural Progenitor Cell Proliferation and Differentiation in the Mammalian Brain," *Dev. Biol.*, 2003; 258:319-333.
Chujo, T. et al., "Effects of Growth Differentiation Factor-5 on the Intervertebral Disc-In Vitro Bovine Study and In Vivo Rabbit Disc Degeneration Model Study," Spine, 2006; 31: 2909-2917.

(56) References Cited

OTHER PUBLICATIONS

Constantini, S. et al., "The Effects of Methylprednisolone and the Ganglioside GM1 on Acute Spinal Cord Injury in Rats," *J. Neurosurg.*, 1994; 80(1):97-111.
Coumans, B. et al., "Lymphoid Cell Apoptosis Induced by Trophoblastic Cells: A Model of Active Foeto-Placental Tolerance," *J. of Immunological Methods*, 1999; 224:185-196.
D'Cruz, P.M. et al., "Mutation of the Receptor Tyrosine Kinase Gene Mertk in the Retinal Dystrophic RCS Rat," *Hum. Mol. Genet.*, 2000; 9(4):645-651.
Daley, G.Q. et al., "Realistic Prospects for Stem Cell Therapeutics," *Hematol.*, 2003; 398-418.
Danon, D. et al., "Macrophage Treatment of Pressure Sores in Paraplegia," *J. Wound Care*, 1998; 7(6):281-283.
Danon, D. et al., "Treatment of Human Ulcers by Application of Macrophages Prepared From a Blood Unit," *Exp. Gerontol.*, 1997; 32(6):633-641.
Dawson, T.M. et al., "Neuroprotective and Neurorestorative Strategies for Parkinson's Disease," *Nat. Neurosci.*, 2002; 5 Suppl.:1058-1061.
Del Monte, F. et al., "Improvement in Survival and Cardiac Metabolism After Gene Transfer of Sarcoplasmic Reticulum Ca $^{2+}$-ATPase in a Rat Model of Heart Failure," *Circulation*, 2001;104:1424-1429.
Diao et al, "Human Umbilical Cord Mesenchymal Stem Cells: Osteogenesis In Vivo as Seed Cells for Bone Tissue Engineering," *J. BioMed Mater Res.*, 2009; 91A:123-131.
Dickinson, A.M. et al., "Non-HLA Immunogenetics in Hematopoietic Stem Cell Transplantation," *Curr. Opin. Immunol.*, 2005; 17(5):517-525.
Dimri, G.P. et al., "A Biomarker That Identifies Senescent Human Cells in Culture and in Aging Skin In Vivo," *Proc. Natl. Acad. Sci. USA*, 1995; 92:9363-9367.
Domb, A. et al., "Degradable Polymers for Site-Specific Drug Delivery," *Polymers for Advanced Technologies*, 1992; 3:279-292.
Doshi, S.N. et al., "Evolving Role of Tissue Factor and Its Pathway Inhibitor," *Critical Care Med.*, 2002; 30(5):S241-S250.
Doyle, J., "Spiraling Complexity, Robustness, and Fragility in Biology," http://www.cds.caltech.edu/—doyle/CmplxNets/Bio1.pdf, available online Feb. 28, 2004.
Draper et al., "Surface Antigens of Human Embryonic Stem Cells: Changes Upon Differentiation in Culture," J. Anat., 2002; 200:249-258.
Dutton, R, et al., "Precursor Cells in the Subventricular Zone of the Adult Mouse Are Actively Inhibited from Differentiating into Neurons,"*Dev Neurosci*, 2000; 22:96-105.
Du, Y. et al., "Functional Reconstruction of Rabbit Corneal Epithelium by Human Limbal Cells Cultured on Amniotic Membrane," *Molecular Vision*, 2003; 9:635-643.
Dykens, J. et al., "Photoreceptor Preservation in the S334ter Model of Retinitis Pigmentosa by a Novel Estradiol Analog", *Biochemical Pharmacology*, 2004; 68: 1971-1984.
Eagle, H., "The Specific Amino Acid Requirements of a Mammalian Cell (Strain L) in Tissue Culture," *J. Biol. Chem.*, 1955; 214:839-852.
Eblenkamp, M. et al., "Umbilical Cord Stromal Cells (UCSC). Cells Featuring Osteogenic Differentiation Potential," *Der Orthopäde*, Dec. 2004; 33:1338-1345 (English abstract on p. 1339).
Edelstein, M. L. et al., "Gene Therapy Clinical Trials Worldwide 1989-2004—An Overview," *J. Gene Med.*, 2004; 6(6):597-602.
Edlund, H., "Pancreatic Organogenesis—Developmental Mechanisms and Implications for Therapy," *Nat. Rev. Genet.*, 2002; 3:524-532.
Efrat, S. et al., "Cell Replacement Therapy for Type 1 Diabetes," *Trends in Molecular Medicine*, 2002; 8(7):334-339.
Ehtesham, M. et al., "Induction of Glioblastoma Apoptosis Using Neural Stem Cell-Mediated Delivery of Tumor Necrosis Factor-Related Apoptosis-Inducing Ligand," *Cancer Res.*, 2002; 62:7170-7174.

Ehtesham, M. et al., "The Use of Interleukin 12-Secreting Neural Stem Cells for the Treatment of Intracranial Glioma," *Cancer Res.*, 2002; 5657-5663.
Eisenhofer, G.E. et al., "Tyrosinase: A Developmentally Specific Major Determinant of Peripheral Dopamine," *FASEB J.*, 2003; 17:1248-1255.
Ende, N. et al., "Parkinson's Disease Mice and Human Umbilical Cord Blood," *J. Med.*, 2002; 33(1-4):173-180.
Engstad, C.S. et al., "The Effect of Soluble β-1,3-Glucan and Lipopolysaccharide on Cytokine Production and Coagulation Activation in Whole Blood," *Int. Immunopharmacol.*, 2002; 2:1585-1597.
Enzmann, V. et al., "Enhanced Induction of RPE Lineage Markers in Pluripotent Neural Stem Cells Engrafted Into The Adult Rat Subretinal Space," *Investig. Ophthalmol. Visual Sci.*, 2003; 44:5417-5422.
Erices et al., "Mesenchymal Progenitor Cells in Human Umbilical Cord Blood," *Br. J. Haematol.*, 2000; 109:235-242.
Evers, B.M., et al., "Stem Cells in Clinical Practice," *J Am Coll Surg.* 2003; 197(3):458-478.
Fazleabas, A.T. et al., "Endometrial Function: Cell Specific Changes in the Uterine Environment," *Mol. & Cellular. Endo.*, 2002; 186:143-147.
Fernandes, A.M. et al., "Mouse Embryonic Stem Cell Expansion in a Microcarrier-based Stirred Culture System," *Journal of Biotechnology*, 2007; 132:227-236.
Fiegel, H.C. et al., "Liver-Specific Gene Expression in Cultured Human Hematopoietic Stem Cells," *Stem Cells*, 2003; 21:98-104.
Fields, G.B., "Induction of Protein-Like Molecular Architecture by Self-Assembly Processes," *Bioorg. Med. Chem.*, 1999; 7:75-81.
Fischer, D. et al., "Lens-Injury-Stimulated Axonal Regeneration Throughout the Optic Pathway of Adult Rats," *Exp. Neurol.*, 2001; 172:257-272.
Foley, A. et al., "Heart Induction: Embryology to Cardiomyocyte Regeneration," *Trends Cardiovasc. Med.*, 2004; 14(3):121-125.
Franc, S. et al., "Microfibrillar Composition of Umbilical Cord Matrix : Characterization of Fibrillin, Collagen VI and Intact Collagen V," *Placenta*, 1988; 19:95-104.
Freed, C.R. et al., "Transplantation of Embryonic Dopamine Neurons for Severe Parkinson's Disease," *N. Engl. J. Med.*, 2001; 344(10):710-719.
Frenkel, O. et al., "Activated Macrophages for Treating Skin Ulceration: Gene Expression in Human Monocytes After Hypo-Osmotic Shock," *Clin. Exp. Immunol.*, 2002; 128:59-66.
Friedman, J.A. et al., "Biodegradable Polymer Grafts for Surgical Repair of the Injured Spinal Cord," *Neurosurgery*, 2002; 51(3):742-751.
Fukuchi, Y. et al., "Human Placenta-Derived Cells Have Mesenchymal Stem/Progenitor Cell Potential," *Stem Cells*, 2004; 22:649-658.
Fukuda, K., "Reprogramming of Bone Marrow Mesenchymal Stem Cells Into Cardiomyocytes," *C.R. Biol.*, 2002; 325:1027-1038.
Gellersen, B. et al., "Cyclic AMP and Progesterone Receptor Cross-Talk in Human Endometrium: A Decidualizing Affair," *J. Endocrinol.*, 2003; 178(3):357-372.
Gerdes, D. et al., "Cloning and Tissue Expression of Two Putative Steroid Membrane Receptors," *Biol. Chem.*, 1998; 379:907-911.
Giunta et al., "Inflammaging as a Prodrome to Alzheimer's Disease," Journal of Neuroinflammation, 2008; 5(1):51.
Gong, C., et al., "Intracerebral Hemorrhage-Induced Neuronal Death," *Neurosurgery*, 2001; 48(4):875-883.
Gong, C., et al., "Acute Inflammatory Reaction Following Experimental Intracerebral Hemorrhage in Rat," *Brain Res*, 2000; 871:57-65.
Gökhan, S. et al., "Basic and Clinical Neuroscience Applications of Embryonic Stem Cells," *Anat. Rec. (New Anat)*, 2001; 265:142-156.
Goodwin, H.S. et al., "Multilineage Differentiation Activity by Cells Isolated from Umbilical Cord Blood: Expression of Bone, Fat, and Neural Markers," *Biology of Blood and Marrow Transplantation*, 2001; 7:581-588.
Gosiewska, A. et al., "Development of a Three-Dimensional Transmigration Assay for Testing Cell-Polymer Interactions for Tissue Engineering Applications," *Tissue Eng.*, 2001; 7(3):267-277.

(56) References Cited

OTHER PUBLICATIONS

Gottleib, D.I. "Large-Scale Sources of Neural Stem Cells," *Annu. Rev. Neurosci.*, 2002; 25:381-407.
Gröhn, P. et al., "Collagen-Coated BA$^{2+}$-Alginate Microcarriers for the Culture of Anchorage-Dependent Mammalian Cells," *BioTechniques*, 1997; 22(5): 970-975.
Gupta, S. et al., "Isolation and Characterization of Kidney-Derived Stem Cells," *J. of Am. Soci. of Nephrol.*, 2006; 17(11):3028-3040.
Halvorsen, Y.C. et al., "Extracellular Matrix Mineralization and Osteoblast Gene Expression by Human Adipose Tissue-Derived Stromal Cells," *Tissue Eng.*, 2001; 7(6):729-741.
Hanahan, D. "Heritable Formation of Pancreatic β-Cell Tumours in Transgenic Mice Expressing Recombinant Insulin/Simian Virus 40 Oncogenes," *Nature*, 1985; 315:115-122.
Hartgerink, J.D. et al., "Peptide-Amphiphile Nanofibers: A Versatile Scaffold for the Preparation of Self-Assembling Materials," PNAS, 2002; 99(8):5133-5138.
Haruta, M. et al., "In Vitro and In Vivo Characterization of Pigment Epithelial Cells Differentiated From Primate Embryonic Stem Cells," *Investig. Ophthalmol. & Visual Sci.*, 2004; 45(3):1020-1025.
Hayflick, L., "The Longevity of Cultured Human Cells," *J. Am. Geriatr. Soc.*, 1974; 22(1):1-12.
Hayflick, L., "The Strategy of Senescence," *Gerontologist*, 1974; 14(1):37-45.
Haynesworth et al., "Cell Surface Antigens on Human Marrow-Derived Mesenchymal Cells are Detected by Monoclonal Antibodies," Bone, 1992; 13:69-80.
Herrera, M.B. et al., "Mesenchymal Stem Cells Contribute to the Renal Repair of Acute Tubular Epithelial Injury," *Int. J. Mol. Med.*, 2004; 14(6):1035-1041.
Hill, D.P. et al., "Screening for Novel Pattern Formation Genes Using Gene Trap Approaches," *Methods in Enzymology*, 1993; 225:664-681.
Hill, M. et al., "Treatment for Swallowing Difficulties (Dysphagia) in Chronic Muscle Disease," *The Cochrane Library Cochrane Database Syst Rev.*, 2004; 2:1-12.
Hishikawa, K. et al., "Musculin/MyoR is Expressed in Kidney Side Population Cells and Can Regulate Their Function," *Journal of Cell Biology*, 2005; 169(6):921-928.
Holz, F.G. et al., "Intraocular Microablation of Choroidal Tissue by a 308 nm AIDA Excimer Laser for RPE-Transplantation in Patients With Age-Related Macular Degeneration," *Biomed. Technik*, 2003; 48:82-85.
Hongpaisan, J., "Inhibition of Proliferation of Contaminating Fibroblasts by D-Valine in Cultures of Smooth Muscle Cells From Human Myometrium," *Cell Biol. Int.*, 2000; 24(1):1-7.
Hoynowski, S.M. et al., "Characterization and Differentiation of Equine Umbilical Cord-Derived Matrix Cells," *Biochemical and Biophysical Research Communications*, 2007; 362:347-353.
Hu, A. et al., "Hepatic Differentiation From Embryonic Stem Cells In Vitro," Chin. Med. J., 2003; 116(12):1893-1897.
Hua, Y., et al., "Plasminogen Activator Inhibitor-1 Induction after Experimental Intracerebral Hemorrhage," *J. Cereb Blood Flow Metab*, 2002; 22:55-61.
Hua, Y., et al., "Behavioral Tests After Intracerebral Hemorrhage in the Rat," *Stroke*, 2002; 33:2478-2484.
Hughes, G.C. et al., "Therapeutic Angiogenesis in Chronically Ischemic Porcine Myocardium: Comparative Effects of BFGF and VEGF," *Ann. Thorac. Surg.*, 2004; 77:812-818.
Hutmacher, D.W., "Scaffold Design and Fabrication Technologies for Engineering Tissues—State of the Art and Future Perspectives," *J. Biomater. Sci. Polymer Edn.*, 2001;12(1):107-124.
Igura et al. "Human Placental Derived Stem Cells Differentiate into Neural Cells," Blood , 2002; 100(11): 517A (Abstract 2021).
In'T Anker, P., et al., "Isolation of Mesenchymal Stem Cells of Fetal or Maternal Origin from Human Placenta," *Stem Cells*, 2004; 22:1338-1345.
Isacson, O., "The Production and Use of Cells as Therapeutic Agents in Neurodegenerative Diseases," *The Lancet (Neurology)*, 2003; 2:417-424.

Isacson, O., et al., "Specific Axon Guidance Factors Persist in the Adult Brain as Demonstrated by Pig Neuroblasts Transplanted to the Rat," *Neurosci.*, 1996; 75(3):827-837.
Ishii, M. et al., "Molecular Markers Distinguish Bone Marrow Mesenchymal Stem Cells From Fibroblasts," *Biochemical and Biophysical Research Communications*, 2005; 332:297-303.
Ito, Y. et al., "A Quantitative Assay Using Basement Membrane Extracts to Study Tumor Angiogenesis In Vivo," *Int. J. Cancer*, 1996; 67:148-152.
Jackson, K.A. et al., "Regeneration of Ischemic Cardiac Muscle and Vascular Endothelium by Adult Stem Cells," *J. Clin. Invest.*, 2001; 107:1395-1402.
Jaffe, E.A. et al., "Culture of Human Endothelial Cells Derived From Umbilical Veins; Identification by Morphologic and Immunologic Criteria" *J Clin Invest*, 1973; 52:2745-2756.
Janderová, L. et al., "Human Mesenchymal Stem Cells as an In Vitro Model for Human Adipogenesis," *Obes. Res.*, 2003; 11(1):65-74.
Jang, Y.K. et al., "Retinoic Acid-Mediated Induction of Neurons and Glial Cells From Human Umbilical Cord-Derived Hematopoietic Stem Cells," *J. Neurosci. Res.*, 2004; 75:573-584.
Jikuhara, T. et al., "Left Atrial Function as a Reliable Predictor of Exercise Capacity in Patients With Recent Myocardial Infarction," *Chest*, 1997; 111(4):922-928.
Jin et al., "Neurogenesis in Dentate Subgranular Zone and Rostral Subventricular Zone After Focal Cerebral Ischemia in the Rat," *PNAS*, 2001; 98(8):4710-4715.
Johe, K.K. et al., "Single Factors Direct the Differentiation of Stem Cells From the Fetal and Adult Central Nervous System," *Genes & Devel.*, 1996; 10:3129-3140.
Johnstone, B. et al., "In Vitro Chondrogenesis of Bone-Marrow-Derived Mesenchymal Progenitor Cells," *Exp. Cell Res.*, 1998; 238:265-272.
Jomura, S. et al., "Potential Treatment of Cerebral Global Ischemia with Oct-4+ Umbilical Cord Matrix Cells," *Stem Cells*, 2006, AlphaMed Press, Downloaded from www.StemCells.com at Ethicon, Inc. on Sep. 11, 2006 and Supplemental Data: 2.
Jones, J. et al., "Insulin-Like Growth Factors and their Binding Proteins: Biological Actions," Endocrine Review, 1995; 16(1):3-34.
Jones-Villeneuve, E.M. et al., "Retinoic Acid-Induced Neural Differentiation of Embryonal Carcinoma Cells," *Mol. & Cellu. Biol.*, 1983; 3(12):2271-2279.
Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, 2002; 277(9):7574-7580.
Joussen, A.M. "Cell Transplantation in Age Related Macular Degeneration: Current Concepts and Future Hopes," *Graefe's Arch. Clin. Exp. Ophthalmol.*, 2004; 242:1-2.
Kadiyala, S. et al., "Culture Expanded Canine Mesenchymal Stem Cells Possess Osteochondrogenic Potential In Vivo and In Vitro," *Cell Transplant.*, 1997; 6(2):125-134.
Kawata, M. et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," *J. Exp. Med.*, 1984; 160:633-651.
Keyvani, et al., "Plasticity-Associated Molecular and Structural Events in the Injured Brain," *Journal of Neuropathology Experimental Neurology*, 2002; 61(10):831-840.
Kicic, A. et al., "Differentiation of Marrow Stromal Cells Into Photoreceptors in the Rat Eye," *J. of Neurosci.*, 2003; 23(21):7742-7749.
Kim, J. et al., "Dopamine Neurons Derived From Embryonic Stem Cells Function in an Animal Model of Parkinson's Disease," *Nature*, 2002; 418:50-56.
Kim, J.Y. et al., "Ocular Surface Reconstruction: Limbal Stem Cell Transplantation," *Ophthal. Clin. N. Am.*, 2003; 16:67-77.
Kim, S.K. et al., "Intercellular Signals Regulating Pancreas Development and Function," *Genes Dev.*, 2001; 15:111-127.
Kirschstein, R. et al., "Can Stem Cells Repair a Damaged Heart?" *Stem Cells: Scientific Progress and Future Research Directions*, 2001; 87-92.

(56) References Cited

OTHER PUBLICATIONS

Kitamura,. S. et al., "Establishment and Characterization of Renal Progenitor Like Cells from S3 Segment of Nephron in Rat Adult Kidney," *The FASEB Journal*, 2005; 19:1789-1797.
Klass et al., "Intravenous Mononuclear Marrow Cells Reverse Neuropathic Pain from Experimental Mononeuropathy," International Anesthesia Research Society, 2007; 104:944-949.
Klassen, H. et al., "Stem Cells and Retinal Repair," *Prog. Retin. Eye Res.*, 2004; 23:149-181.
Kolb, B, "Synaptic Plasticity and the Organization of Behaviour after Early and Late Brain Injury," *Canadian Journal of Experimental Psychology*, 1999; 53(1):62-76.
Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76:1643-1648.
Kusama, V. et al., "Growth and morphogenesis of mouse prostate epithelial cells in collagen gel matrix culture" *Cell Biol Int Rep*, 1989; 13:569-575.
Laface, D. et al., "Gene Transfer Into Hematopoietic Progenitor Cells Mediated by an Adeno-Associated Virus Vector," *Virology*, 1988; 162:483-486.
Lang, K.J.D. et al., "Differentiation of Embryonic Stem Cells to a Neural Fate: A Route to Re-Building the Nervous System?" *J. of Neurosci. Res.*, 2004; 76:184-192.
Langeggen, H. et al., "HUVEC Take Up Opsonized Zymosan Particles and Secrete Cytokines IL-6 and IL-8 In Vitro," *FEMS Immunol. Med. Microbiol.*, 2003; 36:55-61.
Le Belle, J.E. et al., "Stem Cells for Neurodegenerative Disorders: Where Can We Go From Here?," *Biodrugs*, 2002; 16(6):389-401.
Le Bouteiller, P. et al., "Soluble HLA-G1 at the Materno-Foetal Interface—A Review," *Placenta*, 2003; 24(Suppl. A):S10-S15.
Li, A. et al., "IL-8 Directly Enhanced Endothelial Cell Survival, Proliferation, and Matrix Metalloproteinases Production and Regulated Angiogenesis," *J. Immunol.*, 2003; 170:3369-3376.
Li, C.D. et al, "Mesenchymal Stem Cells Derived From Human Placenta Suppress Allogeneic Umbilical Cord Blood Lymphocyte Proliferation," *Cell Research*, 2005; 15(7):539-547.
Li, L.X. et al., "Inherited Retinal Dystrophy in the RCS Rat: Prevention of Photoreceptor Degeneration by Pigment Epithelial Cell Transplantation," *Exp. Eye Res.*, 1988; 47:911-917.
Li, Y. et al., "Transplanted Olfactory Ensheathing Cells Promote Regeneration of Cut Adult at Optic Nerve Axons," *J. of Neuro.*, 2003; 23(21):7783-7788.
Li, Y. et al., "Intracerebral Transplantation of Bone Marrow Stromal Cells in a 1-Methyl-4-Phenyl-1,2,3,6-Tetrahydropyridine Mouse Model of Parkinson's Disease," *Neuroscience Letts.*, 2001; 315:67-70.
Li, Y. et al., "Intact, Injured, Necrotic and Apoptotic Cells after Focal Cerebral Ischemia in the Rat," *J. Neurol. Sci.*, 1998; 156:119-132.
Li, Y. et al., "Ultrastructural and Light Microscopic Evidence of Apoptosis after Middle Cerebral Artery Occlusion in the Rat," *Am. J. Pathol.*, 1995; 146(5):1045-1051.
Li, Y. et al., "Human Marrow Stromal Cell Therapy for Stroke in Rat Neurotrophins and Functional Recovery," *Neurology*, 2002; 59:514-523.
Liddiard, et al., "An Improved Method for the Preparation of Human Fetal and Adult Hepatocytes," *Arch. Toxicol.*, 1980; 44:107-112.
Lindenlaub, T. et al., "Partial Sciatic Nerve TranseCtion as a Model of Neuropathic Pain: A Qualitative and Quantitative Study," *PAIN*, 2000; 89: 97-106.
Lindvall, O. et al., "Stem Cell Therapy for Human Neurodegenerative Disorders—How to Make It Work," *Nature Medicine*, 2004;10(Suppl.):S42-S50.
Liu, Y. et al., "Molecular and Genetic Mechanisms of Obesity: Implications for Future Management," *Curr. Mol. Med.*, 2003; 3(4):325-340.
Liu, K. et al, "Constitutive and Regulated Expression of Telomerase Reverse Transcriptase (hTERT) in Human Lymphocytes," *Proc. Natl. Acad. Sci.*, 1999; 96:5147-5152.
Lockhart, D.J. et al., "Expression Monitoring by Hybridization to High-Density Oligonucleotide Arrays," *Nat. Biotechnol.*, 1996; 14:1675-1680.
Lodie, T.A. et al., "Systematic Analysis of Reportedly Distinct Populations of Mulitpotent Bone Marrow-Derived Stem Cells Reveals a Lack of Distinction," *Tissue Engineering*, 2002; 8(5):739-751.
Lois, C. et al., "Chain Migration of Neuronal Precursors," *Science*, 1996; 271:978-981.
Lund, R.D. et al., "Cell Transplantation as a Treatment for Retinal Disease," *Progress in Retinal and Eye Research*, 2001; 20(4):415-449.
Lund, R.D. et al., "Subretinal Transplantation of Genetically Modified Human Cell Lines Attenuates Loss of Visual Function in Dystrophic Rats," *PNAS*, 2001; 98(17):9942-9997.
Lund, R.D. et al., "Retinal Transplantation: Progress and Problems in Clinical Application," *J. Leukocyte Biol.*, 2003; 74:151-160.
Luo, D. et al., "Synthetic DNA Delivery Systems," *Nat. Biotechnol.*, 2000; 18(1):33-36.
Luyten, F.P. et al., "Skeletal Tissue Engineering: Opportunities and Challenges," *Best Pract. Res. Clin. Rheumatol.*, 2001; 15(5):759-769.
Ma, L. et al., "Human Umbilical Cord Wharton's Jelly-Derived Mesenchymal Stem Cells Differentiation into Nerve-Like Cells," *Chinese Med. Jour.*, 2005; 118(23):1987-1993.
MacDonald, R.J. "Expression of the Pancreatic Elastase I Gene in Transgenic Mice," *Hepatology*, 1987; 7(1):42S-51S.
Mackay, A.M. et al., "Chondrogenic Differentiation of Cultured Human Mesenchymal Stem Cells From Marrow," *Tissue Engineering*, 1998; 4(4):415-428.
Makino, S. et al., "Cardiomyocytes can be generated from marrow stromal cells in vitro," J. Clin. Invest., 1999; 103:697-705.
Marx, W.F. et al., "Endovascular Treatment of Experimental Aneurysms by Use of Biologically Modified Embolic Devices: Coil-Mediated Intraaneurysamal Delivery of Fibroblast Tissue Allografts," *Am. J. Neuroradiol.*, 2001; 22:323-333.
Mason, A.J. et al., "The Hypogonadal Mouse: Reproductive Functions Restored by Gene Therapy," *Science*, 1986; 234:1372-1378.
Matsushita et al., "Evidence for Apoptosis After Intracerebral Hemorrhage in Rat Striatum," *Journal of Cerebral Blood Flow & Metabolism*, 2000; 20:396-404.
Mayer-Proschel, M. et al., "Isolation of Lineage-Restricted Neuronal Precursors From Multipotent Neuroepithelial Stem Cells," *Neuron.*, 1997; 19:773-785.
Medicetty, S. et al., "Transplantation of Human Umbilical Cord Matrix Stem Cells Alleviates Apomorphine-Induced Rotations in Parkinsonian Rats", 2003, XP-002383776, 1 page.
Meier et al., "Spastic Paresis After Perinatal Brain Damage in Rats is Reduced by Human Cord Blood Monomuclear Cells," *Pediatric Research*, 2006; 59(2):244-249.
Melero-Martin, J. et al., "Optimal In-Vitro Expansion of Chondroprogenitor Cells in Monolayer Culture," *Biotechnology and Bioengineering*, 2006; 93(3):519-533.
Merx, M.W. et al., "Transplantation of Human Umbilical Vein Endothelial Cells Improves Left Ventricular Function in a Rat Model of Myocardial Infarction," *Basic Res. Cardiol.*, 2005; 100:208-216.
Messina, D.J., et al., "Comparison of Pure and Mixed Populations of Human Fetal-Derived Neural Progenitors Transplanted Into Intact Adult Rat Brain," *Exper. Neurol.*, 2003; 184:816-829.
Miñambres et al., "Cerebral Apoptosis in Severe Traumatic Brain Injury Patients: An In Vitro, In Vivo, and Postmortem Study," *Journal of Neurotrauma*, 2008; 25:581-591.
Mitchell, K.E. et al., "Matrix Cells From Wharton's Jelly Form Neurons and Glia," *Stem Cells*, 2003; 21:50-60.
Moll, S. et al., "Monitoring Warfarin Therapy in Patients With Lupus Anticoagulants," *Ann. Intern. Med.*, 1997; 127(3):177-185.
Mombaerts, P. et al., "Creation of a Large Genomic Deletion at the T-Cell Antigen Receptor β-Subunit Locus in Mouse Embryonic Stem Cells by Gene Targeting," *Proc. Nat. Acad. Sci. USA*, 1991; 88:3084-3087.

(56) References Cited

OTHER PUBLICATIONS

Morgenstern, J.P. et al., "Advanced Mammalian Gene Transfer: High Titre Retroviral Vectors With Multiple Drug Selection Markers and a Complementary Helper-Free Packaging Cell Line," *Nucleic Acids Res.*, 1990; 18(12):3587-3596.
Moore, A.E. et al., "Parkinsonian Motor Deficits are Reflected by Proportional A9/A10 Dopamine Neuron Degeneration in the Rat," *Exp. Neurol.*, 2001; 172(2):363-376.
Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.
Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-4206.
Moulder, J.E., "Pharmacological Intervention to Prevent or Ameliorate Chronic Radiation Injuries," *Semin. Radiat. Oncol.*, 2003; 13(1):73-84.
Nakamura, T. et al., "Ocular Surface Reconstruction Using Cultivated Mucosal Epithelial Stem Cells," *Cornea*, 2003; 22(Supp. 1):S75-S80.
Naughton, B.A. et al., "Cells isolated from Wharton's jelly of the human umbilical cord develop a cartilage phenotype when treated with TGF-b in vitro," 1997; *FASEB J* 11:A19 (Abstract 108).
Nicosia, R.F. et al., "Modulation of Microvascular Growth and Morphogenesis by Reconstituted Basement Membrane Gel in Three-Dimensional Cultures of Rat Aorta: A Comparative Study of Angiogenesis in Matrigal, Collagen, Fibrin, and Plasma Clot," *In Vitro Cell Dev. Biol.*, 1990; 26:119-128.
Ninichuk, V. et al., "Multipotent Mesenchymal Stem Cells Reduce Interstitial Fibrosis but Do Not Delay Progression of Chronic Kidney Disease in Collagen4A3-Deficient Mice," *Kidney Int.*, 2006; 70(1):121-129.
Nishishita, T. et al., "A Potential Pro-Angiogenic Cell Therapy With Human Placenta-Derived Mesenchymal Cells," *Biochemical and Biophysical Research Communications*, 2004; 325:24-31.
Nixon, P.J. et al., "The Contribution of Cone Responses to Rat Electroretinograms," *Clin. Experiment Ophthalmol.*, 2001; 29(3):193-196.
Nork, T.M. et al., "Swelling and Loss of Photoreceptors in Chronic Human and Experimental Glaucomas," *Arch. Ophthalmol.*, 2000; 118:235-245.
Nusinowitz, S. et al., "Rod Multifocal Electroretinograms in Mice," *Invest Ophthalmol Vis. Sci.*, 1999; 40(12): 2848-2858.
Oh, S.H. et al., "Hepatocyte Growth Factor Induces Differentiation of Adult Rat Bone Marrow Cells Into a Hepatocyte Lineage In Vitro," *Biochem. & Biophys. Res. Comm.*, 2000; 279(2):500-504.
Okumoto, K. et al., "Differentiation of Bone Marrow Cells Into Cells That Express Liver-Specific Genes In Vitro: Implication of the Notch Signals in Differentiation," *Biochem. & Biophys. Res. Commun.*, 2003; 304:691-695.
Orlic, D. et al., "Stem Cells for Myocardial Regeneration," *Circ. Res.*, 2002; 91:1092-1102.
Ornitz, D.M. et al., "Elastase I Promoter Directs Expression of Human Growth Hormone and SV40 T Antigen Genes to Pancreatic Acinar Cells in Transgenic Mice," *Cold Spring Harbor Symp. Quant. Biol.*, 1985; 50:399-409.
Osborne, N.N. et al., "Some Current Ideas on the Pathogenesis and the Role of Neuroprotection in Glaucomatous Optic Neuropathy," *Eur. J. Ophthalmol.*, 2003; 13(Supp. 3):S19-S26.
Palù, G. et al., "In Pursuit of New Developments for Gene Therapy of Human Diseases," *J. Biotechnol*, 1999; 68:1-13.
Panepucci, R.A. et al., "Comparison of Gene Expression of Umbilical Cord Vein and Bone Marrow-Derived Mesenchymal Stem Cells," *Stem Cells*, 2004; 22:1263-1278.
Parent et al., "Rat Forebrain Neurogenesis and Striatal Neuron Replacement After Focal Stroke," *Ann. Neurol.*, 2002; 52:802-813.
Pera, M.F. et al., "Human Embryonic Stem Cells", *J. Cell Science*, 2000; 113:5-10.
Pesce et al., "Myoendothelial Differentiation of Human Umbilical Cord Blood-Derived Stem Cells in Ischemic Limb Tissues," *Circulation Research*, 2003; 93:e51-e62.
Petersdorf, E.W., "HLA Matching in Allogeneic Stem Cell Transplantation," *Curr. Op. Hematol*, 2004; 11:386-391.
Phipps, J.A. et al., "Paired-Flash Identification of Rod and Cone Dysfunction in the Diabetic Rat," *Investigative Ophthalmology & Visual Science*, 2004; 45 4592-4600.
Pisharodi, M. et al., "An Animal Model for Neuron-Specific Spinal Cord Lesions by the Microinjection of N-Methylaspartate, Kainic Acid, and Quisqualic Acid," 1985; *Appl. Neurophysiology* 48:226-233.
Pittenger, M.F. et al., "Multilineage Potential of Adult Human Mesenchymal Stem Cells," *Science*, 1999; 284:143-47 and seven pages of online supplementary material.
Pittenger, M.F. et al., "Mesenchymal Stem Cells and Their Potential as Cardiac Therapeutics, " *Circ. Res.*, 2004; 95:9-20.
Plaia, T., et al., "Characterization of a New NIH-Registered Variant Human Embryonic Stem Cell Line, BG01V: A Tool for Human Embryonic Stem Cell Research," *Stem Cells*, 2006: 24: 531-546.
Plate, KH, "Mechanisms of Angiogenesis in the Brain," *Journal of Neuropathology Experimental Neurology*, 1999; 58(4):313-320.
Pountos, I. et al., "Mesenchymal Stem Cell Tissue Engineering: Techniques for Isolation, Expansion and Application," *Injury, Int. J. Care Injured*, 2007; 38:S23-S33.
Rabbany, S.Y. et al., "Molecular Pathways Regulating Mobilization of Marrow-Derived Stem Cells for Tissue Revascularization," *TRENDS in Molecular Med.*, 2003; 9(3):109-117.
Rafii, S. et al., "Therapeutic Stem and Progenitor Cell Transplantation for Organ Vascularization and Regeneration," *Nature Med.*, 2003; 9(6):702-712.
Rahman, Z. et al., "Isolation and Primary Culture Urothelial Cells from Normal Human Bladder," *Urol. Research*, 1987; 15:315-320.
Ramon-Cueto, A. et al., "Functional Recovery of Paraplegic Rats and Motor Axon Regeneration in Their Spinal Cords by Olfactory Ensheathing Glia," *Neuron*, 2000; 25:425-435.
Readhead, C. et al., "Expression of a Myelin Basic Protein Gene in Transgenic Shiverer Mice: Correction of the Dysmyelinating Phenotype," *Cell*, 1987; 48:703-712.
Refaie, A. et al., "Experimental Islet Cell Transplantation in Rats: Optimization of the Transplantation Site," *Trans. Proc.*, 1998; 30:400-403.
Rehman, J. et al., "Secretion of Angiogenic and Antiapoptotic Factors by Human Adipose Stromal Cells," *Circulation*, 2004; 109:1292-1298.
Reubinoff, B.E. et al., "Neural Progenitors From Human Embryonic Stem Cells," *Nature Biotechnology*, 2001; 19:1134-1140.
Reyes, M. et al., "Purification and Ex Vivo Expansion of Postnatal Human Marrow Mesodermal Progenitor Cells," *Blood*, 2001; 98(9):2615-2625.
Rezai, K.A. et al., "Iris Pigment Epithelium Transplantation," *Graefe's Arch. Clin. Ophthalmol.*, 1997; 235:558-562.
Rickard, D.J. et al., "Induction of Rapid Osteoblast Differentiation in Rat Bone Marrow Stromal Cell Cultures by Dexamethasone and BMP-2," *Dev. Biol.*, 1994; 161:218-228.
Rios, M. et al., "Catecholamine Synthesis is Mediated by Tyrosinase in the Absence of Tyrosine Hydroxylase," *J. Neurosci.*, 1999, 19(9):3519-3526.
Romanov, Y.A. et al., "Searching for Alternative Sources of Postnatal Human Mesenchymal Stem Cells: Candidate MSC-Like Cells from Umbilical Cord," *Stem Cells*, 2003; 21:105-110.
Rosen, E.M. et al., "HGF/SF in Angiogenesis," *Ciba Found. Symp.*, 1997; 212:215-229.
Roskams, A.J. et al., "Directing Stem Cells and Progenitor Cells on the Stage of Spinal Cord Injury," *Exp. Neurol.*, 2005; 193:267-272.
Russo, E., Cultivating Policy from Cell Types, *The Scientist*, 2001; 15(11):6 (printout is numbered 1-6).
Rutherford, A. et al., "Eyeing-Up Stem Cell Transplantation," *Trends in Molecular Medicine*, 2001; 7(1):11.
Ryadnov, M.G. et al., "Engineering the Morphology of a Self-Assembling Protein Fibre," *Nat. Mater.*, 2003; 2:329-332.

(56) References Cited

OTHER PUBLICATIONS

Sagrinati, C. et al., "Isolation and Characterization of Multipotent Progenitor Cells from the Bowman's Capsule of Adult Human Kidney," *Journal of American Society of Nephrology*, 2006; 17:2443-2456.

Sahn, D.J. et al., "Recommendations Regarding Quantitation in M-Mode Echocardiography: Results of a Survey of Echocardiographic Measurements," *Circulation*, 1978; 58(6):1072-1083.

Sakariassen, K.S. et al., "Methods and Models to Evaluate Shear-Dependent and Surface Reactivity-Desendent Antithrombotic Efficacy," *Thromb. Res.*, 2001; 104:149-174.

Salcedo, R. et al., "Human Endothelial Cells Express CCR2 and Respond to MCP-1: Direct Role of MCP-1 in Angiogenesis and Tumor Progression," *Blood*, 2000; 96(1):34-40.

Salgado, A.J. et al., "Bone Tissue Engineering: State of the Art and Future Trends," *Macromol. Biosci.*, 2004; 4:743-765.

Schallert, T. et al., "Use-Dependent Structural Events in Recovery of Function," *Brain Plasticity, Adv. Neurol.*, 1997; 73:229-238.

Schouten, J.W. et al., "A Review and Rationale for the Use of Cellular Transplantation as a Therapeutic Strategy for Traumatic Brain Injury," *Journal of Neurotrauma*, 2004; 21(11):1501-1538.

Schraermeyer, U. et al., "Subretinally Transplanted Embryonic Stem Cells Rescue Photoreceptor Cells From Degeneration in the RCS Rats," *Cell Transplantation*, 2001; 10:673-680.

Schreuder, G.M. et al., "The HLA Dictionary 1999: A Summary of HLA-A, -B, -C, -DRB1/3/4/5, -DQB1 Alleles and Their Association with Serologically Defined HLA-A, -B, -C, -DR and -DQ Antigens," *Tissue Antigens*, 1999; 54:409-437.

Schwartz, R.E. et al., "Multipotent Adult Progenitor Cells From Bone Marrow Differentiate Into Functional Hepatocyte-Like Cells," *J. Of Clin. Invest.*, 2002; 109:1291-1302.

Seaver, S.S. et al. "The chick oviduct in tissue culture. I. Initial characterization of growing primary oviduct tissue cultures," *Exp. Cell Res.*, 1984; 155: 241-251.

Sébire, G. et al., "In Vitro Production of IL-6, IL-1β, and Tumor Necrosis Factor-α by Human Embryonic Microglial and Neural Cells," *J. Immunol.*, 1993; 150(4):1517-1523.

Seiji, T. et al., Possibility of Regenerative Medicine Using Human Amniotic Cells, *Regenerative Medicine*, 2002; 1(2):79-85. English Language Abstract.

Sethe, S. et al., "Aging of Mesenchymal Stem Cells," *Ageing Research Reviews*, 2006; 5:91-116.

Seyfried, D. et al., "Effects of Intravenous Administration of Human Bone Marrow Stromal Cells After Intracerebral Hemorrhage in Rats," *J Neurosurg*, 2006; 104:313-318.

Seyfried, D. et al., "Improvement in Neurological Outcome after Administration of Atorvastatin Following Experimental Intracerebral Hemorrhage in Rats," *J Neurosurg*, 2004; 101:104-107.

Shake et al., "Mesenchymal stem cell implantation in a swine myocardial infarct model: engraftment and functional effects," *Ann Thorac Surg*, 2002; 73:1919-1926.

Shani, M., "Tissue-Specific Expression of Rat Myosin Light-Chain 2 Gene in Transgenic Mice," *Nature*, 1985; 314:283-286.

Shimizu, T. et al., "Cell Sheet Engineering for Myocardial Tissue Reconstruction," *Biomaterials*, 2003; 24:2309-2316.

Shimizu, T. et al., "Fabrication of Pulsatile Cardiac Tissue Grafts Using a Novel 3-Dimensional Cell Sheet Manipulation Technique and Temperature-Responsive Cell Culture Surfaces," *Circulation Research*, 2002; 90:e40-e48.

Shuto, T. et al., "Dexamethasone Stimulates Osteoclast-Like Cell Formation by Inhibiting Granulocyte-Macrophage Colony-Stimulating Factor Production in Mouse Bone Marrow Cultures," *Endocrinology*, 1994; 134(3):1121-1126.

Siminoff, R. et al., "Properties of Reptilian Cutaneous Mechanoreceptors," *Exp. Neurol.*, 1968; 20:403-414.

Song, H. et al., "Astroglia Induce Neurogenesis From Adult Neural Stem Cells," *Nature*, 2002; 417:39-44.

Sordillo, L.M. et al., "Culture of Bovine Mammary Epithelial Cells in D-Valine Modified Medium: Selective Removal of Contaminating Fibroblasts," *Cell Biol. Int. Rep.*, 1988; 12(5): 354-365.

Street, C.N. et al., "Stem Cells: A Promising Source of Pancreatic Islets for Transplantation in Type 1 Diabetes," *Curr. Top Dev. Biol.*, 2003; 58:111-136.

Stroemer et al., "Enhanced Neocortical Neural Sprouting, Synaptogenesis, and Behavioral Recovery with D-Amphetamine Therapy after Neocortical Infarction in Rats," *Stroke*, 1998; 29:2381-2395.

Stroemer et al., "Neocortical Neural Sprouting, Synaptogenesis, and Behavioral Recovery After Neocortical Infarction in Rats," *Stroke*, 1995; 26:2135-2144.

Svendsen, C.N. "The Amazing Astrocyte," *Nature*, 2002; 417:29-32.

Svendsen, C.N. et al., "Long-Term Survival of Human Central Nervous System Progenitor Cells Transplanted Into a Rat Model of Parkinson's Disease," *Experim. Neurol.*, 1997; 148:135-146.

Swanson, R.A. et al., "A Semiautomated Method for Measuring Brain Infarct Volume," *J. Cereb. Blood Flow Metab.*, 1990; 10:290-293.

Swift, G.H. et al., "Tissue-Specific Expression of the Rat Pancreatic Elastase I Gene in Transgenic Mice," *Cell*, 1984; 38:639-646.

Szpak et al., "Border Zone Neovascularization in Cerebral Ischemic Infarct," *Folia Neuropathol*, 1999; 37(4):264-268. (Abstract only).

Taylor, D.A. et al., "Regenerating Functional Myocardium: Improved Performance After Skeletal Myoblast Transplantation," *Nature Medicine*, 1998; 4(8):929-1200.

Taylor, D.A. et al., "Cardiac Chimerism as a Mechanism for Self-Repair: Does It Happen and If so to What Degree?" *Circulation*, 2002; 106:2-4.

Thorsby, E. et al., "Role of HLA Molecules in the Induction of Alloimmune Responses: Clinical Significance in the Cyclosporine Era," *Transplant Proc.*, 2004; 36(Suppl 2S):16S-21S.

Timmermans, F. et al., "Stem Cells for the Heart, Are We There Yet?" *Cardiology*, 2003; 100(4):176-185.

Toma, C. et al., "Human Mesenchymal Stem Cells Differentiate to a Cardiomyocyte Phenotype in the Adult Murine Heart," *Circulation*, 2002; 105:93-98.

Tomita, M. et al., "Bone Marrow-Derived Stem Cells Can Differentiate Into Retinal Cells in Injured Rat Retina," *Stem Cells*, 2002; 20:279-283.

Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," Stem Cells, 2001; 19:408-418.

Tresco, P.A. et al., "Cellular Transplants as Sources for Therapeutic Agents," *Advanced Drug Delivery Reviews*, 2000; 42:3-27.

Turner, D., "The Human Leucocyte Antigen (HLA) System," *Vox Sang.*, 2004; 87(Suppl 1):S87-S90.

Turner, J.F., "Inherited Retinal Dystrophy in the RCS Rat: Prevention of Photoreceptor Degeneration by Pigment Epithelial Cell Transplantation," *Exp. Eye Res.*, 1988; 47:911-917.

Tusher, V.G. et al., "Significance Analysis of Microarrays Applied to the Ionizing Radiation Response," *PNAS*, 2001; 98(9):5116-5121.

Ujike, H. et al., "Gene Expression Related to Synaptogenesis, Neuritogenesis, and MAP Kinase in Behavioral Sensitization to Psychostimulants," *Ann. N. Y. Acad. Sci.*, 2002; 965:55-67.

Ulloa-Montoya, F. et al., "Culture Systems for Pluripotent Stem Cells," *Journal of Bioscience and Bioengineering*, 2005; 100(1):12-27.

"Unigene Entry for Hs.522632, Homo sapiens TMP Metallopeptidase Inhibitor 1 (TIMP1)," printed from http://www.ncbi.nlm.nih.gov/UniGene on Oct. 12, 2006.

Urbich, C. et al., "Endothelial Progenitor Cells Characterization and Role in Vascular Biology," *Circ. Res.*, 2004; 95:343-353.

Vajsar, J. et al., "Walker-Warburg Syndrome," *Orphanet Journal of Rare Diseases*, 2006; 1:29.

Van Hoffelen, S.J. et al., "Incorporation of Murine Brain Progenitor Cells Into the Developing Mammalian Retina," *Invest. Ophthalmol. Vis. Sci.*, 2003; 44(1):426-434.

Vassliopoulos, G. et al., "Transplanted Bone Marrow Regenerates Liver by Cell Fusion," *Nature*, 2003; 422:901-904.

Verma, I. M. et al., "Gene Therapy—Promises, Problems and Prospects," *Nature*, 1997; 389:239-242.

(56) References Cited

OTHER PUBLICATIONS

Vermot-Desroches, C. et al., "Heterogeneity of Antigen Expression Among Human Umbilical Cord Vascular Endothelial Cells: Identification of Cell Subsets by Co-Expression of Haemopoietic Antigens," *Immunol. Lett.*, 1995; 48:1-9.
Villegas-Perez, M.P. et al., "Influences of Peripheral Nerve Grafts on the Survival and Regrowth of Axotomized Retinal Ganglion Cells in Adult Rats," *J. Neurosci.*, 1988; 8(1):265-280.
Villegas-Perez, M.P. et al., "Rapid and Protracted Phases of Retinal Ganglion Cell Loss Follow Axotomy in the Optic Nerve of Adult Rats," *J. Neurobiology*, 1993; 24(1):23-36.
Von Koskull, H. et al., "Induction of Cytokeratin Expression in Human Mesenchymal Cells," *J. Cell Physiol.*, 1987; 133:321-329.
Walboomers, X .F. et al., "Cell and Tissue Behavior on Micro-Grooved Surfaces," *Odontology*, 2001; 89:2-11.
Walter, D. H. et al., "Statin Therapy Accelerates Reendothelialization a Novel Effect Involving Mobilization and Incorporation of Bone Marrow-Derived Endothelial Progenitor Cells," *Circulation*, 2002; 105:3017-3024.
Wang, D. et al., "Synthesis and Characterization of a Novel Degradable Phosphate-Containing Hydrogel," *Biomaterials*, 2003; 24:3969-3980.
Wang, X . et al., "Cell Fusion Is the Principal Source of Bone-Marrow-Derived Hepatocytes," *Nature*, 2003; 422:897-900.
Wegman, A. et al., "Nonsteroidal Anti-Inflammatory Drugs or Acetaminophen for Osteoarthritis of the Hip or Knee? A Synstematic Review of Evidence and Guidelines," *J. Rheumatol.*, 2004; 31(2):344-354.
Weiss, M.L. et al., "Transplantation of Porcine Umbilical Cord Matrix Cells Into the Rat Brain," *Exp. Neur.*, 2003; 182:288-299.
Weiss, M.L. et al., "Human Umbilical Cord Matrix Stem Cells: Preliminary Characterization and Effect of Transplantation in a Rodent Model of Parkinson's Disease," *Stem Cells*, 2006; 24:781-792.
Wenning, G.K. et al., "Neural Transplantation in Animal Models of Multiple System Atrophy: A Review," *J. Nueral Transm.*, 1999; Suppl.(55):103-113.
Williams, J.T. et al., "Cells Isolated From Adult Human Skeletal Muscle Capable of Differentiating Into Multiple Mesodermal Phenotypes," *Am. Surg.* 1999; 65(I):22-6.
Wobus, A.M. et al., "Retinoic Acid Accelerates Embryonic Stem Cell-Derived Cardiac Differentiation and Enhances Development of Ventricular Cardiomyocytes," *J. Mol. Cell Cardiol.*, 1997; 29:1525-1539.
Wolford, L.M. et al., "Considerations in Nerve Repair," *BUMC Proceedings*, 2003; 16(2):152-156.
Woodbury, D., et al., "Adult Rat and Human Bone Marrow Stromal Cells Differentiate Into Neurons," *J. Neurosci. Res.*, 2000; 61:364-370.
Wulf, G.G. et al., "Mesengenic Progenitor Cells Derived From Human Placenta," *Tissue Engineering*, 2004; 10(7/8):1136-1147.
Xi, G, et al., "Mechanisms of Edema Formation After Intracerebral Hemorrhage Effects of Extravasated Red Blood Cells on Blood Flow and Blood-Brain Barrier Integrity," *Stroke*, 2001; 32:2932-2938.
Xu, C. et al., "Characterization and Enrichment of Cardiomyocytes Derived From Human Embryonic Stem Cells," *Circ. Res.*, 2002; 91:501-508.
Xu, Y. et al., "Dopamine, In the Presence of Tyrosinase, Covalently Modifies and Inactivates Tyrosine Hydroxylase," *J. Neurosci. Res.*, 1998; 54:691-697.
Yamashima, T., "Implication of Cysteine Proteases Calpain, Cathepsin and Caspase in Ischemic Neuronal Death of Primates," *Progress in Neurobiology*, 2000; 62:273-295.
Yang, C. et al., "Enhancement of Neovascularization With Cord Blood CD133+Cell-Derived Endothelial Progenitor Cell Transplantation," *Thrombosis and Haemostasis*, 2004; 91:1202-1212.
Yang, H. et al., "Region-Specific Differentiation of Neural Tube-Derived Neuronal Restricted Progenitor Cells After Heterotopic Transplantation," *PNAS*, 2000; 97(24):13366-13371.

Ye Q. et al., "Recovery of Placental-Derived Adherent Cells With Mesenchymal Stem Cell Characteristics", *Blood*, 2001; 98(11 Part 2):147B (Abstract No. 4260).
Yip, H.K., et al., "Axonal Regeneration of Retinal Ganglion Cells: Effect of Trophic Factors," *Prog. Retin Eye Res.*, 2000; 19(5):559-575.
Yokoo, T. et al., "Stem Cell Gene Therapy for Chronic Renal Failure," *Curr Gene Ther.*, 2003; 3:387-394.
Yu, M. et al., "Mid-Trimester Fetal Blood-Derived Adherent Cells Share Characteristics Similar to Mesenchymal Stem Cells But Full-Term Umbilical Cord Blood Does Not," *British J. of Haematology*, 2004; 124:666-675.
Zangani, D. et al., "Multiple Differentiation Pathways of Rat Mammary Stromal Cells In Vitro: Acquisition of a Fibroblast, Adipocyte or Endothelial Phenotype Is Dependent on Hormonal and Extracellular Matrix Stimulation," *Differentiation*, 1999; 64:91-101.
Zhang, L. et al., "A Test for Detecting Long-Term Sensorimotor Dysfunction in the Mouse after Focal Cerebral Ischemia," *J. Neurosci. Methods*, 2002; 117:207-214.
Zhang, S. et al., "In Vitro Differentiation of Transplantable Neural Precursors From Human Embryonic Stem Cells," *Nature Biotechnology*, 2001; 19:1129-1133.
Zhang, X. et al., "Efficient Adeno-Associated Virus-Mediated Gene Expression in Human Placenta-Derived Mesenchymal Cells," *Microbiol. Immunol.*, 2003; 47(1):109-116.
Zhang, Y. et al., "Comparison of Mesenchymal Stem Cells from Human Placenta and Bone Marrow," *Chinese Medical Journal*, 2004; 117(6):882-887.
Zhang, Z.G. et al., "Correlation of VEGF and Angiopoietin Expression with Disruption of Blood-Brain Barrier and Angiogenesis after Focal Cerebral Ischemia," *J. Cereb. Blood Flow Metab.*, 2002; 22(4):379-392.
Zimmerman, S. et al., "Lack of Telomerase Activity in Human Mesenchymal Stem Cells," *Leukemia*, 2003; 17:1146-1149.
Zuloff-Shani, A. et al., "Macrophage Suspensions Prepared From a Blood Unit for Treatment of Refractory Human Ulcers," *Transfus. Apheresis Sci.*, 2004; 30:163-167.
Diller, G.P. et al., "Circulating Endothelial Progenitor Cells in Patents With Eisenmenger Syndrome and Idiopathic Pulmonary Arterial Hypertension," *Circulation*, 2008; 117:3020-3030.
Guerassimov, A. et al., "The Development of Emphysema in Cigarette Smoke-exposed Mice is Strain Dependent," *Am J Respir Grit Care Med.*, 2004; 170:974-980.
Ishizawa, K. et al., "Bone marrow-derived cells contribute to lung regeneration after elastase-induced pulmonary emphysema," FEBS Let., 2004: 556:249-252.
McNee, W., "Pathogenesis of Chronic Obstructive Pulmonary Disease," *Proc. Am Thorac.*, 2005; 2:258-266.
Ortiz, L.A. et al., "Interleukin 1 Receptor Antagonist Mediates the Antiinftammatory and Antifibrotic Effect of Mesenchymal Stem Cells During Lung Injury," *PNAS*, 2007; 104:11002-11007.
Ortiz, L.A. et al., "Mesenchymal stem cell engraftment in lung is enhanced in response to bleomycin exposure and ameliorates its fibrotic effects," *PNAS*, 2003; 100:8407-8411.
Patel, K.M. et al., "Mesenchymal Stem Cells Attenuate Hypoxic Pulmonary Vasoconstriction by a Paracrine Mechanism," *J Surg Res.*, 2007; 143:281-5.
Rojas, M. et al. "Bone Marrow-Derived Mesenchymal Stem Cells in Repair of the Injured Lung," *Am J Respir Cell Mol Biol.*, 2005; 33:145-152.
Spurzem, J.R. and Rennard, S.I., "Pathogenesis of COPD," *Semin Respir Care Med.* 2005; 26:142-143.
Weiss, D. J. et al. "Stem Cells and Cell Therapies in Lung Biology and Lung Diseases," Proc Am Thorac Soc., 2008; 5:637-667.
Yamada. M. et al., "Bone Marrow-Derived Progenitor Cells Are Important for Lung Repair after Lipopolysaccharide-Induced Lung Injury," *J Immunol.*, 2004; 172:1266-72: erratum *J Immunol.*, 2004:173-4755.
Yu. B. et al., "Acute Tobacco Smoke-Induced Airways Inflammation in Spontaneously Hypertensive Rats," *Inhal Toxicol.*, 2008:20:623-633.

(56) References Cited

OTHER PUBLICATIONS

Zhao, F. et al., "Therapeutic Effects of Bone Marrow-Derived Mesenchymal Stem Cells Engraftment on Bleomycin-induced Lung injury in Rats," *Transplantation Proceedings*, 2008, 40:1700-1705.
In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.
In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U. S. Patent and Trademark Office, Non-Final Office Action in re: U.S. Appl. No. 11/322,372 dated Sep. 3, 2008, 13 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
In the U. S. Patent and Trademark Office, Final Office Action in re: U.S. Appl. No. 11/315,898, dated Sep. 16, 2008, 8 pages.
In the U. S. Patent and Trademark Office, Non-Final Office Action, in re: U.S. Appl. No. 11/297,156, dated Oct. 10, 2008, 11 pages.
In the U. S. Patent and Trademark Office, Non-Final Office Action in re: U.S. Appl. No. 11/317,574, dated Sep. 30, 2008, 23 pages.
In the U. S. Patent and Trademark Office, Non-Final Office Action in re: U.S. Appl. No. 11/315,969, dated Dec. 23, 2008, 11 pages.
In the U. S. Patent and Trademark Office, Non-Final Office Action in re: U.S. Appl. No. 10/951,357, dated Nov. 26, 2008, 19 pages.
In the U. S. Patent and Trademark Office, Non-Final Office Action in re: U.S. Appl. No. 11/321,864, dated Jan. 8, 2009, 10 pages.
In the U. S. Patent and Trademark Office, Final Office Action in re: U.S. Appl. No. 11/321,863, dated Feb. 12, 2009, 15 pages.
In the U. S. Patent and Trademark Office, Non-Final Office Action in re: U.S. Appl. No. 11/315,943, dated Feb. 20, 2009, 9 pages.
In the U. S. Patent and Trademark Office, Non-Final Office Action in re: U.S. Appl. No. 10/877,445, dated Mar. 19, 2009, 15 pages.
In the U. S. Patent and Trademark Office, Non-Final Office Action in re: U.S. Appl. No. 11/481,481, dated Mar. 20, 2009, 12 pages.
In the U. S. Patent and Trademark Office, Final Office Action in re: U.S. Appl. No. 11/315,897, dated Mar. 20, 2009, 13 pages.
In the U. S. Patent and Trademark Office, Non-Final Office Action in re: U.S. Appl. No. 11/481,480, dated Mar. 20, 2009, 13 pages.
In the U. S. Patent and Trademark Office, Final Office Action in re: U.S. Appl. No. 11/322,003 dated Feb. 13, 2009, 17 pages.
In the U. S. Patent and Trademark Office, Final Office Action in re: U.S. Appl. No. 10/876,998 dated Feb. 13, 2009, 10 pages.
In the U. S. Patent and Trademark Office, Final Office Action in re: U.S. Appl. No. 11/322,372 dated Feb. 13, 2009, 14 pages.
In the U. S. Patent and Trademark Office, Non-Final Office Action in re: U.S. Appl. No. 11/315,898 dated Feb. 18, 2009, 10 pages.
In the U. S. Patent and Trademark Office, Non-Final Office Action in re: U.S. Appl. No. 11/304,091 dated Feb. 27, 2009, 11 pages.
In the U. S. Patent and Trademark Office, Non-Final Office Action in re: U.S. Appl. No. 11/481,456 dated Apr. 16, 2009, 14 pages.
In the U. S. Patent and Trademark Office, Non-Final Office Action in re: U.S. Appl. No. 11/317,574 dated Apr. 29, 2009, 21 pages.
In the U. S. Patent and Trademark Office, Advisory Action in re: U.S. Appl. No. 11/315,969 dated Sep. 29, 2009, 8 pages.
In the U. S. Patent and Trademark Office, Advisory Action in re: U.S. Appl. No. 11/322,372 dated May 12, 2009, 10 pages.
In the U. S. Patent and Trademark Office, Non-Final Office Action in re: U.S. Appl. No. 10/877,446 dated Jun. 12, 2009, 16 pages.
In the U. S. Patent and Trademark Office, Final Office Action in re: U.S. Appl. No. 11/322,372 dated Aug. 6, 2009, 12 pages.
In the U. S. Patent and Trademark Office, Final Office Action in re: U.S. Appl. No. 11/617,346 dated Aug. 11, 2009, 12 pages.
In the U. S. Patent and Trademark Office, Final Office Action in re: U.S. Appl. No. 11/481,456 dated Oct. 9, 2009, 11 pages.

(56) References Cited

OTHER PUBLICATIONS

In the U. S. Patent and Trademark Office, Final Office Action in re: U.S. Appl. No. 10/877,445 dated Aug. 25, 2009, 18 pages.
In the U. S. Patent and Trademark Office, Final Office Action in re: U.S. Appl. No. 11/321,863 dated Aug. 7, 2009, 11 pages.
In the U. S. Patent and Trademark Office, Final Office Action in re: U.S. Appl. No. 11/321,864 dated Aug. 17, 2009, 13 pages.
In the U. S. Patent and Trademark Office, Final Office Action in re: U.S. Appl. No. 11/315,969 dated May 13, 2009, 11 pages.
In the U. S. Patent and Trademark Office, Non-Final Office Action in re: U.S. Appl. No. 11/317,574 dated Dec. 28, 2009, 26 pages.
In the U. S. Patent and Trademark Office, Non-Final Office Action in re: U.S. Appl. No. 11/321,863 dated Jan. 7, 2010, 13 pages.
In the U. S. Patent and Trademark Office, Non-Final Office Action in re: U.S. Appl. No. 11/321,864 dated Jan. 27, 2010, 12 pages.
In the U. S. Patent and Trademark Office, Non-Final Office Action in re: U.S. Appl. No. 11/315,969 dated Jan. 27, 2010, 12 pages.
In the U. S. Patent and Trademark Office, Non-Final Office Action in re: U.S. Appl. No. 11/315,943 dated Feb. 19, 2010, 13 pages.
In the U. S. Patent and Trademark Office, Final Office Action in re: U.S. Appl. No. 11/316,104 dated Mar. 24, 2010, 12 pages.
In the U. S. Patent and Trademark Office, Non-Final Office Action in re: U.S. Appl. No. 11/481,456 dated May 14, 2010, 9 pages.
In the U. S. Patent and Trademark Office, Non-Final Office Action in re: U.S. Appl. No. 11/481,481 dated May 13, 2010, 9 pages.
In the U. S. Patent and Trademark Office, Final Office Action in re: U.S. Appl. No. 11/315,897 dated May 14, 2010, 13 pages.
In the U. S. Patent and Trademark Office, Non-Final Office Action in re: U.S. Appl. No. 11/481,480 dated May 17, 2010, 10 pages.
In the U. S. Patent and Trademark Office, Final Office Action in re: U.S. Appl. No. 10/877,445 dated Jul. 8, 2010, 20 pages.
In the U. S. Patent and Trademark Office, Final Office Action in re: U.S. Appl. No. 10/876,998 dated Aug. 3, 2010, 14 pages.
In the U. S. Patent and Trademark Office, Non-Final Office Action in re: U.S. Appl. No. 11/321,863 dated Aug. 17, 2010, 15 pages.
In the U. S. Patent and Trademark Office, Final Office Action in re: U.S. Appl. No. 11/617,346 dated Aug. 20, 2010, 12 pages.
In the U. S. Patent and Trademark Office, Final Office Action in re: U.S. Appl. No. 11/321,864 dated Aug. 31, 2010, 7 pages.
In the U. S. Patent and Trademark Office, Final Office Action in re: U.S. Appl. No. 11/315,969 dated Aug. 31, 2010, 6 pages.
In the U. S. Patent and Trademark Office, Final Office Action in re: U.S. Appl. No. 11/322,372 dated Aug. 31, 2010, 11 pages.
In the U. S. Patent and Trademark Office, Non-Final Office Action in re: U.S. Appl. No. 12/245,571 dated Sep. 15, 2010, 8 pages.
In the U. S. Patent and Trademark Office, Non-Final Office Action in re: U.S. Appl. No. 11/316,104 dated Sep. 21, 2010, 13 pages.
In the U. S. Patent and Trademark Office, Final Office Action in re: U.S. Appl. No. 11/317,574 dated Oct. 6, 2010, 16 pages.
In the U. S. Patent and Trademark Office, Non-Final Office Action in re: U.S. Appl. No. 12/054,718 dated Sep. 29, 2010, 18 pages.
In the U. S. Patent and Trademark Office, Non-Final Office Action in re: U.S. Appl. No. 11/322,372 dated Jan. 21, 2010, 10 pages.
In the U. S. Patent and Trademark Office, Final Office Action in re: U.S. Appl. No. 11/481,481 dated Sep. 18, 2009, 11 pages.
In the U. S. Patent and Trademark Office, Advisory Action in re: U.S. Appl. No. 11/315,897 dated Jun. 30, 2009, 3 pages.
In the U. S. Patent and Trademark Office, Non-Final Action in re: U.S. Appl. No. 11/315,897 dated Sep. 2, 2009, 12 pages.
In the U. S. Patent and Trademark Office, Final Action in re: U.S. Appl. No. 11/481,480 dated Sep. 17, 2009, 12 pages.
In the U. S. Patent and Trademark Office, Final Action in re: U.S. Appl. No. 10/877,446 dated Jun. 4, 2010, 17 pages.
In the U. S. Patent and Trademark Office, Final Action in re: U.S. Appl. No. 11/617,346 dated Apr. 15, 2010, 7 pages.
In the U. S. Patent and Trademark Office, Non-Final Action in re: U.S. Appl. No. 11/316,104 dated Oct. 31, 2008, 15 pages.
In the U. S. Patent and Trademark Office, Final Action in re: U.S. Appl. No. 10/876,998 dated May 27, 2009, 14 pages.
In the U. S. Patent and Trademark Office, Non-Final Action in re: U.S. Appl. No. 10/876,998 dated Nov. 24, 2009, 7 pages.
In the U. S. Patent and Trademark Office, Final Action in re: U.S. Appl. No. 11/322,003 dated Feb. 13, 2009, 17 pages.
In the U. S. Patent and Trademark Office, Non-Final Office Action in re: U.S. Appl. No. 12/337,439 dated Jan. 6, 2011, 11 pages.
In the U. S. Patent and Trademark Office, Non-Final Action in re: U.S. Appl. No. 10/876,998 dated Feb. 1, 2011, 11 pages.
In the U. S. Patent and Trademark Office, Non-Final Action in re: U.S. Appl. No. 11/481,456 dated Feb. 3, 2011, 10 pages.
In the U. S. Patent and Trademark Office, Non-Final Action in re: U.S. Appl. No. 11/481,481 dated Feb. 3, 2011, 10 pages.
In the U. S. Patent and Trademark Office, Non-Final Action in re: U.S. Appl. No. 12/389,305 dated Feb. 8, 2011, 14 pages.
In the U. S. Patent and Trademark Office, Non-Final Action in re: U.S. Appl. No. 11/481,480 dated Feb. 3, 2011, 10 pages.
In the U.S. Patent and Trademark Office, Final Office Action in re: U.S. Appl. No. 10/877,446 dated Nov. 2, 2011, 12 pages.
In the U.S. Patent and Trademark Office, Final Office Action in re: U.S. Appl. No. 12/389,305 dated Oct. 12, 2011, 12 pages.
In the U.S. Patent and Trademark Office, Final Office Action in re: U.S. Appl. No. 12/429,849 dated Mar. 20, 2012, 9 pages.
In the U. S. Patent and Trademark Office, Final Office Action in re: U.S. Appl. No. 11/481,456 dated Oct. 11, 2011, 6 pages.
In the U.S. Patent and Trademark Office, Non-Final Office Action in re: U.S. Appl. No. 12/697,081 dated Apr. 2, 2012, 8 pages.
In the U.S. Patent and Trademark Office, Non-Final Office Action in re: U.S. Appl. No. 13/605,716 dated Feb. 13, 2013, 13 pages.
Kavanagh, H. et al.,"Allogeneic mesenchymal stem cells prevent allergic airway inflammation by inducing murine regulatory T cells," *Allergy*, 2001; 66(4):523-31.
Lee, O. et al., "Isolation of Multipotent Mesenchymal Stem Cells from Umbilical Cord Blood," *Blood*, 2004; 103:1669-1675.
Siafakas, N.M. and Tzortzaki, E.G., "Few Smokers Develop COPD. Why?", *Respir Med.*, 2005; 96:615-624.
Wang, Y.et al "Enhanced Recovery of Hematopoietic Progenitor and Stem Cells from Cultivated, Postpartum Human Placenta," Blood, 2001; 98(11): 183a (Abstract 769).
Beeres, S.L. et al., "Sustained effect of autologous bone marrow mononuclear cell injection in patients with refractory angina pectoris and chronic myocardial ischemia: twelve-month follow-up results." *Am Heart J.*, 2006; 152:684.e11-6.
Borlongan, C.V. et al., "Upregulation of CNS trophic factors by human umbilical cord transplant is essential for neuroprotection against acute stroke," Society for Neuroscience Abstract, 2003, Presentation No. 789.17.
Caplan, A. I. et al., "Mesenchymal Stem Cells as Trophic Mediators," *J Cell Biochem.*, 2006; 98:1076-84.
Capoccia, B. J. et al, "Bone Marrow-Derived Aldehyde Dehdrogenase Expressing Cells Possess Endothelial Progenitor Function in Addition to Hematopoietic Repopulating Ability and Aid in Blood Flow Recovery after Acute Ischemic Injury," *Blood*, 2005; 106(11): 747A, Abstract No. 2663.
Cho, H. J. et al, "Regulation of endothelial cell and endothelial progenitor cell survival and vasculogenesis by integrin-linked kinase," *Arteriosder Thromb Vasc Biol*, 2005; 25: 1154-60.
English, K. et al., "Murine mesenchymal stem cells suppress dendritic cell migration, maturation and antigen presentation", *Immunol Lett.*, 2008;115(1):50-8.
Garbuzova-Davis, S. et al., "Human Umbilical Cord Blood Treatment in a Model of ALS: Optimization of Cell Dose," PLoS ONE, 2008; 3(6): e2494.
Lu, F-Z et al., "Characterization and gene transfer in mesenchymal stem cells derived from human umbilical-cord blood," *J. Lab Clin. Med.*, 2005; 146:271-278.
Murohara, T., "Therapeutic vasculogenesis using human cord blood—derived endothelial progenitors," *Trends Cardiovasc Med*, 2001; 11: 303-307.
Piscaglia, A.C. et al., "Human Cordonal Stem Cell Intraperitoneal Injection Can Represent a Rescue Therapy After an Acute Hepatic Damage in Immunocompetent Rats," *Transplantation Proceedings*, 2005; 37,2711-2714.

(56) References Cited

OTHER PUBLICATIONS

Zhang, Y. et al., "Human placenta-derived mesenchymal progenitor cells support culture expansion of long-term culture-initiating cells from cord blood CD34+ cells," *Exp Hematol*, 2004; 32: 657-64.
In the U.S. Patent and Trademark Office, Non-Final Office Action in re: U.S. Appl. No. 11/317,574 dated Jul. 11, 2013, 29 pages.
Montemurro, T. et al., "Perivascular Human Umbilical Cord Cells Are Capable of Long Term Culture and Respond to Chemotactic Gradient in an In Vitro-Model of Alveolar Damage," *Blood (ASH Annual Meeting Abstracts)*, 2006: 108: Abstract 1687.
In the U.S. Patent and Trademark Office, Non-Final Office Action in re: U.S. Appl. No. 13/471,095 dated Nov. 29, 2013, 15 pages.
In the U.S. Patent and Trademark Office, Non-Final Office Action in re: U.S. Appl. No. 11/322,372 dated Jan. 16, 2014, 17 pages.
In the U.S. Patent and Trademark Office, Non-Final Office Action in re: U.S. Appl. No. 11/321,864 dated Jan. 29, 2014, 9 pages.
In the U.S. Patent and Trademark Office, Non-Final Office Action in re: U.S. Appl. No. 11/321,863 dated Jan. 31, 2014, 17 pages.
In the U.S. Patent and Trademark Office, Final Office Action in re: U.S. Appl. No. 11/317,574 dated Feb. 3, 2014, 16 pages.
In the U. S. Patent and Trademark Office, Non-Final Office Action in re: U.S. Appl. No. 10/876,998 dated Feb. 11, 2014, 14 pages.
In the U.S. Patent and Trademark Office, Non-Final Office Action in re: U.S. Appl. No. 12/389,305 dated Mar. 6, 2014, 37 pages.
In the U. S. Patent and Trademark Office, Non-Final Office Action in re: U.S. Appl. No. 11/316,104 dated Mar. 14, 2014, 11 pages.
In the U.S. Patent and Trademark Office, Non-Final Office Action in re: U.S. Appl. No. 12/389,305 dated Mar. 21, 2014, 47 pages.
In the U.S. Patent and Trademark Office, Non-Final Office Action in re: U.S. Appl. No. 10/877,446 dated Mar. 21, 2014, 21 pages.
In the U.S. Patent and Trademark Office, Non-Final Office Action in re: U.S. Appl. No. 11/316,104 dated Mar. 21, 2014, 20 pages.
In the U.S. Patent and Trademark Office, Non-Final Office Action in re: U.S. Appl. No. 11/315,969 dated Mar. 21, 2014, 15 pages.
In the U.S. Patent and Trademark Office, Final Office Action in re: U.S. Appl. No. 13/471,095 dated Apr. 7, 2014 15 pages.
Baksh, D. et al., "Comparison of proliferative and multilineage differentiation potential of human mesenchymal stem cells derived from umbilical cord and bone marrow." *Stem Cells*, 2007; 25: 1384-1392.
Bhatia, R. et al., "A clinically suitable ex vivo expansion culture system for LTC-IC and CFC using stroma-conditioned medium," *Exp Hematol.*, 1997;25(9):980-91 (Abstract only).
Cai, J. et al., "Stem cell and precursor cell therapy," *NeuroMolecular Medicine*, 2002; 3:233-249.
Ciavarella, S. et al., "Umbilical Cord Mesenchymal Stem Cells: Role of Regulatory Genes in Their Differentiation to Osteoblasts," *Stem Cells and Development*, 2009; 18:1211-1220.
Covas, D.T. et al., "Isolation and culture of umbilical vein mesenchymal stem cells." *Brazilian Journal of Medical and Biological Research*, 2003; 36: 1179-1183.
Deans, R.J. et al., "Mesenchymal stem cells: Biology and potential clinical uses," *Experimental Hematology*, 2000; 28: 875-884.
Henderson, GI, et al., "Inhibition of Placental Valine Uptake after Acute and Chronic Maternal Ethanol Consumption", *J Pharmacol Exp Therap*, 1981; 216:465-472.
Kestendjieva, S. et al., "Characterization of mesenchymal stem cells isolated from the human umbilical cord." *Cell Biology International*, 2008; 32: 724-732.
Li J. et al., "Human umbilical cord mesenchymal stem cells reduce systemic inflammation and attenuate LPS-induced acute lung injury in rats", *J. Inflamm (Lond)*, 2012; 9:33.
Lonza (Cambrex), hMSC Human Mesenchymal Stem Cells, Lonza, 2014, http://www.lonza.com/products-services/bio-research/primary-and-stem-cells/adult-stem-cells-and-media/hmsc-mesenchymal-stem-cells.aspx; accessed Jan. 31, 2014.
Nehlin et al., "Immunogenicity and Immune-Modulating Properties of Human Stem Cells", *Stem Cells in Clinical Research*, 2011.
Weiss D. J., "Stem cells and cell therapies for cystic fibrosis and other lung diseases," *Pulm Pharmacol Ther.*, 2008; 21: 588-94.
Weiss, D. J. et al. "Stem Cells and Cell Therapies in Lung Biology and Lung Diseases," *Proc Am Thorac Soc*, 2011; 8:223-272.
European Search Report (Communication pursuant to Article 94(3) EPC) dated Aug. 6, 2014 in counterpart European Application No. 09796901.8.
Lund, R.D. et al., "Cell Isolated from Umbilical Cord Tissue Rescue Photoreceptors and Visual Functions in a Rodent Model of Retinal Disease," *Stem Cells*, 2007; 25:602-611.
Rachakatla, R. S. et al., "Development of Human Umbilical Cord Matrix Stem Cell-Based Gene Therapy for Experimental Lung Tumors," *Cancer Gene Therapy*, 2007; 14:828-835.
Secco, M. et al., "Multipotent Stem Cells from Umbilical Cord: Cord is Richer than Blood!" *Stem Cells*, 2008; 26:146-150.
Troyer, D. L. et al., "Concise Review: Wharton's Jelly-Derived Cells Are a Primitive Stromal Cell Population," *Stem Cells*, 2008; 26:591-599.
In the U.S. Patent and Trademark Office, Final Office Action in re: U.S. Appl. No. 12/642,773 dated Aug. 6, 2014, 19 pages.
In the U.S. Patent and Trademark Office, Final Office Action in re: U.S. Appl. No. 12/389,305 dated Aug. 6, 2014, 57 pages.
In the U.S. Patent and Trademark Office, Non-Final Office Action in re: U.S. Appl. No. 11/611,602 dated Oct. 9, 2014, 15 pages.
In the U.S. Patent and Trademark Office, Final Office Action in re: U.S. Appl. No. 11/317,574 dated Feb. 3, 2014, 12 pages.
In the U.S. Patent and Trademark Office, Final Office Action in re: U.S. Appl. No. 11/321,864 dated Nov. 3, 2014, 10 pages.
Mattsson, J. et al. "Graft Failure after Allogenic Hematopoietic Cell Transplantation," *Biol Blood Marrow Transplant*, 2008; 14 (Supplement 1): 165-170.
Mineo, D. et al., "Combined Islet and Hematopoietic Stem Cell Allotransplantation: A Clinical Pilot Trial to Induce Chimerism and Graft Tolerance,"*American Journal of Transplantation*, 2008; 8:1262-1274.
Solomon, D. E., "An in vitro examination of extracellular matrix scaffold for use in wound healing," *Int. J. Path*, 2002, 93: 209-216.
In the U.S. Patent and Trademark Office Final Office Action in re: U.S. Appl. No. 10/876,998 dated Dec. 16, 2014, 19 pages.
In the U.S. Patent and Trademark Office, Non-Final Office Action in re: U.S. Appl. No. 13/471,095 dated Dec. 31, 2014, 13 pages.
In the U.S. Patent and Trademark Office, Non-Final Office Action in re: U.S. Appl. No. 11/322,372 dated Nov. 25, 2014, 24 pages.
In the U.S. Patent and Trademark Office, Final Office Action in re: U.S. Appl. No. 11/315,969 dated Dec. 18, 2014, 30 pages.
In the U.S. Patent and Trademark Office, Final Office Action in re: U.S. Appl. No. 11/321,863 dated Jan. 31, 2014, 17 pages.
In the U.S. Patent and Trademark Office, Non-Final Office Action in re: U.S. Appl. No. 14/152,649 dated Feb. 26, 2015, 9 pages.
In the U.S. Patent and Trademark Office, Non-Final Office Action in re: U.S. Appl. No. 14/444,689 dated Mar. 24, 2015, 9 pages.
In the U.S. Patent and Trademark Office, Final Office Action in re: U.S. Appl. No. 11/317,574 dated Apr. 1, 2015, 12 pages.
In the U.S. Patent and Trademark Office, Final Office Action in re: U.S. Appl. No. 14/152,649 dated Jul. 10, 2015, 7 pages.
In the U.S. Patent and Trademark Office, Non-Final Office Action in re: U.S. Appl. No. 10/877,446 dated Sep. 3, 2015, 82 pages.
In the U.S. Patent and Trademark Office, Non-Final Office Action in re: U.S. Appl. No. 11/321,864 dated Sep. 2, 2015, 11 pages.
In the U.S. Patent and Trademark Office, Non-Final Office Action in re: U.S. Appl. No. 12/389,305 dated Sep. 4, 2015, 63 pages.
In the U.S. Patent and Trademark Office, Non-Final Office Action in re: U.S. Appl. No. 11/316,104 dated Sep. 8, 2015, 63 pages.
Broxmeyer, H.E. et al., "Growth characteristics and expansion of human umbilical cord blood and estimation of its potential for transplantation in adults," *PNAS*, 1992; 89(9): 4109-4113.
Chen, K. et al., "Human umbilical cord mesenchymal stem cells hUC-MSCs exert immunosuppressive activities through a PGE2-dependent mechanism," *Clinical Immunology*, 2010, 135; 448-458.
Hass, R. et al., "Different populations and sources of human mesenchymal stem cells (MSC): A comparison of adult and neonatal tissue-derived MSC," *Cell Communication and Signaling*, 2011; 9:12, p. 1-14.
Ho, A.D. et al., "Heterogeneity of mesenchymal stromal cell preparations," *Cytotherapy*, 2008;10(4):320-30.

(56) References Cited

OTHER PUBLICATIONS

Kern, S. et al., "Comparative analysis of mesenchymal stem cells from bone marrow, umbilical cord blood, or adipose tissue," *Stem Cells*, 2006; 24(5):1294-301.
Leventhal, C. et al., "Endothelial trophic support for neuronal production and recruitment from the adult mammalian subependyma," *Molecular and Cellular Neuroscience*, 1999; 13; 450-464.
Otsuka, A. et al., "Lipopolysaccharide augments HLA-A,B,C molecule expression but inhibits interferon-gamma-induced HLA-DR molecule expression on cultured human endothelial cells,"*Immunology*, 1991; 73; 428-432.
Park, B-G et al., "Development of high density mammalian cell culture system for the production of tissue-type plasminogen activator," *Biotechnology and Bioprocess Engineering*, 2000; 5:123-129.
Pittenger, M.F. et al., "Human mesenchymal stem cells: progenitor cells for cartilage, bone, fat and stroma," *Current Topics in Microbiology and Immunology*, 2000; 251:3-11.
Xu, Y et al., "Umbilical Cord-Derived Mesenchymal Stem Cells Isolated by a Novel Explantation Technique Can Differentiate into Functional Endothelial Cells and Promote Revascularization," *Stem Cells and Development*, 2010, 19(10): 1511-1522.
In the U.S. Patent and Trademark Office Non-Final Office Action in re: U.S. Appl. No. 14/152,649 dated Oct. 27, 2015, 7 pages.
In the U.S. Patent and Trademark Office, Final Office Action in re: U.S. Appl. No. 10/876,998 dated Dec. 22, 2015, 21 pages.
In the U.S. Patent and Trademark Office, Final Office Action in re: U.S. Appl. No. 11/321,864 dated Dec. 22, 2015, 15 pages.
In the U.S. Patent and Trademark Office, Non-Final Office Action in re: U.S. Appl. No. 11/317,574 dated Jan. 6, 2015, 11 pages.
In the U.S. Patent and Trademark Office, Final Office Action in re: U.S. Appl. No. 11/322,372 dated Jan. 6, 2015, 27 pages.
In the U.S. Patent and Trademark Office, Final Office Action in re: U.S. Appl. No. 13/471,095 dated Jun. 12, 2015, 10 pages.
Cho, S. et al., "Enhancement of Angiogenic Efficacy of Human Cord Blood Cell Transplantation," *Tissue Engineering*, 2006; 12:6 1651-1661.
Kim, E.S. et al., "Intratracheal transplantation of human umbilical cord blood-derived mesenchymal stem cells attenuates *Escherichia coli*-induced acute lung injury in mice," *Respiratory Research*, 2011, 12:108.
In the U.S. Patent and Trademark Office, Final Office Action in re: U.S. Appl. No. 13/471,095 dated Nov. 17, 2015, 16 pages.
In the U.S. Patent and Trademark Office, Non-Final Office Action in re: U.S. Appl. No. 13/471,095 dated Mar. 22, 2016, 17 pages.
In the U. S. Patent and Trademark Office, Final Office Action in re: U.S. Appl. No. 12/337,439 dated Mar. 17, 2016 29 pages.
In the U. S. Patent and Trademark Office, Final Office Action in re: U.S. Appl. No. 11/315,969 dated Apr. 21, 2016 20 pages.
In the U. S. Patent and Trademark Office, Non-Final Office Action in re: U.S. Appl. No. 14/705,680 dated May 19, 2016 68 pages.
In the U.S. Patent and Trademark Office, Final Office Action in re: U.S. Appl. No. 10/876,998 dated May 20, 2016, 21 pages.
In the U. S. Patent and Trademark Office, Final Office Action in re: U.S. Appl. No. 12/389,305 dated May 24, 2016 21 pages.
In the U.S. Patent and Trademark Office, Final Office Action in re: U.S. Appl. No. 11/316,104 dated May 24, 2016, 24 pages.
In the U. S. Patent and Trademark Office, Non-Final Office Action in re: U.S. Appl. No. 10/877,446 dated May 24, 2016 36 pages.
In the U.S. Patent and Trademark Office, Non-Final Office Action in re: U.S. Appl. No. 11/322,372 dated May 31, 2016, 29 pages.
In the U.S. Patent and Trademark Office, Final Office Action in re: U.S. Appl. No. 11/317,574 dated May 31, 2016, 18 pages.
Baksh, D. et al.,"Adult mesenchymal stem cells: characterization, differentiation, and application in cell and gene therapy", *J Cell Mol Med.*, 2004; 8(3):301-16.
Gupta, N. et al., "Intrapulmonary Delivery of Bone Marrow-Derived Mesenchymal Stem Cells Improves Survival and Attenuates Endotoxin-Induced Acute Lung Injury in Mice," *J Immunol*, 2007; 179:1855-1863.
Lu, LL et al., "Isolation and characterization of human umbilical cord mesenchymal stem cells with hematopoiesis-supportive function and other potentials," *Haematologica*, 2006; 91(8):1017-26.
Mankikar, S.D., "Stem Cells: A New Paradigm in Medical Therapeutics," *Journal of Long-Term Effects of Medical Implants*, 2010; 20:219-250.
Matute-Bello, G. et al., "Animal models of acute lung injury", *Am J Physiol Lung Cell Mol Physiol*, 2008 295: L379-L399.
Ruan, D. et al., "Differentiation of human Wharton's jelly cells toward nucleus pulposus-like cells after coculture with nucleus pulposus cells in vitro," *Tissue Eng Part A.*, 2012;18(1-2):167-75 (Abstract only).
In the U.S. Patent and Trademark Office, Final Office Action in re: U.S. Appl. No. 14/152,649 dated Jun. 14, 2016, 6 pages.
In the U.S. Patent and Trademark Office, Final Office Action in re: U.S. Appl. No. 11/617,346 dated Jun. 22, 2016, 25 pages.
In the U.S. Patent and Trademark Office, Final Office Action in re: U.S. Appl. No. 13/111,933 dated Jul. 6, 2016, 26 pages.
In the U.S. Patent and Trademark Office, Final Office Action in re: U.S. Appl. No. 11/317,574 dated Jul. 7, 2016, 9 pages.
In the U.S. Patent and Trademark Office, Final Office Action in re: U.S. Appl. No. 13/722,849 dated Jul. 28, 2016, 18 pages.
Naughton, B.A. et al., "Hematopoiesis on nylon mesh templates. I. Long-term culture of rat bone marrow cells," *Journal of Medicine*, 1987; 18(3-4):219-50.
Wakitani, S. et al., "Mesenchymal cell-based repair of large, full-thickness defects of articular cartilage", *J Bone Joint Surg Am*, 1994; 76(4): 579-592.
Zhao, Q.H. et al., "Biological characteristics of human umbilical cord-derived mesenchymal stem cells and their differentiation into chondrogenic and osteogenic cells," *Zhonghua Yi Xue Za Zhi.*, 2011; 91(5):317-21 (Abstract only).

* cited by examiner

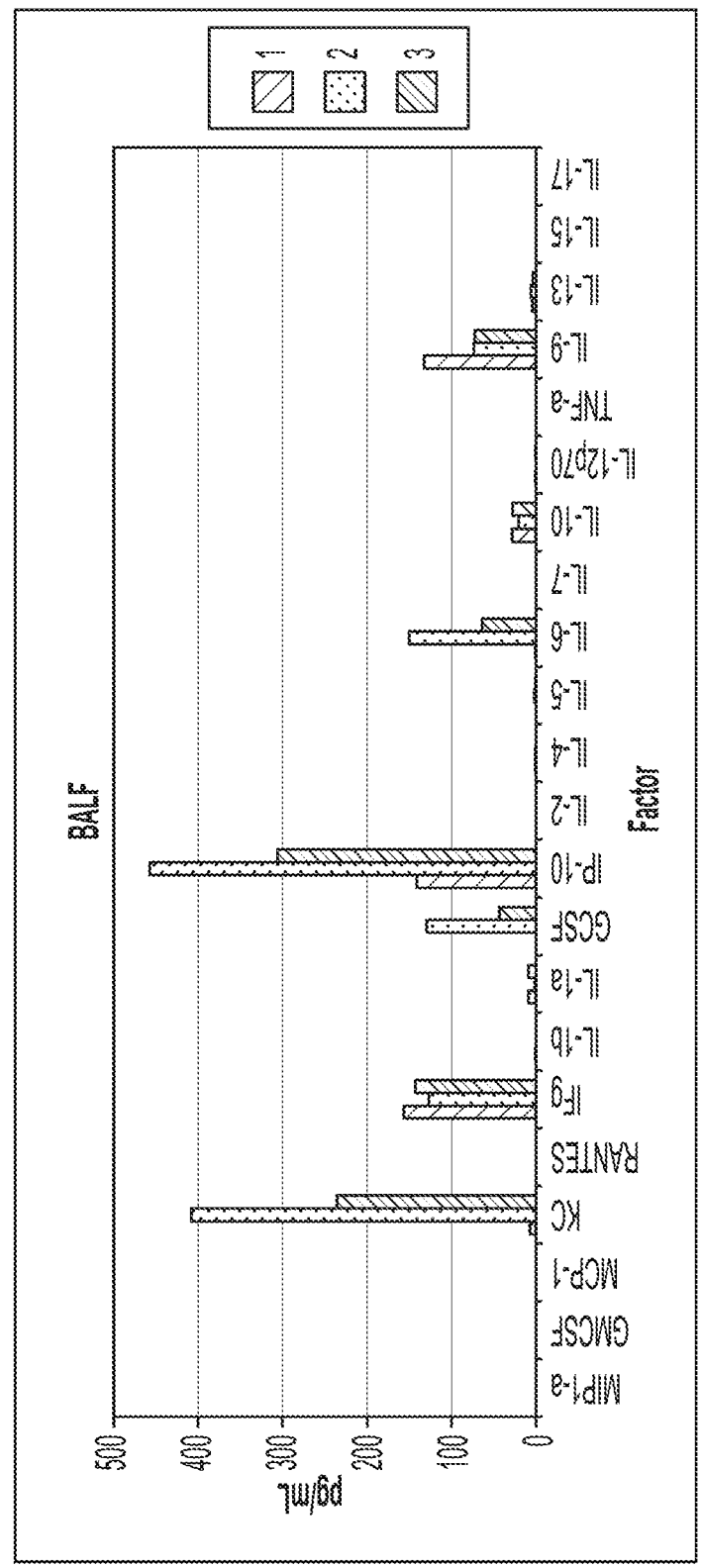

Figure 3

| Lung Homogenate | | | | | | | | | | | | | | | | | | | | | | | | | |
|---|---|---|---|---|---|---|---|---|---|---|---|---|---|---|---|---|---|---|---|---|---|---|---|---|---|
| Treatment group | Animal number | MIP1-a | GMCSF | MCP-1 | KC | RANTES | IFg | IL-1b | IL-1a | GCSF | IP-10 | IL-2 | IL-4 | IL-5 | IL-6 | IL-7 | IL-10 | IL-12p70 | TNF-a | IL-9 | IL-13 | IL-15 | IL-17 |
| 1 | 1 | 0 | 0 | 0 | 53 | 36 | 52 | 22 | 0 | 6 | 840 | 0 | 1 | 11 | 1 | 0 | 27 | 9 | 0 | 82 | 8 | 0 | 0 |
| 1 | 2 | 0 | 0 | 0 | 77 | 18 | 76 | 17 | 10 | 6 | 720 | 0 | 1 | 7 | 8 | 0 | 46 | 18 | 0 | 113 | 14 | 27 | 0 |
| 1 | 3 | 0 | 0 | 0 | 45 | 24 | 59 | 14 | 29 | 4 | 524 | 9 | 1 | 12 | 5 | 0 | 31 | 15 | 0 | 82 | 10 | 0 | 0 |
| 1 | 4 | 0 | 0 | 0 | 67 | 28 | 58 | 31 | 34 | 7 | 621 | 9 | 1 | 16 | 9 | 16 | 51 | 18 | 0 | 135 | 11 | 22 | 0 |
| 1 | 5 | 0 | 0 | 0 | 101 | 14 | 83 | 20 | 0 | 6 | 824 | 25 | 1 | 15 | 34 | 0 | 42 | 23 | 0 | 105 | 22 | 24 | 4 |
| 1 | 6 | 0 | 0 | 0 | 66 | 32 | 63 | 14 | 198 | 7 | 755 | 16 | 1 | 17 | 14 | 0 | 37 | 24 | 0 | 100 | 15 | 28 | 0 |
| Mean: | | 0 | 0 | 0 | 68 | 25 | 65 | 20 | 45 | 6 | 714 | 10 | 1 | 13 | 12 | 3 | 39 | 18 | 0 | 103 | 13 | 17 | 1 |
| StdDev: | | 0 | 0 | 0 | 20 | 9 | 12 | 6 | 76 | 1 | 122 | 10 | 0 | 4 | 12 | 6 | 9 | 6 | 0 | 20 | 5 | 13 | 1 |
| 2 | 1 | 0 | 0 | 139 | 149 | 9 | 70 | 13 | 37 | 23 | 1315 | 8 | 1 | 30 | 69 | 0 | 39 | 12 | 0 | 96 | 18 | 0 | 0 |
| 2 | 2 | 0 | 0 | 526 | 555 | 4 | 51 | 4 | 18 | 171 | 1146 | 5 | 1 | 13 | 448 | 0 | 20 | 0 | 0 | 62 | 7 | 0 | 0 |
| 2 | 3 | 0 | 0 | 111 | 103 | 9 | 62 | 24 | 56 | 8 | 712 | 7 | 1 | 14 | 33 | 0 | 37 | 4 | 0 | 82 | 8 | 0 | 0 |
| 2 | 4 | 0 | 0 | 143 | 322 | 0 | 34 | 8 | 9 | 59 | 503 | 0 | 1 | 11 | 91 | 0 | 26 | 4 | 0 | 63 | 6 | 0 | 0 |
| 2 | 5 | 0 | 0 | 143 | 334 | 7 | 68 | 11 | 28 | 20 | 1783 | 8 | 1 | 11 | 47 | 0 | 30 | 4 | 0 | 106 | 8 | 28 | 0 |
| 2 | 6 | 0 | 0 | 295 | 303 | 4 | 39 | 9 | 11 | 75 | 619 | 4 | 1 | 11 | 121 | 0 | 27 | 5 | 0 | 54 | 0 | 0 | 0 |
| Mean: | | 0 | 0 | 226 | 294 | 5 | 54 | 11 | 27 | 59 | 1013 | 5 | 1 | 15 | 135 | 0 | 30 | 5 | 0 | 77 | 8 | 5 | 0 |
| StdDev: | | 0 | 0 | 161 | 160 | 4 | 15 | 7 | 18 | 60 | 492 | 3 | 0 | 7 | 156 | 0 | 7 | 4 | 0 | 21 | 6 | 11 | 0 |
| 3 | 1 | 0 | 0 | 0 | 115 | 7 | 50 | 16 | 30 | 16 | 1121 | 8 | 1 | 15 | 31 | 0 | 34 | 15 | 0 | 79 | 15 | 0 | 0 |
| 3 | 2 | 0 | 0 | 0 | 163 | 11 | 50 | 9 | 38 | 20 | 1105 | 8 | 1 | 16 | 36 | 0 | 28 | 6 | 0 | 65 | 9 | 0 | 0 |
| 3 | 3 | 0 | 0 | 0 | 157 | 13 | 56 | 7 | 25 | 24 | 1465 | 7 | 1 | 16 | 53 | 0 | 36 | 9 | 0 | 68 | 9 | 0 | 0 |
| 3 | 4 | 0 | 0 | 0 | 161 | 16 | 59 | 8 | 24 | 12 | 1647 | 7 | 1 | 14 | 26 | 0 | 24 | 5 | 0 | 90 | 12 | 21 | 0 |
| 3 | 5 | 0 | 0 | 0 | 337 | 7 | 41 | 16 | 26 | 49 | 711 | 8 | 2 | 13 | 64 | 0 | 25 | 13 | 0 | 60 | 6 | 0 | 0 |
| 3 | 6 | 0 | 0 | 88 | 318 | 17 | 40 | 9 | 15 | 45 | 1839 | 8 | 1 | 14 | 84 | 0 | 24 | 11 | 0 | 73 | 6 | 3 | 0 |
| Mean: | | 0 | 0 | 15 | 209 | 12 | 49 | 11 | 27 | 27 | 1315 | 8 | 1 | 15 | 49 | 0 | 29 | 10 | 0 | 72 | 10 | 8 | 0 |
| StdDev: | | 0 | 0 | 36 | 94 | 4 | 8 | 4 | 8 | 15 | 413 | 1 | 0 | 1 | 22 | 0 | 5 | 4 | 0 | 11 | 4 | 8 | 0 |
| t-test | | nd | nd | 0.02 | 0.26 | 0.08 | 0.57 | 0.86 | 1.00 | 0.28 | 0.45 | 0.10 | 0.18 | 0.96 | 0.25 | nd | 0.63 | 0.01 | nd | 0.68 | 0.31 | 0.86 | nd |

Figure 4

BALF

| Treatment group | Animal number | MIP1-a | GMCSF | MCP-1 | KC | RANTES | IFg | IL-1b | IL-1a | GCSF | IP-10 | IL-2 | IL-4 | IL-5 | IL-6 | IL-7 | IL-10 | IL-12p70 | TNF-a | IL-9 | IL-13 | IL-15 | IL-17 |
|---|---|---|---|---|---|---|---|---|---|---|---|---|---|---|---|---|---|---|---|---|---|---|---|
| 1 | 1 | 0 | 0 | 0 | 8 | 0 | 162 | 0 | 8 | 0 | 113 | 0 | 0 | 0 | 1 | 0 | 39 | 0 | 0 | 63 | 6 | 0 | 0 |
| 1 | 2 | 0 | 0 | 0 | 8 | 0 | 174 | 0 | 15 | 0 | 195 | 0 | 0 | 0 | 1 | 0 | 19 | 0 | 0 | 170 | 4 | 0 | 0 |
| 1 | 3 | 0 | 0 | 0 | 7 | 0 | 131 | 0 | 0 | 0 | 95 | 0 | 0 | 0 | 0 | 0 | 26 | 0 | 0 | 82 | 0 | 0 | 0 |
| 1 | 4 | 0 | 0 | 0 | 8 | 0 | 195 | 4 | 9 | 0 | 176 | 0 | 0 | 0 | 1 | 0 | 35 | 4 | 0 | 175 | 5 | 0 | 0 |
| 1 | 5 | 0 | 0 | 0 | 12 | 0 | 197 | 0 | 14 | 0 | 216 | 0 | 0 | 0 | 1 | 0 | 39 | 0 | 0 | 221 | 6 | 0 | 0 |
| 1 | 6 | 0 | 0 | 0 | 0 | 0 | 79 | 0 | 6 | 0 | 53 | 0 | 0 | 0 | 1 | 0 | 11 | 0 | 0 | 82 | 4 | 0 | 0 |
| Mean: | | 0 | 0 | 0 | 7 | 0 | 156 | 1 | 9 | 0 | 141 | 0 | 0 | 0 | 1 | 0 | 28 | 1 | 0 | 132 | 4 | 0 | 0 |
| StdDev: | | 0 | 0 | 0 | 4 | 0 | 45 | 2 | 6 | 0 | 64 | 0 | 0 | 0 | 0 | 0 | 11 | 1 | 0 | 65 | 2 | 0 | 0 |
| 2 | 1 | 0 | 0 | 0 | 276 | 0 | 101 | 0 | 0 | 59 | 351 | 0 | 0 | 4 | 24 | 0 | 14 | 0 | 0 | 41 | 4 | 0 | 0 |
| 2 | 2 | 0 | 0 | 0 | 425 | 0 | 127 | 0 | 0 | 65 | 381 | 0 | 0 | 0 | 36 | 0 | 24 | 0 | 0 | 46 | 5 | 0 | 0 |
| 2 | 3 | 0 | 0 | 0 | 390 | 0 | 183 | 0 | 7 | 64 | 435 | 0 | 1 | 0 | 27 | 0 | 35 | 0 | 0 | 102 | 7 | 0 | 0 |
| 2 | 4 | 0 | 0 | 0 | 533 | 0 | 107 | 0 | 0 | 284 | 453 | 0 | 0 | 4 | 384 | 0 | 14 | 0 | 0 | 49 | 0 | 0 | 0 |
| 2 | 5 | 0 | 0 | 0 | 322 | 0 | 140 | 0 | 0 | 70 | 568 | 0 | 0 | 0 | 84 | 0 | 23 | 0 | 0 | 84 | 11 | 0 | 0 |
| 2 | 6 | 0 | 0 | 0 | 501 | 0 | 104 | 0 | 1 | 234 | 554 | 0 | 0 | 4 | 347 | 0 | 13 | 0 | 0 | 121 | 7 | 0 | 0 |
| Mean: | | 0 | 0 | 0 | 408 | 0 | 127 | 0 | 1 | 129 | 457 | 0 | 0 | 2 | 150 | 0 | 21 | 0 | 0 | 74 | 6 | 0 | 0 |
| StdDev: | | 0 | 0 | 0 | 100 | 0 | 31 | 0 | 3 | 102 | 89 | 0 | 0 | 2 | 169 | 0 | 9 | 0 | 0 | 34 | 4 | 0 | 0 |
| 3 | 1 | 0 | 0 | 0 | 175 | 0 | 151 | 0 | 6 | 50 | 346 | 0 | 0 | 0 | 67 | 0 | 32 | 0 | 0 | 60 | 0 | 0 | 0 |
| 3 | 2 | 0 | 0 | 0 | 256 | 0 | 108 | 0 | 5 | 45 | 201 | 0 | 0 | 0 | 33 | 0 | 23 | 4 | 0 | 41 | 4 | 0 | 0 |
| 3 | 3 | 0 | 0 | 0 | 331 | 0 | 169 | 0 | 7 | 51 | 403 | 0 | 0 | 0 | 37 | 0 | 35 | 0 | 0 | 110 | 6 | 0 | 0 |
| 3 | 4 | 0 | 0 | 0 | 222 | 0 | 134 | 0 | 12 | 37 | 246 | 0 | 0 | 0 | 61 | 0 | 24 | 0 | 0 | 69 | 4 | 0 | 0 |
| 3 | 5 | 0 | 0 | 0 | 175 | 0 | 140 | 0 | 14 | 33 | 347 | 0 | 0 | 4 | 150 | 0 | 25 | 0 | 0 | 76 | 4 | 0 | 0 |
| 3 | 6 | 0 | 0 | 0 | 252 | 0 | 156 | 0 | 9 | 44 | 292 | 0 | 0 | 0 | 35 | 0 | 28 | 1 | 0 | 77 | 4 | 0 | 0 |
| Mean: | | 0 | 0 | 0 | 235 | 0 | 143 | 0 | 9 | 43 | 306 | 0 | 0 | 1 | 64 | 0 | 28 | 1 | 0 | 72 | 4 | 0 | 0 |
| StdDev: | | 0 | 0 | 0 | 59 | 0 | 21 | 0 | 3 | 7 | 74 | 0 | 0 | 2 | 45 | 0 | 5 | 2 | 0 | 23 | 2 | 0 | 0 |
| t-test | | nd | nd | nd | 0.01 | nd | 0.26 | nd | 0.01 | 0.10 | 0.02 | nd | 0.36 | 0.40 | 0.29 | nd | 0.08 | 0.36 | nd | 0.88 | 0.27 | nd | nd |

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagaaatcca aagagcaaat gg                                              22
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
agaatggaaa actggaatag g                                         21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
tcttcgatgc ttcggattcc                                           20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gaattctcgg aatctctgtt g                                         21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
ttacaagcag tgcagaaaac c                                         21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
agtaaacatt gaaaccacag cc                                        22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
tctgcagctc tgtgtgaagg                                           20

```
<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cttcaaaaac ttctccacaa cc                                           22

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cccacgccac gctctcc                                                 17

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcctgtcagt tggtgctcc                                               19
```

TREATMENT OF LUNG AND PULMONARY DISEASES AND DISORDERS

CROSS-REFERENCE TO RELATED APPLICATIONS

This application claims benefit to U.S. Provisional Patent Application No. 61/139,425, filed Dec. 19, 2008, the contents of which are incorporated by reference herein in their entirety.

FIELD OF THE INVENTION

The invention relates to the field of cell based or regenerative therapy for lung disorders, diseases and injuries.

BACKGROUND OF THE INVENTION

Various publications, including patents, published applications and technical articles are cited throughout the specification. Each of these cited publications is incorporated by reference herein, in its entirety.

Lung disease, both chronic and acute, remains a significant cause of morbidity and mortality throughout the world. Chronic obstructive pulmonary disease (COPD) is the fourth leading cause of death in the world (Spurzem and Rennard, Semin Respir Crit Care Med, 2005; 26: 142-153) and can be caused by anatomic narrowing of the airways or blocking of airways with mucus that interferes with normal breathing. Additionally, interstitial lung disease, also known as pulmonary fibrosis, is classified as a restrictive disease that includes a variety of chronic lung disorders. Management of chronic lung disease includes drug therapy, oxygen therapy, surgery, and pulmonary rehabilitation.

While 90% of COPD patients are smokers, only 10% of smokers develop the disease, suggesting that genetic predisposition may be an important prognostic factor. (Siafakas and Tzortzaki, Respir Med, 2002 August; 96(8): 615-24). Smoker's lung disease is characterized by chronic active inflammation, airway mucus hypersecretion, and emphysema (MacNee, Proc Am Thorac Soc., 2005; 2(4): 258-66; discussion 290-1) and is only partially reversible upon cessation of smoking (Spurzem and Rennard, Semin Respir Crit Care Med, 2005; 26: 142-153). Inflammation of the airways and lung parenchyma plays a major role in the pathogenesis of chronic obstructive pulmonary disease. Cigarette smoke has been shown to induce pulmonary inflammation and ultimately lead to COPD even if exposure to the cigarette smoke has stopped.

Emphysema is one of the major factors determining morbidity and mortality in chronic obstructive pulmonary diseases. This disease is characterized, for example, by loss of elasticity of the lung tissue, from destruction of structures supporting the lung tissues such as alveoli, and destruction of capillaries feeding the alveoli. This destruction can be caused by inflammatory enzymes, for example elastin. Emphysema is defined as the enlargement of peripheral air space in the lung (including respiratory bronchioles and alveoli), which is accompanied by the destruction of alveolar wall structures. The incidence of patients with emphysema has increased in the past decades as a result of the increase in environmental pollutants, cigarette smoking, and other exposure to noxious substances. The current standard of care today demonstrates that only lung transplantation can provide remediation for severe emphysema. There remains a need for an adequate and useful approach to treat, repair and/or ameliorate lung damage in patients with emphysema, such as elastase-induced emphysema.

Animal models exposed to cigarette smoke have been studied to investigate the pathology and the efficacy of various therapeutic interventions. Unfortunately, these studies have only demonstrated limited success. Part of the problem is that commonly used rat and mouse strains show only mild inflammation and mucus secretion in response to cigarette smoke. (Guerassimov, A, et al., Am J Respir Crit Med, 2004 Nov. 1; 170(9): 974-80. Epub 2004 Jul. 28). and the corresponding injuries are rapidly reversible. Healthy laboratory rodents may therefore possess an extraordinary ability to compensate and regenerate lung function following an injury, which may underlie their relative resistance to developing COPD. It has recently been shown that the genetically predisposed spontaneous hypersensitive (SH) rats display phenotypes (e.g., systemic inflammation, hypercoagulation, oxidative stress, and suppressed immune function) that are also found in COPD patients. (Yu, B, et al., Inhal Toxicol, 2008 May; 20(7): 623-33). Therefore, the SH rat model may offer a more relevant model of experimental COPD.

Restrictive lung disease is one of the most common causes of morbidity and mortality and has three primary etiologies, lung cancer, pneumonia and pulmonary fibrosis. Idiopathic pulmonary fibrosis (IPF) is a crippling disease characterized by progressive dyspnea and is associated with a high mortality rate, progressive fixed tissue fibrosis, architectural distortion, and loss of function. (Ortiz, L A, et al., Proc Natl Acad Sci USA., 2003 Jul. 8, 2003; 100(14):8407-11. Epub 2003 Jun. 18). An excess of profibrotic cytokines or a deficiency in antifibrotic cytokines has been implicated in the pathologic process. In the United States, prevalence estimates for idiopathic pulmonary fibrosis vary from three to six cases per one hundred thousand people. Presently, no effective therapies to reverse or retard the course of the disease are available. Most treatments, such as corticosteroids, immunosuppressive, immunomodulatory, or antifibrotic agents, seek to suppress inflammation, but none has been proven to alter IPF disease progression. Therefore, a significant need exists for the development of novel therapies aimed at slowing or halting fibrosis while enhancing endogenous lung repair and regeneration.

It has been shown that mesenchymal stem cells (MSCs) can differentiate into alveolar epithelial cells in injured lungs of mice injured with bleomycin (BLM), and the engraftment of MSCs may suppress inflammation and deposition of collagen in damaged lung tissue. (Zhao, F, et al., Transplant Proceedings, 2008 June; 40(5):1700-1705; Ortiz, L A, et al., Proc Natl Acad Sci USA., 2003 Jul. 8, 2003; 100(14):8407-11, Epub 2003 Jun. 18; Rojas et al., Am J Respir Cell Mol Biol, 2005; 33:145). BLM is a cytostatic antibiotic with antitumor activity and is a well-recognized compound to study pulmonary fibrosis in animal models. It induces alveolar epithelial cell injury and inflammation in the lung, leading to pulmonary fibrosis.

Acute lung injury (ALI) and acute respiratory distress syndrome (ARDS) also continue to be significant causes of morbidity and mortality in the intensive care setting. ALI and ARDS are serious diseases characterized by the abrupt onset of hypoxemia with diffuse pulmonary edema in response to either direct injury (e.g., drowning, pneumonia, inhaled toxic gases, and pulmonary contusion) or indirect injury (e.g., severe sepsis, transfusion, shock, and pancreatitis). ALI and ARDS are currently treated by mechanical ventilation and supportive care.

Cell therapy is one of the most exciting fields in translational medicine and is developing into a new therapeutic platform to treat a vast array of clinical disorders. Over the past five years, the field of cell therapies in lung diseases has continued to grow rapidly. Several studies have demonstrated the feasibility of employing cell therapy to treat lung disease. For example, circulating endothelial progenitor cells (EPCs) may contribute to regeneration of diseased pulmonary vasculature and are being investigated in patients with pulmonary hypertension. (Diller, G P, et al., *Circulation*, 2008 Jun. 10, 117(23): 3020-30, EPub 2008 Jun. 2). In addition, recent publications demonstrate that mesenchymal stem cells (MSCs) also suppress lung injury and inflammation in several mouse models of inflammatory and immune-mediated lung diseases. (Weiss, D J, et al., *Proc Am Thorac. Soc.*, 2008 Jul. 15; 5(5):637-67). Despite these promising findings, little attention has been placed on the development of a cell therapy for ALI.

Presently, there is interest in using either stem cells, which can divide and differentiate, or muscles cells from other sources, including smooth and skeletal muscles cells, to assist in the repair or reversal of tissue damage, such as lung damage due to lung diseases, disorders or injury. Transplantation of stem cells can be utilized as a clinical tool for reconstituting a target tissue, thereby restoring physiologic and anatomic functionality. The application of stem cell technology is wide-ranging, including tissue engineering, gene therapy delivery, and cell therapeutics, i.e., delivery of biotherapeutic agents to a target location via exogenously supplied living cells or cellular components that produce or contain those agents. The identification of stem cells has stimulated research aimed at the selective generation of specific cell types for regenerative medicine.

A reliable, well-characterized and plentiful supply of substantially homogenous populations of such cells having the ability to differentiate into an array of lung tissue, including vascular structures, would be an advantage in a variety of diagnostic and therapeutic applications for lung repair, regeneration, protection and improvement, and for improvement of blood flow and oxygen/$CO_2$ exchange before, during or subsequent to lung damage due to lung diseases, disorders, and/or injuries.

SUMMARY OF THE INVENTION

One aspect of the invention features methods of treating a patient having lung disease, disorders, and/or injuries. Such diseases, disorders, and/or injuries include, but are not limited to, chronic obstructive pulmonary diseases (COPD), pulmonary fibrosis, acute lung injury (ALI), acute respiratory distress syndrome (ARDS), and the damages associated thereto.

One aspect of the invention features a method of treating a patient having lung disease, disorder and/or injury, the method comprising administering to the patient umbilical cord tissue-derived cells in an amount effective to treat the lung disease, disorder and/or injury, and damage associated therewith.

In a particular embodiment, the lung disease, disorder, and/or injury is obstructive, restrictive, and/or caused from injuries such as those associated with or leading to ALI and/or ARDS. In certain embodiments, the cells are induced in vitro to differentiate into lung tissue cells, for example vascular smooth muscle, pericyte, or vascular endothelium lineage cells, prior to administration. In other embodiments, the cells are genetically engineered to produce a gene product that promotes treatment of a lung disease, disorder and/or injury.

In some embodiments of the method, cells are administered with at least one other cell type, which may include lung tissue cells, for example lung progenitor cells, vascular smooth muscle cells, vascular smooth muscle progenitor cells, pericytes, vascular endothelial cells, vascular endothelium progenitor cells, or other multipotent or pluripotent stem cells. The other cell type can be administered simultaneously with, before or after the umbilical cord tissue-derived cells.

In other embodiments, the cells are administered with at least one other agent, which may be an antithrombogenic agent, an anti-inflammatory agent, an immunosuppressive agent, an immunomodulatory agent, pro-angiogenic, or an antiapoptotic agent, for example. The other agent can be administered simultaneously with, before or after the umbilical cord tissue-derived cells.

The cells are preferably administered at or proximal to the sites of the lung disease, disorder, and/or injury, but can also be administered at locations distal to such sites. They can be administered by injection, infusion, a device implanted in the patient, or by implantation of a matrix or scaffold containing the cells. The cells may exert a trophic effect, such as proliferation, on the lung tissue of the patient. The cells may induce migration of lung tissue cells, for example vascular smooth muscle cells, vascular endothelial cells, lung progenitor cells, pericytes, vascular smooth muscle progenitor cells, or vascular endothelium progenitor cells to the site or sites of lung disease, disorder, and/or injury.

Another aspect of the invention features pharmaceutical compositions and kits for treating a patient having a lung disease, disorder, and/or injury, comprising a pharmaceutically acceptable carrier, diluent, and/or buffer, and the umbilical cord-tissue derived cells or preparations made from such umbilical cord-tissue derived cells. In some preferred embodiments, the preparations comprise FGF and HGF. The pharmaceutical compositions and kits are designed and/or formulated for practicing the methods of the invention as outlined above.

According to another aspect of the invention, the above-described methods may be practiced using a preparation made from the umbilical cord tissue-derived cells, wherein the preparation comprises a cell lysate of the umbilical cord tissue-derived cells, an extracellular matrix of the umbilical cord tissue-derived cells or a conditioned medium in which the umbilical cord tissue-derived cells were grown. It is preferred that such preparations comprise FGF and HGF. Another aspect of the invention involves practicing the invention with products of the umbilical cord tissue-derived cells, e.g., trophic factors.

Other aspects of the invention feature pharmaceutical compositions and kits containing preparations comprising cell lysates, extracellular matrices or conditioned media of the umbilical cord tissue-derived cells. The compositions may also comprise a pharmaceutically acceptable carrier, diluent, and/or buffer, as known in the art. Other aspects of the invention feature treatment with pharmaceutical compositions and kits comprising products of the umbilical cord tissue-derived cells.

Other features and advantages of the invention will be understood by reference to the detailed description and examples that follow.

Each data point represents measurements obtained from a single animal. The horizontal lines represent the average of all measurements. Student T-test analysis was preformed. The data is shown in tabular form below (Table 8).

Figure 2A:
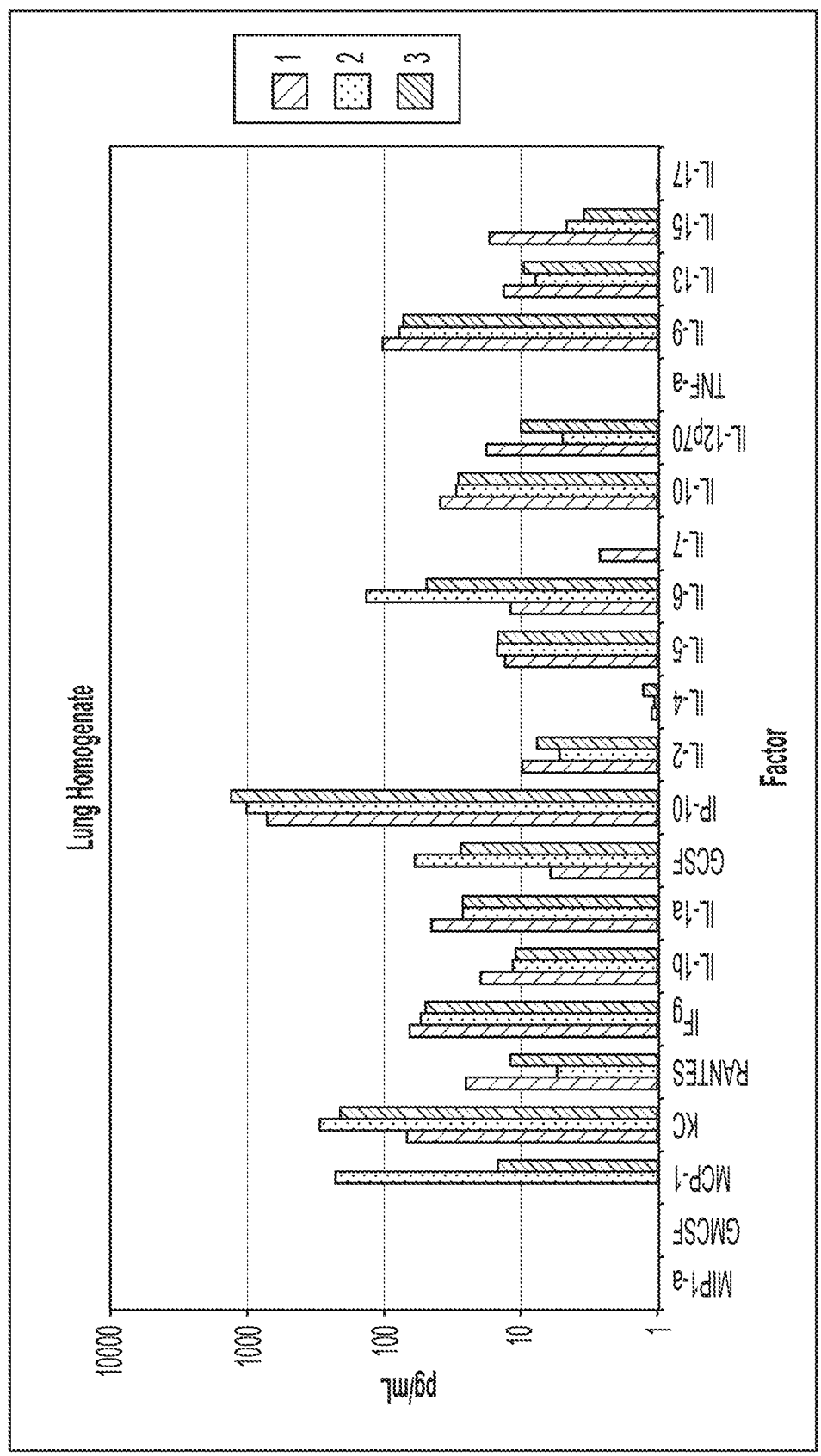

FIG. 2a shows a Cytokine/Chemokine Analysis of Lung Homogenate: The concentrations of twenty-two different cytokines/chemokines were determined for lung homogenate using a mouse 22-multiplex bead kit (Millipore) following the manufacturer's protocol and analyzed using the BioRad Bioplex machine. Data bars represent the mean of six samples. The data is shown in tabular form below (FIG. 3).

FIG. 2b shows a Cytokine/Chemokine Analysis of BALF: The concentrations of twenty-two different cytokines/chemokines were determined for BALF using a mouse 22-multiplex bead kit (Millipore) following the manufacturer's protocol and analyzed using the BioRad Bioplex machine. Data bars represent the mean of six samples. Data shown in tabular form below (FIG. 4).

FIG. 3 shows a lung Homogenate Cytokine/Chemokine Analysis: The concentrations of twenty-two different cytokines/chemokines were determined for lung homogenate using a mouse 22-multiplex bead kit (Millipore) following the manufacturer's protocol and analyzed using the BioRad Bioplex machine.

FIG. 4 shows a BALE Cytokine/Chemokine Analysis: The concentrations of twenty-two different cytokines/chemokines were determined for BALF using a mouse 22-multiplex bead kit (Millipore) following the manufacturer's protocol and analyzed using the BioRad Bioplex machine.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense.

Various terms are used throughout the specification and claims. Such terms are to be given their ordinary meaning in the art unless otherwise indicated. Other specifically defined terms are to be construed in a manner consistent with the definition provided herein.

"Lung tissue" can include, but is not limited to, all lung tissue structures and associated tissues, including, but not limited to, veins, arteries, vessels, capillaries, and cells of the type that are part of, or associated with, such structures; lung and pleural tissue; and vascular smooth muscle, pericyte, and vascular endothelial lineages and/or phenotypes.

As used herein, "respiratory or lung diseases, disorders and injuries" include, but are not limited to, obstructive lung diseases, restrictive lung diseases, respiratory tract infections (upper and lower), respiratory tumors, pleural cavity diseases, and pulmonary vascular diseases. The damage to lung tissue caused by these diseases, disorders and/or injuries can be characterized as lung damage within the scope of the present invention. Furthermore, the damaged lung tissue encompassed by the invention includes all lung tissue structures and associated tissues, including, veins, arteries, vessels, capillaries, and cells of the type that are part of, or associated with, such structures. "Obstructive lung diseases" can include COPD, cystic fibrosis, bronchiectasis, bronchiolitis, emphysema and allergic bronchopulmonary aspergillosis. COPD, for example, is caused by noxious particles or gases (most commonly from smoking), which trigger an abnormal inflammatory response in the lung. The inflammatory response in the larger airways is known as chronic bronchitis, which is diagnosed clinically when people regularly cough up sputum. In the alveoli, the inflammatory response causes destruction of the tissue of the lung, a process known as emphysema. It should be realized that these issues are those associated with COPD as it pertains to the instant invention. The etiology of COPD includes, but is not limited to, tobacco smoking, occupational exposures to workplace dusts (e.g., coal mining, gold mining, the cotton textile industry and chemical industry), air pollution, and genetics.

"Restrictive lung diseases," as used herein, are also known as interstitial lung diseases (ILDs). Many of these are idiopathic. Examples include: idiopathic pulmonary fibrosis, idiopathic interstitial pneumonia (several types), sarcoidosis, eosinophilic pneumonia, lymphangioleiomyomatosis, pulmonary Langerhan's cell histiocytosis, and pulmonary alveolar proteinosis. ILDs affect the interstitium of the lung: alveolar epithelium, pulmonary capillary endothelium, basement membrane, perivascular and perilymphatic tissues. Most types of ILDs involve fibrosis.

Respiratory tumors include both malignant and benign tumors. Malignant tumors include, for example, small cell lung cancer, non-small cell lung cancer (adenocarcinoma, squamous cell carcinoma, and large cell undifferentiated carcinoma), lymphoma, as well as other cancers. Benign tumors are rare but can include pulmonary hamartoma and congenital malformations, for example.

As used herein, "acute lung injury" (ALI) is a diffuse heterogeneous lung injury characterized by hypoxemia, non-cardiogenic pulmonary edema, low lung compliance and widespread capillary leakage. ALI is caused by any stimulus of local or systemic inflammation. Acute respiratory distress syndrome (ARDS) is more severe than ALI. As used herein, ALI and ARDS can be characterized by abrupt onset of hypoxemia with diffuse pulmonary edema in response to either direct injury or indirect injury. As used herein, "direct injury" includes, but is not limited to, lung injuries stemming from drowning episodes, pneumonia, inhaled toxic gases, and pulmonary contusions. As used herein, "indirect injury" can be from severe sepsis, transfusion, shock, and pancreatitis, for example. These injuries that lead to ALI and ARDS result in disruption of the alveolar-capillary interface, leakage of protein rich fluid into the interstitium and alveolar space, extensive release of cytokines, and migration of neutrophils.

The lung diseases, disorders and injuries encompassed by the methods of the present invention are known in the art. The characteristics of each, including associated complications, etiologies, and treatments, are known by those of skill in the art. This includes lung diseases, disorders and injuries not specifically discussed herein, as they would apply to obstructive and restrictive lung diseases, disorders and injuries.

The cells used in the present invention are generally referred to as postpartum cells or postpartum-derived cells (PPDCs). The cells are more specifically "umbilicus-derived cells" or "umbilical cord-derived cells" (UDC), or "umbilical cord tissue-derived cells" (UTC). In addition, the cells may be described as being stem or progenitor cells, the latter term being used in the broad sense. The term "derived" is used to indicate that the cells have been obtained from their biological source and grown or otherwise manipulated in vitro (e.g., cultured in a growth medium to expand the population and/or to produce a cell line). The in vitro manipulations of umbilical stem cells and the unique features of the umbilicus-derived cells of the present invention are described in detail below.

Stem cells are undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts.

Stem cells are classified according to their developmental potential as: (1) totipotent; (2) pluripotent; (3) multipotent; (4) oligopotent; and (5) unipotent. Totipotent cells are able to give rise to all embryonic and extraembryonic cell types. Pluripotent cells are able to give rise to all embryonic cell types. Multipotent cells include those able to give rise to a subset of cell lineages, but all within a particular tissue, organ, or physiological system. For example, hematopoietic stem cells (HSC) can produce progeny that include HSC (self-renewal), blood cell-restricted oligopotent progenitors, and all cell types and elements (e.g., platelets) that are normal components of the blood. Cells that are oligopotent can give rise to a more restricted subset of cell lineages than multipotent stem cells. Cells that are unipotent are able to give rise to a single cell lineage (e.g., spermatogenic stem cells).

Stem cells are also categorized on the basis of the source from which they are obtained. An adult stem cell is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the umbilical cord. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Various terms are used to describe cells in culture. "Cell culture" refers generally to cells taken from a living organism and grown under controlled conditions ("in culture" or "cultured"). A "primary cell culture" is a culture of cells, tissues, or organs taken directly from an organism(s) before the first subculture. Cells are "expanded" in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as "doubling time."

The term "cell line" generally refers to a population of cells formed by one or more subcultivations of a primary cell culture. Each round of subculturing is referred to as a passage. When cells are subcultured, they are referred to as having been "passaged." A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including, but not limited to, the seeding density, substrate, medium, growth conditions, and time between passaging.

"Differentiation" is the process by which an unspecialized ("uncommitted") or less specialized cell acquires the features of a specialized cell, such as a nerve cell or a muscle cell, for example. A "differentiated" cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the "lineage" of a cell defines the heredity of the cell, i.e., which cells it came from and what cells it can give rise to. The lineage of a cell places the cell within a hereditary scheme of development and differentiation.

In a broad sense, a "progenitor cell" is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a "non-renewing progenitor cell" or as an "intermediate progenitor or precursor cell."

Several terms are used herein with respect to cell or tissue transplantation; or cell replacement therapy. The terms "autologous transfer," "autologous transplantation," "autograft" and the like refer to treatments wherein the cell or transplant donor is also the cell or transplant recipient. The terms "allogeneic transfer," "allogeneic transplantation," "allograft" and the like refer to treatments wherein the cell or transplant donor is of the same species as the recipient, but is not the same individual. A cell transfer in which the donor's cells have been histocompatibly matched with a recipient is sometimes referred to as a "syngeneic transfer." The terms "xenogeneic transfer," "xenogeneic transplantation," "xenograft" and the like refer to transplantation wherein the cell or transplant donor is of a different species than the recipient.

The terms "pharmaceutically acceptable carrier" or "pharmaceutically acceptable medium" which may be used interchangeably with the terms "biologically compatible carrier" or "biologically compatible medium" generally refer to reagents, cells, compounds, materials, compositions, and/or dosage forms that are not only compatible with the cells and other agents to be administered therapeutically, but also are, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds and matrices, tubes, sheets and other such materials known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways. The biodegradation rate can vary according to the desired release rate once implanted in the body.

A "conditioned medium" is a medium in which a specific cell or population of cells has been cultured, and then removed. When cells are cultured in a medium, they may secrete cellular factors that can provide trophic support to other cells. Such trophic factors include, but are not limited to, hormones, cytokines, extracellular matrix (ECM), proteins, vesicles, antibodies, and granules. The medium containing the cellular factors is the conditioned medium.

Generally, a "trophic factor" is defined as a substance that promotes survival, growth, proliferation and/or maturation of a cell, or stimulates increased activity of a cell.

As used herein, the term "growth medium" generally refers to a medium sufficient for the culturing of postpartum-derived cells. In particular, one presently preferred medium for the culturing of the cells of the invention comprises Dulbecco's Modified Essential Media (DMEM). Particularly preferred is DMEM-low glucose (DMEM-LG) (Invitrogen, Carlsbad, Calif.). The DMEM-LG is preferably supplemented with serum, most preferably fetal bovine serum or human serum. Typically, 15% (v/v) fetal bovine serum (e.g. defined fetal bovine serum, Hyclone, Logan Utah) is added, along with antibiotics/antimycotics (preferably 100 Unit/milliliter penicillin, 100 milligrams/milliliter streptomycin, and 0.25 microgram/milliliter amphotericin B; (Invitrogen, Carlsbad, Calif.)), and 0.001% (v/v) 2-mercaptoethanol (Sigma, St. Louis Mo.). In some cases different growth media are used or different supplementations are provided, and these are normally indicated in the text as supplementations to growth medium. In certain chemically-defined media the cells may be grown without serum present at all. In such cases, the cells may require certain growth factors, which can be added to the medium to support and sustain the cells. Presently preferred factors to be added for growth in serum-free media include one or more of bFGF, EGF, IGF-I, and PDGF. In more preferred embodiments, two, three or all four of the factors are added to serum free or chemically defined media. In other embodiments, LIF is added to serum-free medium to support or improve growth of the cells.

The term "standard growth conditions," as used herein refers to culturing of cells at 37° C., in a standard atmosphere comprising 5% $CO_2$ and relative humidity maintained at about 100%. While the foregoing conditions are useful for culturing, it is to be understood that such conditions are capable of being varied by the skilled artisan who will appreciate the options available in the art for culturing cells.

The term "effective amount" refers to a concentration or amount of a compound, material, or composition, as described herein, that is effective to achieve a particular biological result. Such results include, but are not limited to, the regeneration, repair, or improvement of skeletal tissue, the improvement of blood flow, and/or the stimulation and/or the support of angiogenesis in patients with lung damage from those diseases, disorders and injuries within the scope of this invention. Such effective activity may be achieved, for example, by administering the cells and/or compositions of the present invention to patients with lung damage as described herein. With respect to the administration of UTC to a patient in vivo, an effective amount may range from as few as several hundred or fewer, to as many as several million or more. In specific embodiments, an effective amount may range from about $10^3$ to about $10^{11}$ cells more specifically, at least about $10^4$ cells. It will be appreciated that the number of cells to be administered will vary depending on the specifics of the lung disease, disorder or injury to be treated, including but not limited to the size or total volume/surface area to be treated, and the proximity of the site of administration to the location of the region to be treated, among other factors familiar to the medicinal biologist.

The terms "treat," "treating" or "treatment" refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters; including the results of a physical examination, or neurological examination.

The terms "effective period," "effective period of time" or "effective conditions" refer generally to a period of time or other controllable conditions (e.g., temperature, humidity for in vitro methods) necessary or preferred for an agent or pharmaceutical composition to achieve its intended result.

The terms "individual," "patient" or "subject" are used interchangeably herein, and refer to animals, preferably mammals, and more preferably humans, who are treated with the pharmaceutical or therapeutic compositions or in accordance with the methods described herein.

The term "matrix" as used herein generally refers to biodegradable and/or bioresorbable materials that are administered with the cells to a patient. The matrix may act as a temporary scaffold until replaced by newly grown cells, such as, skeletal muscle, pericytes, vascular smooth muscle, or vascular endothelial tissue. In some embodiments, the matrix may provide for the sustained release of trophic factors or other agents used in conjunction with the cells and may provide a structure for developing tissue growth in the patient. In other embodiments, the matrix simply provides a temporary scaffold for the developing tissue. The matrix can be in particulate form (macroparticles greater than 10 microns in diameter or microparticles less than 10 microns in diameter), or it can be in the form of a structurally stable, three-dimensional implant (e.g., a scaffold). The matrix can be a slurry, hydrogel or a three-dimensional structure such as a cube, cylinder, tube, block, film, sheet or an appropriate anatomical form.

The term "scaffold" as used herein generally refers to a three dimensional porous structure that provides a template for cell growth. A scaffold is made of biodegradable and/or bioresorbable materials that degrade over time within the body. The length of time taken for the scaffold to degrade may depend upon the molecular weight of the materials. Thus, higher molecular weight material may result in polymer scaffolds which retain their structural integrity for longer periods of time; while lower molecular weights result in both slower release and shorter scaffold lives. The scaffold may be made by any means known in the art. Examples of polymers which can be used to form the scaffold include natural and synthetic polymers.

The term "isolate" as used herein generally refers to a cell which has been separated from its natural environment. This term includes gross physical separation from its natural environment, e.g., removal from the donor animal. In preferred embodiments, an isolated cell is not present in a tissue, i.e., the cell is separated or dissociated from the neighboring cells with which it is normally in contact. Preferably, cells are administered as a cell suspension. As used herein, the phrase "cell suspension" includes cells which are in contact with a medium and which have been dissociated, e.g., by subjecting a piece of tissue to gentle trituration.

In its various embodiments described herein, the present invention features methods and pharmaceutical compositions for treatment of lung diseases, disorders and/or injuries that utilize progenitor cells and cell populations derived from postpartum tissues, umbilicus tissue in particular. These methods and pharmaceutical compositions are designed to stimulate and support angiogenesis, to improve blood flow, to regenerate, repair, and improve lung tissue damaged by a lung disease, disorder and/or injury, and/or to protect the lung tissue from such diseases, disorders and/or injuries. The cells, cell populations and preparations comprising cell lysates, conditioned media and the like, used in the pharmaceutical preparations and methods of the present invention are described in detail in US Patent Publication Nos. 2005/0032209, 2005/0058631 and 2005/0054098, and also herein below.

According to the methods described herein, a mammalian umbilical cord is recovered upon or shortly after termination of either a full-term or pre-term pregnancy, for example, after expulsion of the after birth. The postpartum tissue may be transported from the birth site to a laboratory in a sterile container such as a flask, beaker, culture dish, or bag. The container may have a solution or medium, including but not limited to a salt solution, such as Dulbecco's Modified Eagle's Medium (DMEM) (also known as Dulbecco's Minimal Essential Medium) or phosphate buffered saline (PBS), or any solution used for the transportation of organs used for transplantation, such as University of Wisconsin solution or perfluorochemical solution. One or more antibiotic and/or antimycotic agents, such as, but not limited to, penicillin, streptomycin, amphotericin B, gentamicin, and nystatin, may be added to the medium or buffer. The postpartum tissue may be rinsed with an anticoagulant solution such as heparin-containing solution. It is preferable to keep the tissue at about 4 to about 10° C. prior to extraction of the UTC. It is even more preferable that the tissue not be frozen prior to extraction of the UTC.

Isolation of the UTC preferably occurs in an aseptic environment. The umbilical cord may be separated from the placenta by means known in the art. Blood and debris are preferably removed from the postpartum tissue prior to isolation of the UTC. For example, the postpartum tissue may be washed with buffer solution, including but not limited to phosphate buffered saline. The wash buffer also may comprise one or more antimycotic and/or antibiotic agents, including but not limited to penicillin, streptomycin, amphotericin B, gentamicin, and nystatin.

Postpartum tissue comprising an umbilical cord, or a fragment or section thereof, is preferably disaggregated by mechanical force (mincing or shear forces). In a presently preferred embodiment, the isolation procedure also utilizes an enzymatic digestion process. Many enzymes are known in the art to be useful for the isolation of individual cells from complex tissue matrices to facilitate growth in culture. Digestion enzymes range from weakly digestive (e.g. deoxyribonucleases and the neutral protease, dispase) to strongly digestive (e.g. papain and trypsin), and are available commercially. A non-exhaustive list of such enzymes includes mucolytic enzyme activities, metalloproteases, neutral proteases, serine proteases (such as trypsin, chymotrypsin, or elastase), and deoxyribonucleases. Presently preferred are enzyme activities selected from metalloproteases, neutral proteases and mucolytic activities. For example, collagenases are known to be useful for isolating various cells from tissues. Deoxyribonucleases can digest single-stranded DNA and can minimize cell-clumping during isolation. Preferred methods involve enzymatic treatment with collagenase and dispase, or collagenase, dispase, and hyaluronidase. The skilled artisan will appreciate that many such enzyme treatments are known in the art for isolating cells from various tissue sources, and is well-equipped to assess new or additional enzymes or enzyme combinations for their utility in isolating the cells of the invention. Preferred enzyme treatments can be from about 0.5 to 2 hours long or longer. In other preferred embodiments, the tissue is incubated at about 37° C. during the enzyme treatment of the dissociation step.

The isolated cells may be used to initiate, or seed, cell cultures. Isolated cells are transferred to sterile tissue culture vessels either uncoated or coated with extracellular matrix or ligands such as laminin, collagen (native, denatured or crosslinked), gelatin, fibronectin, and other extracellular matrix proteins. The cells are cultured in any culture medium capable of sustaining growth of the cell such as, but not limited to, DMEM (high or low glucose), advanced DMEM, DMEM/MCDB 201, Eagle's basal medium, Ham's F10 medium (F10), Ham's F-12 medium (F12), Iscove's modified Dulbecco's medium, Mesenchymal Stem Cell Growth Medium (MSCGM), DMEM/F12, RPMI 1640, and serum/media free medium sold under the trade name CELLGRO-FREE (Mediatch, Inc., Herndon, Va.). The culture medium may be supplemented with one or more components including, for example, fetal bovine serum (FBS), preferably about 2-15% (v/v); equine serum (ES); human serum (HS); beta-mercaptoethanol (BME or 2-ME), preferably about 0.001% (v/v); one or more growth factors, for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin (EPO); amino acids, including L-valine; and one or more antibiotic and/or antimycotic agents to control microbial contamination, such as penicillin G, streptomycin sulfate, amphotericin B, gentamicin, and nystatin, either alone or in combination. The culture medium preferably comprises growth medium (e.g., DMF-M-low glucose, serum, BME and an antibiotic agent).

The cells are seeded in culture vessels at a density to allow cell growth. In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at a temperature of about 25 to about 40° C. and more preferably are cultured at 37° C. The cells are preferably cultured in an incubator. The medium in the culture vessel can be static or agitated, for example, using a bioreactor. The UTC is preferably grown under low oxidative stress (e.g., with addition of glutathione, vitamin C, catalase, vitamin E, N-acetylcysteine). "Low oxidative stress," as used herein, refers to conditions of no or minimal free radical damage to the cultured cells.

Methods for the selection of the most appropriate culture medium, medium preparation, and cell culture techniques are well known in the art and are described in a variety of sources, including Doyle et al., (eds.), 1995, Cell & Tissue Culture: Laboratory Procedures, John Wiley & Sons, Chichester; and Ho and Wang (eds.), 1991, Animal Cell Bioreactors, Butterworth-Heinemann, Boston, which are incorporated herein by reference.

In some embodiments of the invention, the UTC are passaged, or removed to a separate culture vessel containing fresh medium of the same or a different type as that used initially, where the population of cells can be mitotically expanded. The cells of the invention may be used at any point between passage 0 and senescence. The cells preferably are passaged between about 3 and about 25 times, more preferably are passaged about 4 to about 12 times, and preferably are passaged 10 or 11 times. Cloning and/or subcloning may be performed to confirm that a clonal population of cells has been isolated.

In some aspects of the invention, the different cell types present in postpartum tissue are fractionated into subpopulations from which the UTC can be isolated. Fractionation or selection may be accomplished using standard techniques for cell separation including, but not limited to, enzymatic treatment to dissociate postpartum tissue into its component cells, followed by cloning and selection of specific cell types, including, but not limited to: selection based on morphological and/or biochemical markers; selective growth of desired cells (positive selection); selective destruction of unwanted cells (negative selection); separation based upon differential cell agglutinability in the mixed population as, for example, with soybean agglutinin; freeze-thaw procedures; differential adherence properties of the cells in the mixed population; filtration; conventional and zonal centrifugation; centrifugal elutriation (counter-streaming centrifugation); unit gravity separation; countercurrent distribution; electrophoresis; and fluorescence activated cell sorting (FACS).

The culture medium is changed as necessary. For example, by carefully aspirating the medium from the dish with a pipette, and replenishing with fresh medium. Incubation is continued until a sufficient number or density of cells accumulate in the dish. Thereafter, any original explanted tissue sections that exist may be removed and the remaining cells separated from the dish by trypsinization using standard techniques or by using a cell scraper. After trypsinization, the cells are collected, removed to fresh medium and incubated as above. In some embodiments, the medium is changed at least once at approximately 24 hours post-trypsinization to remove any floating cells. The cells remaining in culture are considered to be UTC.

The UTC may be cryopreserved. Accordingly, in a preferred embodiment described in greater detail below, the UTC for autologous transfer (for either the mother or child) may be derived from appropriate postpartum tissues following the birth of a child, then cryopreserved so as to be available in the event they are later needed for transplantation.

The UTC may be characterized, for example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of PDC-conditioned medium, for example, by Enzyme Linked ImmunoSorbent Assay (ELISA)), mixed lymphocyte reaction (e.g., as measure of stimulation of PBMCs), and/or other methods known in the art.

Examples of UTC derived from umbilicus tissue were deposited with the American Type Culture Collection on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

In various embodiments, the UTC possess one or more of the following growth features: (1) they require L-valine for growth in culture; (2) they are capable of growth in atmospheres containing oxygen from about 5% to about 20%; (3) they have the potential for at least about 40 doublings in culture before reaching senescence; and (4) they attach and expand on tissue culture vessels that are uncoated, or that are coated with gelatin, laminin, collagen, polyornithine, vitronectin or fibronectin.

In certain embodiments the UTC possesses a normal karyotype, which is maintained as the cells are passaged. Methods for karyotyping are available and known to those of skill in the art.

In other embodiments, the UTC may be characterized by production of certain proteins, including: (1) production of at least one of tissue factor, vimentin, and alpha-smooth muscle actin; and (2) production of at least one of CD10, CD13, CD44, CD73, CD90, PDGFr-alpha, PD-L2 and HLA-A,B,C cell surface markers, as detected by flow cytometry. In other embodiments, the UTC may be characterized by lack of production of at least one of CD31, CD34, CD45, CD80, CD86, CD117, CD141, CD178, B7-H2, HLA-G, and HLA-DR, DP, DQ cell surface markers, as detected by flow cytometry. Particularly preferred are cells that produce at least two of: tissue factor; vimentin; and alpha-smooth muscle actin. More preferred are those cells producing all three of the proteins: tissue factor; vimentin; and alpha-smooth muscle actin.

In other embodiments, the UTC may be characterized by gene expression, which relative to a human cell that is a fibroblast, a mesenchymal stem cell, or an iliac crest bone marrow cell, is increased for a gene encoding at least one of: interleukin 8; reticulon 1; chemokine (C—X—C motif) ligand 1 (melonoma growth stimulating activity, alpha); chemokine (C—X—C motif) ligand 6 (granulocyte chemotactic protein 2); chemokine (C—X—C motif) ligand 3; and tumor necrosis factor, alpha-induced protein 3.

In yet other embodiments, the UTC may be characterized by gene expression, which relative to a human cell that is a fibroblast, a mesenchymal stem cell, or an iliac crest bone marrow cell, is reduced for a gene encoding at least one of: short stature homeobox 2; heat shock 27 kDa protein 2; chemokine (C—X—C motif) ligand 12 (stromal cell-derived factor 1); elastin (supravalvular aortic stenosis, Williams-Beuren syndrome); Homo sapiens mRNA; cDNA DKFZp586M2022 (from clone DKFZp586M2022); mesenchyme homeo box 2 (growth arrest-specific homeo box); sine oculis homeobox homolog 1 (Drosophila); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (Drosophila); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; Homo sapiens cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (Drosophila); KIAA1034 protein; vesicle-associated membrane protein 5 (myobrevin); EGF-containing fibulin-like extracellular matrix protein 1; early growth response 3; distal-less homeo box 5; hypothetical protein F1120373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); Homo sapiens mRNA full length insert cDNA clone EUROIMAGE 1968422; EphA3; KIAA0367 protein; natriuretic peptide receptor C/guanylate cyclase C (atrionatriuretic peptide receptor C); hypothetical protein F1114054; Homo sapiens mRNA; cDNA DKFZp564B222 (from clone DKFZp564B222); BCL2/adenovirus E1B 19 kDa interacting protein 3-like; AE binding protein 1; and cytochrome c oxidase subunit VIIa polypeptide 1 (muscle).

In other embodiments, the UTC may be characterized by secretion of at least one of: MCP-1; IL-6; IL-8; GCP-2; HGF; KGF; FGF; HB-EGF; BDNF; TPO; MIP1b; I309; MDC; RANTES; and TIMP1. In some embodiments, the UTC may be characterized by lack of secretion of at least one of: TGF-beta2; ANG2; PDGFbb; MIP1a; and VEGF, as detected by ELISA.

In some preferred embodiments, the UTC is derived from umbilical cord tissue substantially free of blood, are capable of self-renewal and expansion in culture, require L-valine for growth, can grow in at least about 5% oxygen, and comprise at least one of the following characteristics: (1) the potential for at least about 40 doublings in culture; (2) the ability to attach and expand on an uncoated tissue culture vessel or one coated with gelatin, laminin, collagen, polyornithine, vitronectin, or fibronectin; (3) production of vimentin and alpha-smooth muscle actin; (4) production of CD10, CD13, CD44, CD73, and CD90; and (5) expression of a gene, which relative to a human cell that is a fibroblast, a mesenchymal stem cell, or an iliac crest bone marrow cell, is increased for a gene encoding interleukin 8 and reticulon 1. In some embodiments, such UTC does not produce CD45 and CD117.

The UTC described above can be used in methods for treating a patient having peripheral vascular disease, can be used in pharmaceutical compositions for treating peripheral vascular disease, for example, wherein such compositions comprise the cells having these characteristics and a pharmaceutically acceptable carrier, and can be used in kits for making, using, and practicing such methods and pharmaceutical compositions as described and exemplified herein. In addition, the UTC as described above can be used to generate conditioned cell culture media or to make preparations such as cell extracts and subcellular fractions that can be used for making, using, and practicing such methods and pharmaceutical compositions as described and exemplified herein.

In preferred embodiments, the cell comprises two or more of the above-listed growth, protein/surface marker production, gene expression or substance-secretion characteristics. More preferred is a cell comprising, three, four, five or more of the characteristics. Still more preferred are UTC comprising six, seven, eight or more of the characteristics. Still more preferred presently is a cell comprising all of above characteristics.

Among cells that are presently preferred for use with the invention in several of its aspects are UTC having the characteristics described above, and more particularly, those wherein the cells have normal karyotypes and maintain normal karyotypes with passaging, and further wherein the cells express each of the markers CD10, CD13, CD44, CD73, CD90, PDGFr-alpha, and HLA-A,B,C, and wherein the cells produce the immunologically-detectable proteins which correspond to the listed markers. Still more preferred are those cells which, in addition to the foregoing, do not produce proteins corresponding to any of the markers CD31, CD34, CD45, CD117, CD141, or HLA-DR,DP,DQ, as detected by flow cytometry.

Certain cells having the potential to differentiate along lines leading to various phenotypes are unstable and thus can spontaneously differentiate. Presently preferred for use with the invention are cells that do not spontaneously differentiate, for example, along myoblast, skeletal muscle, vascular smooth muscle, pericyte, hemangiogenic, angiogenic, vasculogenic, or vascular endothelial lines. Preferred cells, when grown in growth medium, are substantially stable with respect to the cell markers produced on their surface, and with respect to the expression pattern of various genes, for example, as determined using a medical diagnostic test sold under the trade name GENECHIP (Affymetrix, Inc., Santa Clara, Calif.). The cells remain substantially constant, for example, in their surface marker characteristics over passaging and through multiple population doublings.

Another aspect of the invention features the use of populations of a UTC described above. In some embodiments, the cell population may be heterogeneous. A heterogeneous cell population of the invention may comprise at least about 5%, 10%, 20%, 30%, 40%, 50%, 60%, 70%, 80%, 90%, or 95% UTC of the invention. The heterogeneous cell populations of the invention may further comprise stem cells or other progenitor cells, such as myoblasts or other muscle progenitor cells, hemangioblasts, or blood vessel precursor cells; or it may further comprise fully differentiated skeletal muscle cells, smooth muscle cells, pericytes, or blood vessel endothelial cells. In some embodiments, the population is substantially homogeneous, i.e., comprises substantially only the UTC (preferably at least about 96%, 97%, 98%, 99% or more UTC). The homogeneous cell population of the invention may comprise umbilicus-derived cells. Homogeneous populations of umbilicus-derived cells are preferably free of cells of maternal lineage. Homogeneity of a cell population may be achieved by any method known in the art, for example, by cell sorting (e.g., flow cytometry) or by clonal expansion in accordance with known methods. Thus, preferred homogeneous UTC populations may comprise a clonal cell line of postpartum-derived cells. Such populations are particularly useful when a cell clone with highly desirable functionality has been isolated.

Also provided herein is the use of populations of cells incubated in the presence of one or more factors, or under conditions, that stimulate stem cell differentiation along a vascular smooth muscle, vascular endothelial, or pericyte pathway. Such factors are known in the art and the skilled artisan will appreciate that determination of suitable conditions for differentiation can be accomplished with routine experimentation. Optimization of such conditions can be accomplished by statistical experimental design and analysis, for example, response surface methodology allows simultaneous optimization of multiple variables in a biological culture. Presently preferred factors include, but are not limited to, growth or trophic factors, chemokines, cytokines, cellular products, demethylating agents, and other stimuli which are now known or later determined to stimulate differentiation, for example, of stem cells along angiogenic, hemangiogenic, vasculogenic, skeletal muscle, vascular smooth muscle, pericyte, or vascular endothelial pathways or lineages.

The UTC may also be genetically modified to produce therapeutically useful gene products, to produce angiogenic agents to facilitate or support additional blood vessel formation or growth, or to produce factors to recruit endothelial progenitor cells to the area of lung damage. Endothelial progenitor cells facilitate vasculogenesis and blood flow, particularly following an ischemic event. (Urbich C and Dimmeler S, *Circ. Res.*, 2004; 95:343-53). Factors that play a role in endothelial cell recruitment include, but are not limited to, VEGF, stromal derived factor-1 (SDF-1), erythropoietin (EPO), G-CSF, statins, strogen, PPAR-$\gamma$, CXCR4, FGF, and HGF. Genetic modification may be accomplished using any of a variety of vectors including, but not limited to, integrating viral vectors, e.g., retrovirus vector or adenoassociated viral vectors; non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

Hosts cells are preferably transformed or transfected with DNA controlled by, or in operative association with, one or more appropriate expression control elements such as promoter or enhancer sequences, transcription terminators, polyadenylation sites, among others, and a selectable marker. Any promoter may be used to drive the expression of the inserted gene. For example, viral promoters include, but are not limited to, the CMV promoter/enhancer, SV 40, papillomavirus, Epstein-Barr virus or elastin gene promoter. In some embodiments, the control elements used to control expression of the gene of interest can allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary. Inducible promoters include, but are not limited to, those associated with metallothionein and heat shock proteins.

Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines that express the gene product.

The cells of the invention may be genetically engineered to "knock out" or "knock down" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a gene native to a skeletal muscle cell, vascular smooth muscle cell, pericyte, vascular endothelial cell, or progenitor cells thereof can be reduced or knocked out using a number of techniques including, for example, inhibition of expression by inactivating the gene using the homologous recombination technique. Typically, an exon encoding an important region of the protein (or an exon 5' to that region) is interrupted by a positive selectable marker, e.g., neo, preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted. (Mombaerts et al., *Proc. Nat. Acad. Sci. U.S.A.*, 1991; 88:3084-87). Antisense, DNAzymes, ribozymes, small interfering RNA (siRNA) and other such molecules that inhibit expression of the target gene can also be used to reduce the level of target gene activity. For example, antisense RNA molecules that inhibit the expression of major histocompatibility gene complexes (HLA) have been shown to be most versatile with respect to immune responses. Still further, triple helix molecules can be utilized in reducing the level of target gene activity.

In other aspects, the invention utilizes cell lysates and cell soluble fractions prepared from a UTC, or heterogeneous or homogeneous cell populations comprising a UTC, as well as a UTC or populations thereof that have been genetically modified or that have been stimulated to differentiate along a skeletal muscle, vascular smooth muscle, pericyte, or vascular endothelium pathway. Such lysates and fractions thereof have many utilities. Use of the UTC lysate soluble fraction (i.e., substantially free of membranes) in vivo, for example, allows the beneficial intracellular milieu to be used allogeneically in a patient without introducing an appreciable amount of the cell surface proteins most likely to trigger rejection, or other adverse immunological responses. Methods of lysing cells are well-known in the art and include various means of mechanical disruption, enzymatic disruption, or chemical disruption, or combinations thereof. Such cell lysates may be prepared from cells directly in their growth medium, and thus contain secreted growth factors and the like, or they may be prepared from cells washed free of medium in, for example, PBS or other solution. Washed cells may be resuspended at concentrations greater than the original population density if preferred.

In one embodiment, whole cell lysates are prepared, e.g., by disrupting cells without subsequent separation of cell fractions. In another embodiment, a cell membrane fraction is separated from a soluble fraction of the cells by routine methods known in the art, e.g., centrifugation, filtration, or similar methods.

Cell lysates or cell soluble fractions prepared from populations of postpartum-derived cells may be used as is, further concentrated by, for example, ultrafiltration or lyophilization, or even dried, partially purified, combined with pharmaceutically-acceptable carriers or diluents as are known in the art, or combined with other compounds such as biologicals, for example, pharmaceutically useful protein compositions. Cell lysates or fractions thereof may be used in vitro or in vivo, alone or, for example, with autologous or syngeneic live cells. The lysates, if introduced in vivo, may be introduced locally at a site of treatment, or remotely to provide, for example, needed cellular growth factors to a patient.

In a further embodiment, the UTC can be cultured in vitro to produce biological products in high yield. A UTC that either naturally produces a particular biological product of interest (e.g., a trophic factor), or that has been genetically engineered to produce a biological product, can be clonally expanded using the culture techniques described herein. Alternatively, cells may be expanded in a medium that induces differentiation to a skeletal muscle, vascular smooth muscle, pericyte, or vascular endothelial lineage. In each case, biological products produced by the cell and secreted into the medium can be readily isolated from the conditioned medium using standard separation techniques, e.g., such as differential protein precipitation, ion-exchange chromatography, gel filtration chromatography, electrophoresis, and HPLC, to name a few. A "bioreactor" may be used to take advantage of the flow method for feeding, for example, a three-dimensional culture in vitro. Essentially, as fresh media is passed through the three-dimensional culture, the biological product is washed out of the culture and may then be isolated from the outflow, as above.

Alternatively, a biological product of interest may remain within the cell and, thus, its collection may require that the cells be lysed, as described above. The biological product may then be purified using any one or more of the above-listed techniques.

In other embodiments, the invention utilizes conditioned medium from cultured UTC for use in vitro and in vivo as described below. Use of the UTC conditioned medium allows the beneficial trophic factors secreted by the UTC to be used allogeneically in a patient without introducing intact cells that could trigger rejection, or other adverse immunological responses. Conditioned medium is prepared by culturing cells in a culture medium, then removing the cells from the medium.

Conditioned medium prepared from populations of umbilical cord-derived cells may be used as is, further concentrated, for example, by ultrafiltration or lyophilization, or even dried, partially purified, combined with pharmaceutically acceptable carriers or diluents as are known in the art, or combined with other compounds such as biologicals, for example, pharmaceutically useful protein compositions. Conditioned medium may be used in vitro or in vivo, alone or combined with autologous or syngeneic live cells, for example. The conditioned medium, if introduced in vivo, may be introduced locally at a site of treatment, or remotely to provide needed cellular growth or trophic factors to a patient.

In another embodiment, an extracellular matrix (ECM) produced by culturing the UTC on liquid, solid or semi-solid substrates is prepared, collected and utilized as an alternative to implanting live cells into a subject in need of tissue repair or replacement. The UTC is cultured in vitro, on a three dimensional framework as described elsewhere herein, under conditions such that a desired amount of ECM is secreted onto the framework. The cells comprising the new tissue are removed, and the ECM processed for further use, for example, as an injectable preparation. To accomplish this, cells on the framework are killed and any cellular debris is removed from the framework. This process may be carried out in a number of different ways. For example, the living tissue can be flash-frozen in liquid nitrogen without a cryopreservative, or the tissue can be immersed in sterile distilled water so that the cells burst in response to osmotic pressure.

Once the cells have been killed, the cellular membranes may be disrupted and cellular debris removed by treatment with a mild detergent rinse, such as EDTA, CHAPS or a zwitterionic detergent. Alternatively, the tissue can be enzymatically digested and/or extracted with reagents that break down cellular membranes and allow removal of cell contents. Examples of such enzymes include, but are not limited to, hyaluronidase, dispase, proteases, and nucleases. Examples of detergents include non-ionic detergents such as, for example, alkylaryl polyether alcohol (TRITON X-100), octylphenoxy polyethoxy-ethanol (Rohm and Haas, Philadelphia, Pa.), BRIJ-35, a polyethoxyethanol lauryl ether (Atlas Chemical Co., San Diego, Calif.), polysorbate 20 (TWEEN 20), a polyethoxyethanol sorbitan monolaureate (Rohm and Haas, Philadelphia, Pa.), polyethylene lauryl ether (Rohm and Haas, Philadelphia, Pa.); and ionic detergents such as sodium dodecyl sulfate, sulfated higher aliphatic alcohols, sulfonated alkanes and sulfonated alkylarenes containing 7 to 22 carbon atoms in a branched or unbranched chain.

The collection of the ECM can be accomplished in a variety of ways, depending at least in part on whether the new tissue has been formed on a three-dimensional framework that is biodegradable or non-biodegradable, as in the case of metals. For example, if the framework is non-biodegradable, the ECM can be removed by subjecting the framework to sonication, high pressure water jets, mechanical scraping, or mild treatment with detergents or enzymes, or any combination of the above.

If the framework is biodegradable, the ECM can be collected, for example, by allowing the framework to degrade or dissolve in solution. Alternatively, if the biodegradable framework is composed of a material that can itself be injected along with the ECM, the framework and the ECM can be processed in toto for subsequent injection. Alternatively, the ECM can be removed from the biodegradable framework by any of the methods described above for collection of ECM from a non-biodegradable framework. All collection processes are preferably designed so as not to denature the ECM.

After it has been collected, the ECM may be processed further. For example, the ECM can be homogenized to fine particles using techniques well known in the art such as by sonication, so that it can pass through a surgical needle. The components of the ECM can also be crosslinked, if desired, by gamma irradiation. Preferably, the ECM can be irradiated between 0.25 to 2 mega rads to sterilize and crosslink the ECM. Chemical crosslinking using agents that are toxic, such as glutaraldehyde, is possible but not generally preferred.

The amounts and/or ratios of proteins, such as the various types of collagen present in the ECM, may be adjusted by mixing the ECM produced by the cells of the invention with ECM of one or more other cell types. In addition, biologically active substances such as proteins, growth factors and/or drugs, can be incorporated into the ECM. Exemplary biologically active substances include tissue growth factors, such as TGF-beta, and the like, which promote healing and tissue repair at the site of the injection. Such additional agents may be utilized in any of the embodiments described herein above, e.g., with whole cell lysates, soluble cell fractions, or further purified components and products produced by the UTC.

In another aspect, the invention provides pharmaceutical compositions that utilize the UTC, UTC populations, components and products of the UTC in various methods for the treatment of injury or damage caused by a peripheral ischemic episode. Certain embodiments encompass pharmaceutical compositions comprising live cells (UTC alone or admixed with other cell types). Other embodiments encompass pharmaceutical compositions comprising UTC cellular components (e.g., cell lysates, soluble cell fractions, conditioned medium, ECM, or components of any of the foregoing) or products (e.g., trophic and other biological factors produced naturally by the UTC or through genetic modification, conditioned medium from UTC culture). The UTC components and products that can be used in the present invention are described in U.S. Patent Publication Nos. 2005/0032209, 2005/0058631 and 2005/0054098, and are incorporated herein by reference. In either case, the pharmaceutical composition may further comprise other active agents, such as anti-inflammatory agents, anti-apoptotic agents, antioxidants, growth factors, myotrophic factors or myoregenerative or myoprotective drugs as known in the art.

Pharmaceutical compositions comprising UTC live cells are typically formulated as liquids, semisolids (e.g., gels) or solids (e.g., matrices, scaffolds and the like, as appropriate for vascular or lung tissue engineering). Liquid compositions are formulated for administration by any acceptable route known in the art to achieve delivery of live cells to the target vascular or lung tissues. Typically, these include injection or infusion, either in a diffuse fashion, or targeted to the site of lung injury, damage, or distress, by a route of administration including, but not limited to, intramuscular, intravenous, or intra-arterial delivery via syringes with needles and/or catheters with or without pump devices.

Pharmaceutical compositions comprising live cells in a semi-solid or solid carrier are typically formulated for surgical implantation at the site of lung injury, damage, or distress. It will be appreciated that liquid compositions also may be administered by surgical procedures. In particular embodiments, semi-solid or solid pharmaceutical compositions may comprise semi-permeable gels, lattices, cellular scaffolds and the like, which may be non-biodegradable or biodegradable. For example, in certain embodiments, it may be desirable or appropriate to sequester the exogenous cells from their surroundings, yet enable the cells to secrete and deliver biological molecules (e.g. myotrophic factors, angiotrophic factors, or endothelial progenitor cell recruitment factors) to surrounding lung tissue or vascular cells. In these embodiments, cells may be formulated as autonomous implants comprising a living UTC or cell population comprising a UTC surrounded by a non-degradable, selectively permeable barrier that physically separates the transplanted cells from host tissue. Such implants are sometimes referred to as "immunoprotective," as they have the capacity to prevent immune cells and macromolecules from killing the transplanted cells in the absence of pharmacologically induced immunosuppression.

In other embodiments, different varieties of degradable gels and networks are utilized for the pharmaceutical compositions of the invention. For example, degradable materials particularly suitable for sustained release formulations include biocompatible polymers, such as poly(lactic acid), poly (lactic acid-co-glycolic acid), methylcellulose, hyaluronic acid, collagen, and the like.

In other embodiments, it may be desirable or appropriate to deliver the cells on or in a biodegradable, preferably bioresorbable or bioabsorbable, scaffold or matrix. These, typically three-dimensional, biomaterials contain the living cells attached to the scaffold, dispersed within the scaffold, or incorporated in an extracellular matrix entrapped in the scaffold. Once implanted into the target region of the body, these implants become integrated with the host tissue, wherein the transplanted cells gradually become established. (See, e.g., Tresco, P A, et al., *Adv. Drug Delivery Rev.,* 2000; 42:3-27; see also, Hutmacher, D W, *J. Biomater. Sci. Polymer Edn.,* 2001; 12:107-174).

The biocompatible matrix may be comprised of natural, modified natural or synthetic biodegradable polymers, including homopolymers, copolymers and block polymers, as well as combinations thereof. It is noted that a polymer is generally named based on the monomer from which it is synthesized.

Examples of suitable biodegradable polymers or polymer classes include fibrin, collagen, elastin, gelatin, vitronectin, fibronectin, laminin, thrombin, poly(aminoacid), oxidized cellulose, tropoelastin, silk, ribonucleic acids, deoxyribonucleic acids, proteins, polynucleotides, reconstituted basement membrane matrices, starches, dextrans, alginates, hyaluron, chitin, chitosan, agarose, polysaccharides, hyaluronic acid, poly(lactic acid), poly(glycolic acid), polyethylene glycol, decellularized tissue, self-assembling peptides, polypeptides, glycosaminoglycans, their derivatives and mixtures thereof. For both glycolic acid and lactic acid, an intermediate cyclic dimer is typically prepared and purified prior to polymerization. These intermediate dimers are called glycolide and lactide, respectively. Other useful biodegradable polymers or polymer classes include, without limitation, aliphatic polyesters, poly(alkylene oxalates), tyrosine derived polycarbonates, polyiminocarbonates, polyorthoesters, polyoxaesters, polyamidoesters, polyoxaesters containing amine groups, poly(propylene fumarate), polydioxanones, polycarbonates, polyoxalates, poly(alpha-hydoxyacids), poly(esters), polyurethane, poly(ester urethane), poly(ether urethane), polyanhydrides, polyacetates, polycaprolactones, poly(orthoesters), polyamino acids, polyamides and blends and copolymers thereof. Additional useful biodegradable polymers include, without limitation, stereopolymers of L- and D-lactic acid, copolymers of bis(para-carboxyphenoxy) propane and sebacic acid, sebacic acid copolymers, copolymers of caprolactone, poly (lactic acid)/poly(glycolic acid)/polyethyleneglycol copolymers, copolymers of polyurethane and poly(lactic acid), copolymers of alpha-amino acids, copolymers of alpha-amino acids and caproic acid, copolymers of alpha-benzyl glutamate and polyethylene glycol, copolymers of succinate and poly(glycols), polyphosphazene, poly(hydroxyalkanoates) and mixtures thereof. Binary and ternary systems also are contemplated.

In general, a suitable biodegradable polymer for use as the matrix is desirably configured so that it: (1) has mechanical properties that are suitable for the intended application; (2) remains sufficiently intact until tissue has in-grown and healed; (3) does not invoke an inflammatory or toxic response; (4) is metabolized in the body after fulfilling its purpose; (5) is easily processed into the desired final product to be formed; (6) demonstrates acceptable shelf-life; and (7) is easily sterilized.

In one aspect of the invention, the biocompatible polymer used to form the matrix is in the form of a hydrogel. In general, hydrogels are cross-linked polymeric materials that can absorb more than 20% of their weight in water while maintaining a distinct three-dimensional structure. This definition includes dry cross-linked polymers that will swell in aqueous environments, as well as water-swollen materials. A host of hydrophilic polymers can be cross-linked to produce hydrogels, whether the polymer is of biological origin, semi-synthetic, or wholly synthetic. The hydrogel may be produced from a synthetic polymeric material. Such synthetic polymers can be tailored to a range of properties and predictable lot-to-lot uniformity, and represent a reliable source of material that generally is free from concerns of immunogenicity. The matrices may include hydrogels formed from self assembling peptides, such as those discussed in U.S. Pat. Nos. 5,670,483 and 5,955,343, U.S. Patent Application No. 2002/0160471, and PCT Application No. WO 02/062969.

Properties that make hydrogels valuable in drug delivery applications include the equilibrium swelling degree, sorption kinetics, solute permeability, and their in vivo performance characteristics. Permeability to compounds depends in part upon the swelling degree or water content and the rate of biodegradation. Since the mechanical strength of a gel declines in direct proportion to the swelling degree, it is also well within the contemplation of the present invention that the hydrogel can be attached to a substrate so that the composite system enhances mechanical strength. In some embodiments, the hydrogel can be impregnated within a porous substrate, so as to gain the mechanical strength of the substrate, along with the useful delivery properties of the hydrogel.

Non-limiting examples of scaffold or matrix (sometimes referred to collectively as "framework") that may be used in the present invention include textile structures such as weaves, knits, braids, meshes, non-wovens, and warped knits; porous foams, semi-porous foams, perforated films or sheets, microparticles, beads, and spheres and composite structures being a combination of the above structures. Non-woven mats may, for example, be formed using fibers comprised of a synthetic absorbable copolymer of glycolic and lactic acids (PGA/PLA), sold under the tradename VICRYL sutures (Ethicon, Inc., Somerville, N.J.). Foams, composed of, for example, poly(epsilon-caprolactone)/poly (glycolic acid) (PCL/PGA) copolymer, formed by processes such as freeze-drying, or lyophilization, as discussed in U.S. Pat. No. 6,355,699, also may be utilized. Hydrogels such as self-assembling peptides (e.g., RAD 16) may also be used. In situ-forming degradable networks are also suitable for use in the invention. (See, e.g., Anseth, K S et al., *J. Controlled Release*, 2002; 78:199-209; Wang, D. et al., *Biomaterials*, 2003; 24:3969-3980; U.S. Patent Publication 2002/0022676). These in situ forming materials are formulated as fluids suitable for injection, then may be induced to form a hydrogel by a variety of means such as change in temperature, pH, and exposure to light in situ or in vivo.

In another embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another embodiment, cells are seeded onto foam scaffolds that may be composite structures.

In many of the above mentioned embodiments, the framework may be molded into a useful shape, such as that of a blood vessel. Furthermore, it will be appreciated that UTC may be cultured on pre-formed, non-degradable surgical or implantable devices, e.g., in a manner corresponding to that used for preparing fibroblast-containing GDC endovascular coils, for instance. (Marx, W F, et al., *Am. J. Neuroradiol.*, 2001; 22:323-333).

The matrix, scaffold or device may be treated prior to the inoculation of cells in order to enhance cell attachment. For example, prior to inoculation, nylon matrices can be treated with 0.1 molar acetic acid and incubated in polylysine, PBS, and/or collagen to coat the nylon. Polystyrene can be similarly treated using sulfuric acid. The external surfaces of a framework may also be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), genetic materials such as cytokines and growth factors, a cellular matrix, and/or other materials, including, but not limited to, gelatin, alginates, agar, agarose, and plant gums, among other factors affecting cell survival and differentiation.

UTC-containing frameworks are prepared according to methods known in the art. For example, cells can be grown freely in a culture vessel to sub-confluency or confluency, lifted from the culture and inoculated onto the framework. Growth factors may be added to the culture medium prior to, during, or subsequent to inoculation of the cells to trigger differentiation and tissue formation, if desired. Alternatively, the frameworks themselves may be modified so that the growth of cells thereon is enhanced, or so that the risk of rejection of the implant is reduced. Thus, one or more biologically active compounds, including, but not limited to, anti-inflammatory compounds, immunosuppressants or growth factors, may be added to the framework for local release.

A UTC, parts of a UTC, or cell populations comprising a UTC, or components of or products produced by a UTC, may be used in a variety of ways to support and facilitate the repair, regeneration, and improvement of lung cells and tissues, to improve blood flow, and to stimulate and/or support angiogenesis, especially in lung disease patients. Such utilities encompass in vitro, ex vivo and in vivo methods.

In one embodiment, as discussed above, the UTC can be cultured in vitro to produce biological products that are either naturally produced by the cells, or produced by the cells when induced to differentiate into lung tissue, or produced by the cells via genetic modification. For instance, TIMP1, TPO, KGF, HGF, FGF, HBEGF, BDNF, MIP1b, MCPJ, RANTES, 1309, TARC, MDC, and IL-8 were found to be secreted from umbilicus-derived cells grown in growth medium. (See Examples). In addition, factors for endothelial progenitor cell recruitment such as VEGF, SDF-1, EPO, G-CSF, statins, estrogen, PPAR-γ, and CXCR4 may be produced by the UTC and may be secreted into the growth medium. Other trophic factors, as yet undetected or unexamined, of use in lung tissue or vascular repair and regeneration, are likely to be produced by the UTC and possibly secreted into the medium.

In this regard, another embodiment of the invention features use of the UTC for production of conditioned medium, either from an undifferentiated UTC or from a UTC incubated under conditions that stimulate differentiation into a lung tissue or vascular lineage. Such conditioned media are contemplated for use in in vitro or ex vivo culture of lung tissue precursor cells, or in vivo to support transplanted cells comprising homogeneous populations of a UTC or heterogeneous populations comprising a UTC and lung tissue or vascular progenitors, or to recruit endothelial progenitor cells to the site of lung injury, for example.

Yet another embodiment comprises the use of UTC cell lysates, soluble cell fractions or components thereof, or ECM or components thereof, for a variety of purposes. As mentioned above, some of these components may be used in pharmaceutical compositions. In other embodiments, a cell lysate or ECM is used to coat or otherwise treat substances or devices to be used surgically, or for implantation, or for ex vivo purposes, to promote healing or survival of cells or tissues contacted in the course of such treatments. In some preferred embodiments, such preparations made from a UTC comprise FGF and HGF.

In another embodiment, a UTC is used advantageously in co-cultures in vitro to provide trophic support to other cells, in particular, lung tissue cells, for example skeletal muscle progenitor cells, vascular smooth muscle cells, vascular smooth muscle progenitor cells, pericytes, vascular endothelial cells, or vascular endothelium progenitor cells. In some preferred embodiments, the trophic support is proliferation of the cells. For co-culture, it may be desirable for the UTC and the desired other cells to be co-cultured under conditions in which the two cell types are in contact. This can be achieved, for example, by seeding the cells as a heterogeneous population of cells in culture medium or onto a suitable culture substrate. Alternatively, the UTC can first be grown to confluence, and then will serve as a substrate for the second desired cell type in culture. In this latter embodiment, the cells may further be physically separated, e.g., by a membrane or similar device, such that the other cell type may be removed and used separately, following the co-culture period. Use of the UTC in co-culture to promote expansion and differentiation of lung tissue or vascular cell types may find applicability in research and in clinical/therapeutic areas. For instance, UTC co-cultures may be utilized to facilitate growth and differentiation of lung tissue, for example, vascular smooth muscle, pericytes, or vascular endothelial cells, in culture, for basic research purposes or for use in drug screening assays, for example. UTC co-cultures may also be utilized for ex vivo expansion of, for example, vascular smooth muscle, pericyte, or vascular endothelium progenitors for later administration for therapeutic purposes. Lung tissue, for example, vascular smooth muscle, pericyte, or vascular endothelium progenitor cells, may be harvested from an individual, expanded ex vivo in co-culture with UTC, then returned to that individual (autologous transfer) or another individual (syngeneic or allogeneic transfer). In these embodiments, it will be appreciated that, following ex vivo expansion, the mixed population of cells comprising the UTC and lung tissue, for example, vascular smooth muscle, pericyte, or vascular endothelium progenitors, could be administered to a patient in need of treatment. Alternatively, in situations where autologous transfer is appropriate or desirable, the co-cultured cell populations may be physically separated in culture, enabling removal of the autologous lung tissue, for example vascular smooth muscle, or vascular endothelium progenitors, for administration to the patient.

As described in US Patent Publication Nos. 2005/0032209, 2005/0058631, 2005/0054098 and 2005/0058630, UTC, and components and products thereof, have been shown to be effectively transplanted into the body, and to improve blood flow and reduce tissue necrosis in an accepted animal model. Those findings, along with the discoveries set forth in the present invention, support preferred embodiments of the invention, wherein the UTC is used in cell therapy for treating lung injury or damage by repairing or regenerating lung tissue and/or vascular tissue in a lung damaged patient, or by improving blood flow or stimulating and/or supporting angiogenesis in a lung damaged patient. In one embodiment, the UTC is transplanted into a target location in the body, especially at or proximal to the location of the lung damage, where the UTC can differentiate into one or more of lung tissue phenotypes, for example, vascular smooth muscle, pericyte, or vascular endothelium phenotypes, the UTC can provide trophic support for lung tissue, for example, vascular smooth muscle cell, pericyte, or vascular endothelial cell progenitors and/or lung tissue cells. In situ, the UTC can produce factors to recruit endothelial progenitor cells to the site of the lung injury, or the UTC can exert a beneficial effect in two or more of those fashions, among others. The UTC secretes trophic factors including, but not limited to GFGFm, IL-6, IL-8, HGF, IGF-1, TPO, and the like. The UTC can aid in the recruitment of vascular progenitor cells such as angioblasts to stimulate new blood vessel formation.

The UTC can exert trophic effects in the body of the patient to which they are administered. For example, the UTC can exert trophic effects on lung tissue cells, for example, vascular smooth muscle cells, vascular endothelial cells, pericytes, or progenitor cells, thereof. In some preferred embodiments, the trophic effect is the proliferation of such cells. The UTC can also induce migration of cells in the body of the patient to which they are administered. Such migration can facilitate the repair, regeneration, and treatment of lung disease, disorders, and/or injuries, such as COPD, ALI, ARDS, and pulmonary fibrosis. For example, a UTC administered at or near a site of lung damage can induce migration of cells to the site of lung damage in order to repair, regenerate, or otherwise treat the diseased tissue and its surroundings. The UTC so administered can induce migration of lung tissue cells, for example, vascular smooth muscle cells, vascular endothelial cells, pericytes, or progenitor cells, thereof. In preferred embodiments, the UTC induces migration of vascular endothelial cells and/or vascular endothelium progenitor cells to the site, or at least near to the site of the lung damage. In some embodiments, migration is induced or supported by FGF and/or HGF, preferably FGF and HGF expressed by the UTC. Preparations made from the UTC, including cell lysates, subcellular fractions, products, and the like, can also be used to treat lung disease, disorders and/or injuries. Such preparations can be formulated with pharmaceutically acceptable carriers such as those described and exemplified herein, and administered to patients in amounts effective to treat lung disease, disorders and/or injuries. In preferred embodiments, preparations made from the UTC comprise FGF and HGF.

Specific embodiments of the invention are directed to the direct repair, regeneration or replacement of, or the support of the repair, regeneration, or replacement of, blood vessels for the treatment of lung injury or damage.

The UTC may be administered alone (e.g., as substantially homogeneous populations) or as admixtures with other cells. As described above, the UTC may be administered as formulated in a pharmaceutical preparation with a matrix or scaffold, or with conventional pharmaceutically acceptable carriers. Where the UTC is administered with other cells, they may be administered simultaneously or sequentially with the other cells (either before or after the other cells). Cells that may be administered in conjunction with the UTC include, but are not limited to, myocytes, lung tissue cells, skeletal muscle progenitor cells, vascular smooth muscle cells, vascular smooth muscle progenitor cells, pericytes, vascular endothelial cells, or vascular endothelium progenitor cells, and/or other multipotent or pluripotent stem cells. The cells of different types may be admixed with the UTC immediately or shortly prior to administration, or they may be co-cultured together for a period of time prior to administration.

The UTC may be administered with other beneficial drugs or biological molecules, or other active agents, such as anti-inflammatory agents, anti-apoptotic agents, antioxidants, growth factors, angiogenic factors, or myoregenerative or myoprotective drugs as known in the art. When the UTC is administered with other agents, they may be administered together in a single pharmaceutical composition, or in separate pharmaceutical compositions, simultaneously or sequentially with the other agents (either before or after administration of the other agents). The other agents may be a part of a treatment regimen that begins either before transplantation and continuing throughout the course of recovery, or may be initiated at the time of transplantation, or even after transplantation, as a physician of skill in the art deems appropriate.

In one embodiment, the UTC is administered as undifferentiated cells, i.e., as cultured in growth medium. Alternatively, the UTC may be administered following exposure in culture to conditions that stimulate differentiation toward a desired lung tissue phenotype, for example, vascular smooth muscle, pericyte, or vascular endothelium phenotypes.

The cells of the invention may be surgically implanted, injected, delivered (e.g., by way of a catheter, syringe, shunt, stent, microcatheter, or pump), or otherwise administered directly or indirectly to the site of lung injury, damage, or distress. Routes of administration of the cells of the invention, or compositions thereof, include, but are not limited to, intravenous, intramuscular, subcutaneous, intranasal, intrathecal, intracisternal, or via syringes with needles or catheters with or without pump devices.

When cells are administered in semi-solid or solid devices, surgical implantation into a precise location in the body is typically a suitable means of administration. Liquid or fluid pharmaceutical compositions, however, may be administered through the blood, or directly into affected lung tissue (e.g., throughout a diffusely affected area, such as would be the case for diffuse ALI or ARDS). The migration of the UTC can be guided by chemical signals, growth factors, or calpains.

The umbilical cord tissue-derived cells, or compositions and/or matrices comprising the umbilical cord tissue-derived cells, may be delivered to the site via a micro catheter, intracatheterization, or via a mini-pump. The vehicle excipient or carrier can be any of those known to be pharmaceutically acceptable for administration to a patient, particularly locally at the site at which cellular differentiation is to be induced. Examples include liquid media, for example, Dulbeccos Modified Eagle's Medium (DMEM), sterile saline, sterile phosphate buffered saline, Leibovitz's medium (L15, Invitrogen, Carlsbad, Calif.), dextrose in sterile water, and any other physiologically acceptable liquid.

Other embodiments encompass methods of treating lung injury or damage by administering therapeutic compositions comprising a pharmaceutically acceptable carrier and UTC cellular components (e.g., cell lysates or components thereof) or products (e.g., trophic and other biological factors produced naturally by the UTC or through genetic modification, conditioned medium from UTC culture), or UTC growth medium or products purified from growth medium. In preferred embodiments, the biological factors are FGF and HGF. These methods may further comprise administering other active agents, such as growth factors, angiogenic factors or myoregenerative or myoprotective drugs as known in the art.

Dosage forms and regimes for administering the UTC or any of the other therapeutic or pharmaceutical compositions described herein are developed in accordance with good medical practice, taking into account the condition of the individual patient, e.g., nature and extent of the injury or damage from the lung damaging event, age, sex, body weight and general medical condition, and other factors known to medical practitioners. Thus, the effective amount of a pharmaceutical composition to be administered to a patient is determined by these considerations as known in the art.

The UTC has been shown not to stimulate allogeneic PBMCs in a mixed lymphocyte reaction. Accordingly, allogeneic, or even xenogeneic, transplantation of UTC may be tolerated in some instances. In some embodiments, the UTC itself provides an immunosuppressant effect, thereby preventing host rejection of the transplanted UTC. In such instances, pharmacological immunosuppression during cell therapy may not be necessary.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device, as described above. These and other means for reducing or eliminating an immune response to the transplanted cells are known in the art. As an alternative, the UTC may be genetically modified to reduce their immunogenicity, as mentioned above.

Survival of the transplanted UTC in a living patient can be determined through the use of a variety of scanning techniques, e.g., computerized axial tomography (CAT or CT) scan, magnetic resonance imaging (MRI) or positron emission tomography (PET) scans. Determination of transplant survival can also be done post mortem by removing the lung tissue or vascular tissue, and examining it visually or through a microscope. Alternatively, cells can be treated with stains that are specific for lung tissue cells, for example, vascular smooth muscle cells, pericytes, or vascular endothelial cells. Transplanted cells can also be identified by prior incorporation of tracer dyes such as rhodamine- or fluorescein-labeled microspheres, fast blue, ferric microparticles, bisbenzamide or genetically introduced reporter gene products, such as beta-galactosidase or beta-glucuronidase.

In another aspect, the invention provides kits that utilize the UTC, UTC populations, components and products of the UTC in various methods for stimulating and/or supporting angiogenesis, for improving blood flow, for regenerating, repairing, and improving lung tissue injured or damaged by a lung damaging event, as described above. Where used for treatment of damage or injury caused by a lung disease, disorders and/or injuries, or other scheduled treatment, the kits may include one or more cell populations, including at least the UTC and a pharmaceutically acceptable carrier (liquid, semi-solid or solid). The kits also optionally may include a means of administering the cells, for example by injection. The kits further may include instructions for use of the cells. Kits prepared for field hospital use, such as for military use, may include full-procedure supplies including tissue scaffolds, surgical sutures, and the like, where the cells are to be used in conjunction with repair of acute injuries. Kits for assays and in vitro methods as described herein may contain one or more of (1) a UTC or components or products of the UTC, (2) reagents for practicing the in vitro method, (3) other cells or cell populations, as appropriate, and (4) instructions for conducting the in vitro method.

The following examples describe several aspects of embodiments of the invention in greater detail. These examples are intended to further illustrate aspects of the invention described herein. These examples should not be construed to limit the aspect so exemplified.

Example 1

Pulmonary Protective Efficacy in a Mouse Model of Hyperoxia-Induced Acute Lung Injury This example illustrates the effectiveness of human UTC (hUTC) (isolation and characterization of hUTC may be found at Examples 5-15) to enhance lung repair and regeneration in a model of hyperoxia induced lung injury.

Umbilical Cell Culture and Isolation

Umbilicus-derived cells (UDC, hUTC) were prepared as described in U.S. Patent Publication Nos. 2005/0032209, 2005/0058631 and 2005/0054098. Cells were cultured to the desired passage and then cryogenically preserved.

Animal Model

Female C57BL/6 mice (seven weeks of age) were obtained from Ace Animals (Boyertown, Pa.). Immediately prior to injection, hUTC were thawed at 37° C. (water bath) and washed two times in phosphate buffered saline (PBS) and resuspended in lmL of PBS. Cells were counted using a hemocytometer. Cell viability was determined by trypan blue dye exclusion. Cells were reconstituted at a concentration of $1\times10^6$ cells in 200 µl PBS.

The study outline is summarized in Table 1-1 below. On Day 0, cells ($1\times10^6$ hUTC in 200 µl PBS) or PBS vehicle were slowly administered to mice by intravenous tail vein injection using a lmL syringe and a 26-gauge needle and animals were then exposed to either room air or 90% $O_2$. Exposure to 90% $O_2$ was accomplished by placing the animals into a BioSpherix chamber (BioSpherix, LTD, Lacona, N.Y.) that has been primed and equilibrated to 90% $O_2$ for 1 hr. Supportive care (heat support and NutriCal) was provided daily for these animals. Animal observations, mortality, survival, and percent oxygen concentrations for each tank were recorded two times a day. On day four post treatment, animals were euthanized using 50 mg/mL Nembutal (pentobarbital).

TABLE 1-1

Experimental design.

| Treatment group | Atmospheric treatment | Treatment | Number of animals |
|---|---|---|---|
| 1 | Room Air | PBS | 12 |
| 2 | 90% $O_2$ | PBS | 12 |
| 3 | 90% $O_2$ | $1e^6$ hUTC | 12 |

Bronchoalveolar Lavage Fluid (BALF) Total Protein Analysis

To determine the total protein in each sample, cell free BALF was analyzed using a BCA Protein Assay (Pierce). Analysis was completed using the Softmax 4.0 program and data was graphed using Graph Pad Prism Software.

BALF and Lung Homogenate Cytokines/Chemokine Analysis

To prepare BALF, 6 animals per treatment group were euthanized and lungs were lavaged once with 1.0 mL sterile PBS (Invitrogen) and the tubes were placed on wet ice. The BALF was centrifuged at 1000 rpm for 5 min and the supernatant fluid was removed and used for further analysis.

To prepare lung homogenates, 6 animals per group were euthanized, subjected to whole body perfusion with PBS and the left lungs were dissected and placed on ice in Lysing Matrix D tubes and then centrifuged in a FastPrep instrument at a speed of 4.0 for 40 seconds.

Cytokine/chemokine levels in both BALF and lung homogenate supernatant were determined using a mouse 22-multiplex bead kit (Millipore) following the manufacturer's protocol and analyzed using the BioRad Bioplex machine. The results were graphed and analyzed using GraphPad Prism Software.

Human Cell Detection

Total RNA was isolated from mouse tissues by Asuragen, Inc., according to the company's standard operating procedures. The purity and quantity of total RNA samples were determined by absorbance readings at 260 and 280 nm using a NanoDrop ND-1000 UV spectrophotometer. RNA integrity was evaluated using an Agilent Bioanalyzer.

Human-specific assays for GAPDH mRNA (Hs99999905_m1_GAPDH) were used to estimate the number of hUTC within mouse lung tissue. Samples for quantitative RT-PCR (qRT-PCR) analysis using single-tube Taq-Man® Assays (Applied Biosystems) were processed by Asuragen, Inc., according to the company's standard operating procedures. Dilutions of total RNA was reverse transcribed using the TagMan® High Capacity cDNA Synthesis Kit (Applied Biosystems) according to the manufacturer's instructions and in a total reaction volume of 20 microliters per dilution. 50 ng input cDNA was then analyzed by PCR. All amplifications were performed in triplicate on a validated ABI 7500 real-time thermocycler. Following incubation at 95° C. for 10 minutes, samples were amplified in 40 cycles of 95° C. for 15 seconds, then 60° C. for 1 minute. Total number of hUTC within the mouse lungs was estimated based on a standard curve generated by analyzing known amounts of purified hUTC total RNA.

BALF Total Protein

Figure 1:
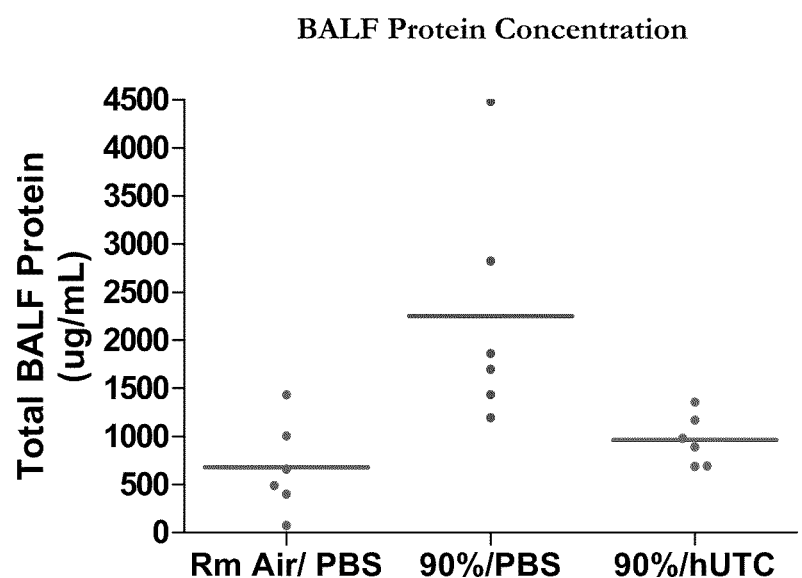
FIG. 1 shows the BALF total protein concentration: Total protein was measured using a Pierce BCA Protein Assay.

Exposure to 90% $O_2$ for 4 days resulted in an increase in the total protein content of BALF compared to room air control animals (p<0.01, FIG. 1, Table 1-2). Furthermore, there was a statistically significant decrease in the total BALF protein in the 90% $O_2$ hUTC treatment group as compared to the 90% $O_2$ PBS treatment group (p<0.05).

TABLE 1-2

BALF total protein concentration: Total protein was measured using Pierce BCA Protein Assay.

| Treatment Group | Animal number | Total BALF protein Concentration (ug/dl) |
|---|---|---|
| 1 | 1 | 401.89 |
| 1 | 2 | 1006.68 |
| 1 | 3 | 660.67 |
| 1 | 4 | 494.49 |
| 1 | 5 | 1432.64 |
| 1 | 6 | 76.23 |
| Mean: | | 678.77 |
| Stdev: | | 437.77 |

TABLE 1-2-continued

BALF total protein concentration: Total protein was measured using Pierce BCA Protein Assay.

| Treatment Group | Animal number | Total BALF protein Concentration (ug/dl) |
|---|---|---|
| 2 | 1 | 1701.60 |
| 2 | 2 | 1438.46 |
| 2 | 3 | 1197.13 |
| 2 | 4 | 2823.95 |
| 2 | 5 | 4482.76 |
| 2 | 6 | 3174.32 |
| Mean: | | 2469.70 |
| Stdev: | | 1260.74 |
| 3 | 1 | 984.87 |
| 3 | 2 | 691.20 |
| 3 | 3 | 1172.41 |
| 3 | 4 | 893.28 |
| 3 | 5 | 695.56 |
| 3 | 6 | 1359.95 |
| Mean: | | 966.21 |
| Stdev: | | 265.37 |

BALF and Lung Homogenate Cytokine Analysis

A statistically significant decrease in BALF keratinocyte factor (KC), gamma interferon-inducible cytokine (IP-10), interleukin 1α (IL-1α) and lung homogenate monocyte chemotactic factor-1 (MCP-1) was observed in animals treated with hUTC and exposed to 90% $O_2$ compared to animals treated with PBS vehicle and exposed to 90% $O_2$ ($p<0.02$). (FIGS. 2a and 2b, FIGS. 3 and 4).

Human Cell Engraftment

On day four, post treatment, animals were sacrificed, lungs were harvested and total RNA was isolated for human cell detection. Results showed the presence of hUTC within the lungs of hUTC treated animals, but absent from the lungs of PBS treated animals (Table 1-3).

TABLE 1-3

Human cell detection. The presence of hUTC within mouse lungs at day four-post treatment was determined by measuring human specific GAPDH mRNA transcripts using real-time PCR. Cycle threshold (CT) values less than 34 indicate that hUTC are present within the mouse lung tissue. No hUTC mRNA transcripts detected within mouse lung tissue (Absent). hUTC mRNA transcripts detected within mouse lung tissue (Present).

| Treatment group | Average CT value | HUTC within mouse lung |
|---|---|---|
| 1 | 36.1 | Absent |
| 1 | 36.5 | Absent |
| 2 | 34.9 | Absent |
| 2 | 34.4 | Absent |
| 3 | 26.2 | Present |
| 3 | 29.6 | Present |
| 3 | 26.6 | Present |
| 3 | 26.9 | Present |
| 3 | 26.1 | Present |
| 3 | 26.5 | Present |

The effect of prophylactic intravenous administration of hUTC on the development of hyperoxia induced acute lung injury in mice was evaluated. The reduced level of total protein in the BALF, following hUTC administration in mice exposed to 90% O2, suggests that hUTC were able to reduce hyperoxia induced vascular leak/edema in the lung. In addition, data showed that hUTC caused a reduction in the levels of three important chemokines suggesting reduced inflammation in the lung. These data provide evidence that hUTC might be an important therapeutic agent for the treatment of lung disease.

Example 2

Therapeutic Efficacy in a Rodent Model of Chronic Obstructive Pulmonary Disease This example illustrates the effectiveness of hUTC to enhance lung repair and regeneration in a rodent model of cigarette smoke induced pulmonary injury. The data demonstrates the therapeutic value of hUTC for the preventive treatment of COPD.

Umbilical Cell Culture and Isolation

Umbilicus-derived cells (UDCs, hUTCs) were prepared as described in U.S. Patent Publication Nos. 2005/0032209, 2005/0058631 and 2005/0054098. Cells were cultured to the desired passage and then cryogenically preserved.

Animal Model

Healthy, male, 12 to 15-weeks old, SH rats will be purchased from Charles River Laboratories, Raleigh, N.C. Each rat strain will be randomized by body weight into three groups (Table 2-1). SD rats will then be exposed whole-body to tobacco smoke (total particulate concentration 75-85 mg/m(3)) or filtered room air for 6 h/day for 15 days (3 days/wk).

Dose Preparation

On day 15, smoking treatment will be terminated and hUTC or PBS vehicle will be administered. Immediately prior to injection, hUTC will be thawed at 37° C. (water bath), washed two times in phosphate buffered saline (PBS) and resuspended in 1 mL of PBS. Cells will be counted using a hemocytometer. Cell viability will be determined by trypan blue dye exclusion. Cells will be reconstituted at the appropriate concentrations of $1e^6$ cells and $3e^6$ cells in 2 mL of PBS. Cells will be slowly administered via tail vein injection over a two-minute interval.

Two weeks after vehicle or hUTC injections, the animals will be sacrificed to harvest bronchoalveolar lavage fluid (BALF) (8 animals/treatment group) and lung tissue (8 animals/treatment group).

TABLE 2-1

Experimental design.

| Treatment Group | Atmosphere | Time of Administration | Treatment |
|---|---|---|---|
| 1 | Room air | 0 | PBS |
| 2 | Smoke | 0 | PBS |
| 3 | Smoke | 0 | $1e^6$ hUTC |
| 4 | Smoke | 0 | $3e^6$ hUTC |

BALF Preparation

To prepare BALF, eight animals per treatment group will be euthanized and lungs will be lavaged once with 1.0 mL sterile PBS (Invitrogen) and the tubes containing fresh BALF will be placed on wet ice. The BALF will be centrifuged at 1000 rpm for 5 min and the supernatant fluid will be removed and used for further analysis.

BALF Cytokine Analysis

BALF cytokine/chemokine levels will be determined using a mouse 22-multiplex bead kit (Millipore) following the manufacturer's protocol and analyzed using the BioRad Bioplex machine. The results will be graphed and analyzed using GraphPad Prism Software.

BALF Total Protein Analysis

To determine the total protein in each sample, cell free BALF will be analyzed using a BCA Protein Assay (Pierce).

Analysis will be completed using the Softmax 4.0 program and data will be graphed using Graph Pad Prism Software.

Histology

Lungs will be harvested from eight animals per treatment group. Half of each lung will be fixed with 10% formaldehyde neutral buffer solution for 24 hours, dehydrated in a graded ethanol series, embedded in paraffin, and sliced at 5 μm. Paraffin sections will be stained with hematoxylin-eosin (HE) and Masson for histopathologic analysis. The remaining lung half will be snap frozen and processed for MPO and human cell detection (see below).

Myeloperoxidase (MPO) Activity

About 200 mg lung tissue from the right upper lobe will be homogenated in 20 mmol/L kalium phosphate buffer (pH7.4) and ultra-centrifuged. The precipitation will be preserved at −70° C. with HTAB for MPO measurement. The MPO activity will then be determined.

RNA Isolation

Total RNA will be isolated from all snap-frozen lung tissue by Asuragen, Inc., according to the company's standard operating procedures. The purity and quantity of total RNA samples will be determined by absorbance readings at 260 and 280 nm using a NanoDrop ND-1000 UV spectrophotometer. RNA integrity will be evaluated using an Agilent Bioanalyzer.

Human Cell Detection

Human-specific assays for GAPDH mRNA (Hs99999905_m1_GAPDH) will be used to estimate the number of hUTC within mouse lung tissue. Samples for quantitative RT-PCR (qRT-PCR) analysis using single-tube TaqMan® Assays (Applied Biosystems) will be processed by Asuragen, Inc., according to the company's standard operating procedures. Dilutions of total RNA will be reverse transcribed using the TagMan® High Capacity cDNA Synthesis Kit (Applied Biosystems) according to the manufacturer's instructions and in a total reaction volume of 20 microliters per dilution. 50 ng input cDNA will then be analyzed by PCR. All amplifications will be performed in triplicate on a validated ABI 7500 real-time thermocycler. Following incubation at 95° C. for 10 minutes, samples will be amplified in 40 cycles of 95° C. for 15 seconds, then 60° C. for 1 minute.

Example 3

Pulmonary Protective and Antifibrotic Effects in a Rodent Model of Pulmonary Fibrosis This example illustrates the effectiveness of hUTC to prevent fibrosis and enhance lung repair and regeneration in a rodent model of bleomycin (BLM) induced pulmonary fibrosis.

Umbilical Cell Culture and Isolation. Umbilicus-derived cells (UDC, hUTC) were prepared as described in U.S. Patent Publication Nos. 2005/0032209, 2005/0058631 and 2005/0054098. Cells were cultured to the desired passage and then cryogenically preserved.

Animal Model

Sixty-four adult Sprague-Dawley rats (200-250 g body weight) will be obtained and randomly divided into four groups with sixteen rats in each group. Animals will be perfused intratracheally with 5 mg/kg BLM. Immediately prior to injection, hUTC will be thawed at 37° C. (water bath), washed two times in phosphate buffered saline (PBS) and resuspended in 1 mL of PBS. Cells will be counted using a hemocytometer. Cell viability will be determined by trypan blue dye exclusion. Cells will be reconstituted at the appropriate concentrating in 2 mL of PBS. Cells will be slowly administered via tail vein injection over a two-minute interval. The study design is summarized in Table 3-1 below.

In the hUTC treatment groups, $0.1 \times 10^6$, $1 \times 10^6$ or $3 \times 10^6$ hUTC will be injected into the tail vein twelve hours after BLM perfusion. PBS vehicle alone will be administered in a similar fashion as in the hUTC treatment groups. Two weeks after vehicle or hUTC injections, the animals will be sacrificed to harvest bronchoalveolar lavage fluid (BALF) (8 animals/treatment group) and lung tissue (8 animals/treatment group).

TABLE 3-1

Experimental design.

| Treatment group | BLM (mg/kg) | Treatment |
| --- | --- | --- |
| 1 | 5 | PBS |
| 2 | 5 | $0.1e^6$ hUTC |
| 3 | 5 | $1e^6$ hUTC |
| 4 | 5 | $3e^6$ hUTC |

BALF Preparation

To prepare BALF, eight animals per treatment group will be euthanized and lungs will be lavaged once with 1.0 mL sterile PBS (Invitrogen) and the tubes containing fresh BALF will be placed on wet ice. The BALF will be centrifuged at 1000 rpm for 5 min and the supernatant fluid will be removed and used for further analysis.

BALF Cytokine Analysis

BALF cytokine/chemokine levels will be determined using a mouse 22-multiplex bead kit (Millipore) following the manufacturer's protocol and analyzed using the BioRad Bioplex machine. The results will be graphed and analyzed using GraphPad Prism Software.

BALF Total Protein Analysis

To determine the total protein in each sample, cell free BALF will be analyzed using a BCA Protein Assay (Pierce). Analysis will be completed using the Softmax 4.0 program and data will be graphed using Graph Pad Prism Software.

Histology

Lungs will be harvested from eight animals per treatment group. Half of each lung will be fixed with 10% formaldehyde neutral buffer solution for 24 hours, dehydrated in a graded ethanol series, embedded in paraffin, and sliced at 5 μm. Paraffin sections will be stained with hematoxylin-eosin (HE) and Masson for histopathologic analysis. The remaining lung half will be snap frozen and processed for human cell detection (see below).

Human Cell Detection

Total RNA will be isolated from all snap-frozen lung tissue by Asuragen, Inc., according to the company's standard operating procedures. The purity and quantity of total RNA samples will be determined by absorbance readings at 260 and 280 nm using a NanoDrop ND-1000 UV spectrophotometer. RNA integrity will be evaluated using an Agilent Bioanalyzer.

Human-specific assays for GAPDH mRNA (Hs99999905_m1_GAPDH) will be used to estimate the number of hUTC within mouse lung tissue. Samples for quantitative RT-PCR (qRT-PCR) analysis using single-tube TaqMan® Assays (Applied Biosystems) will be processed by Asuragen, Inc., according to the company's standard operating procedures. Dilutions of total RNA will be reverse transcribed using the TagMan® High Capacity cDNA Synthesis Kit (Applied Biosystems) according to the manufacturer's instructions and in a total reaction volume of 20 microliters per dilution. 50 ng input cDNA will then be analyzed by PCR. All amplifications will be performed in triplicate on a validated ABI 7500 real-time thermocycler. Following incubation at 95° C. for 10 minutes, samples will be amplified in 40 cycles of 95° C. for 15 seconds, then 60° C. for 1 minute.

Example 4

Pulmonary Protective Efficacy in a Rodent Model of Elastase Induced Emphysema

This study will demonstrate the efficacy of intravenously administered hUTC in treating, ameliorating and/or preventing elastase-induced emphysema in a rodent model.

C57BL/6N mice or rats will be anesthetized with ether or intraperitoneal injection of ketamine (90 mg/kg) and xylazine (1 mg/kg) and given intranasal administration of 0.3 or 1.2 units of porcine pancreatic elastase (Sigma-Aldrich, St. Louis, Mo., U.S.A). Control mice will receive intranasal administration of saline alone.

Two to twenty-four hours after elastase treatment, increasing concentrations of human umbilical tissue derived cells (hUTC) will be administered via tail vein injection. As described in Table 4.1, $0.1 \times 10^6$, $1 \times 10^6$ or $3 \times 10^6$ hUTC, reconstituted in PBS vehicle, will be administered in a total volume of 200 ul. PBS vehicle, without hUTC will be administered in a similar fashion as in the hUTC treatment groups. Two weeks after vehicle or hUTC injections, the animals will be sacrificed to harvest lung tissue samples and bronchoalveolar lavage fluid (BALF), which will be stored at −70° C. prior to analyses.

TABLE 4.1

Experimental design.

| Treatment group | Treatment |
|---|---|
| 1 | PBS |
| 2 | $0.1e^6$ hUTC |
| 3 | $1e^6$ hUTC |
| 4 | $3e^6$ hUTC |

BALF Analysis

To prepare BALF, all animals will be euthanized and lungs will be lavaged once with 1.0 mL sterile PBS (Invitrogen) and the tubes will be placed on wet ice. The BALF will be centrifuged at 1000 rpm for 5 min and the supernatant fluid will be removed and used for further analysis.

Cytokine/chemokine levels in both BALF and lung homogenate supernatant will be determined using a mouse 22-multiplex bead kit (Millipore) following the manufacturer's protocol and analyzed using the BioRad Bioplex machine. The results will be graphed and analyzed using GraphPad Prism Software.

BALF Total Protein Analysis

To determine the total protein in each sample, cell free BALF will be analyzed using a BCA Protein Assay (Pierce). Analysis will be completed using the Softmax 4.0 program and data will be graphed using Graph Pad Prism Software.

Histology

Lung tissue samples will be fixed with 10% formaldehyde neutral buffer solution for 24 hours, dehydrated in a graded ethanol series, embedded in paraffin, and sliced at 5 μm. Paraffin sections will be stained with hematoxolin-eosin (H&E) and Masson for histopathology analysis.

Human Cell Detection

Total RNA will be isolated from mouse tissues by Asuragen, Inc., according to the company's standard operating procedures. The purity and quantity of total RNA samples will be determined by absorbance readings at 260 and 280 nm using a NanoDrop ND-1000 UV spectrophotometer. RNA integrity will be evaluated using an Agilent Bioanalyzer.

Human-specific assays for GAPDH mRNA (Hs99999905_m1_GAPDH) will be used to estimate the number of hUTC within mouse lung tissue. Samples for quantitative RT-PCR (qRT-PCR) analysis using single-tube TaqMan® Assays (Applied Biosystems) will be processed by Asuragen, Inc., according to the company's standard operating procedures. Dilutions of total RNA will be reverse transcribed using the TaqMan® High Capacity cDNA Synthesis Kit (Applied Biosystems) according to the manufacturer's instructions and in a total reaction volume of 20 microliters per dilution. 50 ng input cDNA will then be analyzed by PCR. All amplifications will be performed in triplicate on a validated ABI 7500 real-time thermocycler. Following incubation at 95° C. for 10 minutes, samples will be amplified in 40 cycles of 95° C. for 15 seconds, then 60° C. for 1 minute. Total number of hUTC within the mouse lungs will be estimated based on a standard curve generated by analyzing known amounts of purified hUTC total RNA.

BALF Total Protein

A statistically significant decrease in BALF total protein concentration will be observed in hUTC treated animals compared to vehicle control treated animals. In addition, in is possible that significant neutrophil accumulation will be observed in PBS control animals but may be reduced in hUTC treatment groups.

BALF Cytokine/Extracellular Matrix Protein Analysis

A statistically significant decrease in profibrotic and/or proinflammatory cytokines will be observed in hUTC treated animals compared to vehicle control treated animals. In addition, elastase will increase the content of ECM in bronchoalveolar lavage fluid, a marker for lung injury. These effects will be attenuated by hUTC treatment.

Histological Analysis

Elastase treatment will result in the development of subpleural areas of inflammation that encompass a significant portion of the lung parenchyma. In addition, loss of normal alveolar and bronchi architecture as well as vasculature will be observed. Administration of hUTC soon after challenge with elastase will reduce the extent of inflammation and damage within the lung as evidenced by large areas of undamaged tissue with normal alveolar architecture.

Human Cell Engraftment

Human cells will be detected within the lungs of hUTC treated rodents but absent from PBS vehicle treated animals.

Example 5

Isolation of Cells

Umbilical cell isolation. Umbilical cords were obtained from National Disease Research Interchange (NDRI, Philadelphia, Pa.). The tissues were obtained following normal deliveries. The cell isolation protocols were performed aseptically in a laminar flow hood. To remove blood and debris, the cord was washed in phosphate buffered saline (PBS; Invitrogen, Carlsbad, Calif.) in the presence of penicillin at 100 Units/milliliter, streptomycin at 100 milligrams/milliliter and amphotericin B at 0.25 micrograms/milliliter (Invitrogen Carlsbad, Calif.). The tissues were then mechanically dissociated in 150 cm$^2$ tissue culture plates in the presence of 50 milliliters of medium (DMEM-low glucose or DMEM-high glucose; Invitrogen) until the tissue was minced into a fine pulp. The chopped tissues were transferred to 50 milliliter conical tubes (approximately 5 grams of tissue per tube).

The tissue was then digested in either DMEM-low glucose medium or DMEM-high glucose medium, each containing penicillin at 100 Units/milliliter, streptomycin at 100 milligrams/milliliter, amphotericin B at 0.25 micrograms/milliliter and the digestion enzymes. In some experiments an enzyme mixture of collagenase and dispase was used ("C:D") (collagenase (Sigma, St Louis, Mo.), 500 Units/milliliter; and dispase (Invitrogen), 50 Units/milliliter, in DMEM-Low glucose medium). In other experiments a mixture of collagenase, dispase and hyaluronidase ("C:D:H") was used (C:D:H=collagenase, 500 Units/milliliter; dispase, 50 Units/milliliter; and hyaluronidase (Sigma), 5 Units/milliliter, in DMEM-Low glucose). The conical tubes containing the tissue, medium and digestion enzymes were incubated at 37° C. in an orbital shaker (Environ, Brooklyn, N.Y.) at 225 rpm for 2 hrs.

After digestion, the tissues were centrifuged at 150×g for 5 minutes, the supernatant was aspirated. The pellet was resuspended in 20 milliliters of growth medium (DMEM: Low glucose (Invitrogen), 15 percent (v/v) fetal bovine serum (FBS; defined fetal bovine serum; Lot #AND18475; Hyclone, Logan, Utah), 0.001% (v/v) 2-mercaptoethanol (Sigma), penicillin at 100 Units per milliliter, streptomycin at 100 micrograms per milliliter, and amphotericin B at 0.25 micrograms per milliliter (each from Invitrogen, Carlsbad, Calif.)). The cell suspension was filtered through a 70-micron nylon BD FALCON Cell Strainer (BD Biosciences, San Jose, Calif.). An additional 5 milliliters rinse comprising growth medium was passed through the strainer. The cell suspension was then passed through a 40-micrometer nylon cell strainer (BD Biosciences, San Jose, Calif.) and chased with a rinse of an additional 5 milliliters of growth medium.

The filtrate was resuspended in growth medium (total volume 50 milliliters) and centrifuged at 150×g for 5 minutes. The supernatant was aspirated and the cells were resuspended in 50 milliliters of fresh growth medium. This process was repeated twice more.

After the final centrifugation, supernatant was aspirated and the cell pellet was resuspended in 5 milliliters of fresh growth medium. The number of viable cells was determined using trypan blue staining Cells were then cultured under standard conditions.

The cells isolated from umbilical cord tissues were seeded at 5,000 cells/cm$^2$ onto gelatin-coated T-75 flasks (Corning Inc., Corning, N.Y.) in growth medium. After two days, spent medium and unadhered cells were aspirated from the flasks. Adherent cells were washed with PBS three times to remove debris and blood-derived cells. Cells were then replenished with growth medium and allowed to grow to confluence (about 10 days from passage 0 to passage 1). On subsequent passages (from passage 1 to 2 etc), cells reached sub-confluence (75-85 percent confluence) in 4-5 days. For these subsequent passages, cells were seeded at 5,000 cells/cm$^2$. Cells were grown in a humidified incubator with 5 percent carbon dioxide at 37° C.

In some experiments, cells were isolated from postpartum tissues in DMEM-low glucose medium after digestion with LIBERASE (2.5 milligrams per milliliter, Blendzyme 3; Roche Applied Sciences, Indianapolis, Ind.) and hyaluronidase (5 Units/milliliter, Sigma). Digestion of the tissue and isolation of the cells was as described for other protease digestions above, however, the LIBERASE/hyaluronidase mixture was used instead of the C:D or C:D:H enzyme mixture. Tissue digestion with LIBERASE resulted in the isolation of cell populations from postpartum tissues that expanded readily.

Procedures were compared for isolating cells from the umbilical cord using differing enzyme combinations. Enzymes compared for digestion included: i) collagenase; ii) dispase; iii) hyaluronidase; iv) collagenase:dispase mixture (C:D); v) collagenase:hyaluronidase mixture (C:H); vi) dispase:hyaluronidase mixture (D:H); and vii) collagenase:dispase:hyaluronidase mixture (C:D:H). Differences in cell isolation utilizing these different enzyme digestion conditions were observed (Table 5-1).

Other attempts were made to isolate pools of cells from umbilical cord by different approaches. In one instance, umbilical cord was sliced and washed with growth medium to dislodge the blood clots and gelatinous material. The mixture of blood, gelatinous material and growth medium was collected and centrifuged at 150×g. The pellet was resuspended and seeded onto gelatin coated flasks in growth medium. From these experiments a cell population was isolated that readily expanded.

Cells have also been isolated from cord blood samples obtained from NDRI. The isolation protocol used was that of International Patent Application PCT/US2002/029971 by Ho et al. Samples (50 milliliter and 10.5 milliliters, respectively) of umbilical cord blood (NDRI, Philadelphia Pa.) were mixed with lysis buffer (filter-sterilized 155 millimolar ammonium chloride, 10 millimolar potassium bicarbonate, 0.1 millimolar EDTA buffered to pH 7.2 (all components from Sigma, St. Louis, Mo.)). Cells were lysed at a ratio of 1:20 cord blood to lysis buffer. The resulting cell suspension was vortexed for 5 seconds, and incubated for 2 minutes at ambient temperature. The lysate was centrifuged (10 minutes at 200×g). The cell pellet was resuspended in Complete Minimal Essential Medium (Gibco, Carlsbad Calif.) containing 10 percent fetal bovine serum (Hyclone, Logan Utah), 4 millimolar glutamine (Mediatech Herndon, Va.), penicillin at 100 Units per milliliter and streptomycin at 100 micrograms per milliliter (Gibco, Carlsbad, Calif.). The resuspended cells were centrifuged (10 minutes at 200×g), the supernatant was aspirated, and the cell pellet was washed in complete medium. Cells were seeded directly into either T75 flasks (Corning, N.Y.), T75 laminin-coated flasks, or T175 fibronectin-coated flasks (both Becton Dickinson, Bedford, Mass.).

To determine whether cell populations could be isolated under different conditions and expanded under a variety of conditions immediately after isolation, cells were digested in growth medium with or without 0.001 percent (v/v) 2-mercaptoethanol (Sigma, St. Louis, Mo.), using the enzyme combination of C:D:H, according to the procedures provided above. All cells were grown in the presence of penicillin at 100 Units per milliliter and streptomycin at 100 micrograms per milliliter. Under all tested conditions cells attached and expanded well between passage 0 and 1 (Table 5-2). Cells in conditions 5-8 and 13-16 were demonstrated to proliferate well up to 4 passages after seeding, at which point they were cryopreserved.

The combination of C:D:H, provided the best cell yield following isolation, and generated cells that expanded for many more generations in culture than the other conditions (Table 5-1). An expandable cell population was not attained using collagenase or hyaluronidase alone. No attempt was made to determine if this result is specific to the collagenase that was tested.

TABLE 5-1

Isolation of cells from umbilical cord tissue using varying enzyme combinations

| Enzyme Digest | Cells Isolated | Cell Expansion |
|---|---|---|
| Collagenase | X | X |
| Dispase | + (>10 h) | + |
| Hyaluronidase | X | X |
| Collagenase:Dispase | ++ (<3 h) | ++ |
| Collagenase:Hyaluronidase | ++ (<3 h) | + |
| Dispase:Hyaluronidase | + (>10 h) | + |
| Collagenase:Dispase:Hyaluronidase | +++ (<3 h) | +++ |

Key:
+ = good,
++ = very good,
+++ = excellent,
X = no success

Cells attached and expanded well between passage 0 and 1 under all conditions tested for enzyme digestion and growth (Table 5-2). Cells in experimental conditions 5-8 and 13-16 proliferated well up to 4 passages after seeding, at which point they were cryopreserved. All cells were cryopreserved for further analysis.

TABLE 5-2

Isolation and culture expansion of postpartum cells under varying conditions:

| Condition | Medium | 15% FBS | BME | Gelatin | 20% $O_2$ | Growth Factors |
|---|---|---|---|---|---|---|
| 1 | DMEM-Lg | Y | Y | Y | Y | N |
| 2 | DMEM-Lg | Y | Y | Y | N (5%) | N |
| 3 | DMEM-Lg | Y | Y | N | Y | N |
| 4 | DMEM-Lg | Y | Y | N | N (5%) | N |
| 5 | DMEM-Lg | N (2%) | Y | N (Laminin) | Y | EGF/FGF (20 ng/ml) |
| 6 | DMEM-Lg | N (2%) | Y | N (Laminin) | N (5%) | EGF/FGF (20 ng/ml) |
| 7 | DMEM-Lg | N (2%) | Y | N (Fibronectin) | Y | PDGF/VEGF |
| 8 | DMEM-Lg | N (2%) | Y | N (Fibronectin) | N (5%) | PDGF/VEGF |
| 9 | DMEM-Lg | Y | N | Y | Y | N |
| 10 | DMEM-Lg | Y | N | Y | N (5%) | N |
| 11 | DMEM-Lg | Y | N | N | Y | N |
| 12 | DMEM-Lg | Y | N | N | N (5%) | N |
| 13 | DMEM-Lg | N (2%) | N | N (Laminin) | Y | EGF/FGF (20 ng/ml) |
| 14 | DMEM-Lg | N (2%) | N | N (Laminin) | N (5%) | EGF/FGF (20 ng/ml) |
| 15 | DMEM-Lg | N (2%) | N | N (Fibronectin) | Y | PDGF/VEGF |
| 16 | DMEM-Lg | N (2%) | N | N (Fibronectin) | N (5%) | PDGF/VEGF |

Nucleated cells attached and grew rapidly. These cells were analyzed by flow cytometry and were similar to cells obtained by enzyme digestion.

The preparations contained red blood cells and platelets. No nucleated cells attached and divided during the first 3 weeks. The medium was changed 3 weeks after seeding and no cells were observed to attach and grow.

Populations of cells could be isolated from umbilical tissue efficiently using the enzyme combination collagenase (a metalloprotease), dispase (neutral protease) and hyaluronidase (mucolytic enzyme which breaks down hyaluronic acid). LIBERASE, which is a blend of collagenase and a neutral protease, may also be used. Blendzyme 3, which is collagenase (4 Wunsch units/gram) and thermolysin (1714 casein Units/gram), was also used together with hyaluronidase to isolate cells. These cells expanded readily over many passages when cultured in growth expansion medium on gelatin coated plastic.

Cells were also isolated from residual blood in the cords, but not cord blood. The presence of cells in blood clots washed from the tissue, which adhere and grow under the conditions used, may be due to cells being released during the dissection process.

Example 6

Growth Characteristics of Cells

The cell expansion potential of umbilicus-derived cells was compared to other populations of isolated stem cells. The process of cell expansion to senescence is referred to as Hayflick's limit. (Hayflick, L, *J. Am. Geriatr. Soc.,* 1974; 22(1):1-12; Hayflick, L, *Gerontologist,* 1974; 14(1):37-45).

Tissue culture plastic flasks were coated by adding 20 milliliters 2% (w/v) gelatin (Type B: 225 Bloom; Sigma, St Louis, Mo.) to a T75 flask (Corning Inc., Corning, N.Y.) for 20 minutes at room temperature. After removing the gelatin solution, 10 milliliters of phosphate-buffered saline (PBS) (Invitrogen, Carlsbad, Calif.) was added and then aspirated.

For comparison of growth expansion potential the following cell populations were utilized; i) mesenchymal stem cells (MSC; Cambrex, Walkersville, Md.); ii) adipose-derived cells (U.S. Pat. No. 6,555,374 B1; U.S. Patent Application US20040058412); iii) normal dermal skin fibroblasts (cc-2509 lot #9F0844; Cambrex, Walkersville, Md.); and iv) umbilicus-derived cells. Cells were initially seeded at 5,000 cells/cm² on gelatin-coated T75 flasks in growth medium. For subsequent passages, cell cultures were treated as follows. After trypsinization, viable cells were counted after trypan blue staining Cell suspension (50 microliters) was combined with trypan blue (50 microliters, Sigma, St. Louis Mo.). Viable cell numbers were estimated using a hemocytometer.

Following counting, cells were seeded at 5,000 cells/cm² onto gelatin-coated T 75 flasks in 25 milliliters of fresh growth medium. Cells were grown in a standard atmosphere (5 percent carbon dioxide (v/v)) at 37° C. The growth medium was changed twice per week. When cells reached about 85 percent confluence they were passaged; this process was repeated until the cells reached senescence.

At each passage, cells were trypsinized and counted. The viable cell yield, population doublings [ln (cells final/cells initial)/ln2], and doubling time (time in culture/population doubling) were calculated. For the purposes of determining optimal cell expansion, the total cell yield per passage was determined by multiplying the total yield for the previous passage by the expansion factor for each passage (i.e., expansion factor=cells final/cells initial).

The expansion potential of cells banked at passage 10 was also tested. A different set of conditions was used. Normal dermal skin fibroblasts (cc-2509 lot #9F0844; Cambrex, Walkersville, Md.) and umbilicus-derived cells were tested. These cell populations had been banked at passage 10 previously, having been cultured at 5,000 cells/cm² at each passage to that point. The effect of cell density on the cell populations following cell thaw at passage 10 was determined. Cells were thawed under standard conditions and counted using trypan blue staining Thawed cells were then seeded at 1,000 cells/cm² in growth medium. Cells were grown under standard atmospheric conditions at 37° C. The growth medium was changed twice a week. Cells were passaged as they reached about 85% confluence. The cells were subsequently passaged until senescence, i.e., until they could not be expanded any further. Cells were trypsinized and counted at each passage. The cell yield, population doubling (ln (cells final/cells initial)/ln2) and doubling time (time in culture)/population doubling) were calculated. The total cell yield per passage was determined by multiplying total yield for the previous passage by the expansion factor for each passage (i.e., expansion factor=cells final/cells initial).

The expansion potential of freshly isolated umbilicus-derived cell cultures under low cell seeding conditions was tested in another experiment. Umbilicus-derived cells were isolated as described in a previous example. The cells were seeded at 1,000 cells/cm² and passaged as described above until senescence. The cells were grown under standard atmospheric conditions at 37° C. The growth medium was changed twice per week. The cells were passaged as they reached about 85% confluence. At each passage, cells were trypsinized and counted by trypan blue staining. The cell yield, population doubling (ln (cell final/cell initial)/ln 2) and doubling time (time in culture/population doubling) were calculated for each passage. The total cell yield per passage was determined by multiplying the total yield for the previous passage by the expansion factor for each passage (i.e., expansion factor=cell final/cell initial). The cells were grown on gelatin and non-gelatin coated flasks.

It has been demonstrated that low $O_2$ cell culture conditions can improve cell expansion in certain circumstances. (See, e.g., US20040005704). In order to determine if cell expansion of umbilicus-derived cells could be improved by altering cell culture conditions, cultures of umbilicus-derived cells were grown in low oxygen conditions. The cells were seeded at 5,000 cells/cm² in growth medium on gelatin coated flasks. The cells were initially cultured under standard atmospheric conditions through passage 5, at which point they were transferred to low oxygen (5% $O_2$) culture conditions.

In other experiments cells were expanded on non-coated, collagen-coated, fibronectin-coated, laminin-coated and matrigel-coated plates. Cultures have been demonstrated to expand well on these different matrices.

Umbilicus-derived cells expanded for more than 40 passages generating cell yields of >1E17 cells in 60 days. In contrast, MSCs and fibroblasts senesced after <25 days and <60 days, respectively. Although both adipose-derived and omental cells expanded for almost 60 days, they generated total cell yields of 4.5E12 and 4.24E13 respectively. Thus, when seeded at 5,000 cells/cm² under the experimental conditions utilized, umbilicus-derived cells expanded much better than the other cell types grown under the same conditions (Table 6-1).

TABLE 6-1

Growth characteristics for different cell populations grown to senescence

| Cell Type | Senescence | Total Population Doublings | Yield (Total Cells) |
|---|---|---|---|
| MSC | 24 d | 8 | 4.72E7 |
| Adipose-derived cell | 57 d | 24 | 4.5E12 |
| Fibroblasts | 53 d | 26 | 2.82E13 |
| Umbilical | 65 d | 42 | 6.15E17 |

Umbilicus-derived and fibroblast cells expanded for greater than 10 passages generating cell yields of >1E11 cells in 60 days (Table 6-2). Under these conditions both the fibroblasts and the umbilicus-derived cell populations senesced after 80 days, completing >50 and >40 population doublings respectively.

TABLE 6-2

Growth characteristics for different cell populations using low density growth expansion from passage 10 through senescence

| Cell Type (Passage No.) | Senescence | Total Population Doublings | Yield (Total Cells) |
|---|---|---|---|
| Fibroblast (P10) | 80 days | 43.68 | 2.59E11 |
| Umbilical (P10) | 80 days | 53.6 | 1.25E14 |

Cells expanded well under the reduced oxygen conditions, however, culturing under low oxygen conditions does not appear to have a significant effect on cell expansion for postpartum-derived cells. These results are preliminary in the sense that any ultimate conclusions to be made regarding the effect of reduced oxygen would best be drawn from experiments on growing cells in low oxygen from initial isolation. Standard atmospheric conditions have already proven successful for growing sufficient numbers of cells, and low oxygen culture is not required for the growth of postpartum-derived cells.

The current cell expansion conditions of growing isolated umbilicus-derived cells at densities of about 5,000 cells/cm², in growth medium on gelatin-coated or uncoated flasks, under standard atmospheric oxygen, are sufficient to generate large numbers of cells at passage 11. Furthermore, the data suggests that the cells can be readily expanded using lower density culture conditions (e.g. 1,000 cells/cm²). Umbilicus-derived cell expansion in low oxygen conditions also facilitates cell expansion, although no incremental improvement in cell expansion potential has yet been observed when utilizing these conditions for growth. Presently, culturing umbilicus-derived cells under standard atmospheric conditions is preferred for generating large pools of cells. However, when the culture conditions are altered, umbilicus-derived cell expansion can likewise be altered. This strategy may be used to enhance the proliferative and differentiative capacity of these cell populations.

Under the conditions utilized, while the expansion potential of MSC and adipose-derived cells is limited, umbilicus-derived cells expand readily to large numbers.

Example 7

Growth of Cells in Medium Containing D-Valine

It has been reported that medium containing D-valine instead of the normal L-valine isoform can be used to selectively inhibit the growth of fibroblast-like cells in culture. (Hongpaisan, J, *Cell Biol Int.*, 2000; 24:1-7; Sordillo, L M, et al., *Cell Biol Int Rep.*, 1988; 12:355-64). Experiments were performed to determine whether umbilicus-derived cells could grow in medium containing D-valine.

Umbilicus-derived cells (P5) and fibroblasts (P9) were seeded at 5,000 cells/cm$^2$ in gelatin-coated T75 flasks (Corning, Corning, N.Y.). After 24 hours the medium was removed and the cells were washed with phosphate buffered saline (PBS) (Gibco, Carlsbad, Calif.) to remove residual medium. The medium was replaced with a modified growth medium (DMEM with D-valine (special order Gibco), 15% (v/v) dialyzed fetal bovine serum (Hyclone, Logan, Utah), 0.001% (v/v) betamercaptoethanol (Sigma), penicillin at 50 Units/milliliter and streptomycin at 50 milligrams/milliliter (Gibco)).

Umbilicus-derived cells and fibroblast cells seeded in the D-valine-containing medium did not proliferate, unlike cells seeded in growth medium containing dialyzed serum. Fibroblasts cells changed morphologically, increasing in size and changing shape. All of the cells died and eventually detached from the flask surface after four weeks. Thus, it may be concluded that umbilical cord tissue-derived cells require L-valine for cell growth and to maintain long-term viability. L-valine is preferably not removed from the growth medium for umbilical cord tissue-derived cells.

Example 8

Karyotype Analysis of Cells

Cell lines used in cell therapy are preferably homogeneous and free from any contaminating cell type. Human cells used in cell therapy should have a normal number (46) of chromosomes with normal structure. To identify umbilicus-derived cell lines that are homogeneous and free from cells of non-umbilical tissue origin, karyotypes of cell samples were analyzed.

UTC from postpartum tissue of a male neonate were cultured in growth media. Postpartum tissue from a male neonate (X,Y) was selected to allow distinction between neonatal-derived cells and maternal derived cells (X,X). Cells were seeded at 5,000 cells per square centimeter in growth medium in a T25 flask (Corning, Corning, N.Y.) and expanded to 80% confluence. A T25 flask containing cells was filled to the neck with growth media. Samples were delivered to a clinical cytogenetics lab by courier (estimated lab to lab transport time is one hour). Chromosome analysis was performed by the Center for Human & Molecular Genetics at the New Jersey Medical School, Newark, N.J. Cells were analyzed during metaphase when the chromosomes are best visualized. Of twenty cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

All cell samples sent for chromosome analysis were interpreted by the cytogenetics laboratory staff as exhibiting a normal appearance. Three of the sixteen cell lines analyzed exhibited a heterogeneous phenotype (XX and XY) indicating the presence of cells derived from both neonatal and maternal origins (Table 8-1). Each of the cell samples was characterized as homogeneous. (Table 8-1).

TABLE 8-1

Karyotype results of UTC.

| Tissue | Passage | Metaphase cells counted | Metaphase cells analyzed | Number of karyotypes | ISCN Karyotype |
|---|---|---|---|---|---|
| Umbilical | 23 | 20 | 5 | 2 | 46, XX |
| Umbilical | 6 | 20 | 5 | 2 | 46, XY |
| Umbilical | 3 | 20 | 5 | 2 | 46, XX |

Chromosome analysis identified umbilicus-derived UTC whose karyotypes appear normal as interpreted by a clinical cytogenetic laboratory. Karyotype analysis also identified cell lines free from maternal cells, as determined by homogeneous karyotype.

Example 9

Flow Cytometric Evaluation of Cell Surface Markers

Characterization of cell surface proteins or "markers" by flow cytometry can be used to determine a cell line's identity. The consistency of expression can be determined from multiple donors, and in cells exposed to different processing and culturing conditions. Postpartum cell lines isolated from the umbilicus were characterized by flow cytometry, providing a profile for the identification of these cell lines.

Cells were cultured in growth medium, in plasma-treated T75, T150, and T225 tissue culture flasks (Corning, Corning, N.Y.) until confluent. The growth surfaces of the flasks were coated with gelatin by incubating 2% (w/v) gelatin (Sigma, St. Louis, Mo.) for 20 minutes at room temperature.

Adherent cells in flasks were washed in phosphate buffered saline (PBS); (Gibco, Carlsbad, Mo.) and detached with trypsin/EDTA (Gibco). Cells were harvested, centrifuged, and resuspended in 3% (v/v) FBS in PBS at a cell concentration of $1 \times 10^7$ per milliliter. In accordance with the manufacture's specifications, antibody to the cell surface marker of interest (see below) was added to 100 microliters of cell suspension and the mixture was incubated in the dark for 30 minutes at 4° C. After incubation, cells were washed with PBS and centrifuged to remove unbound antibody. Cells were resuspended in 500 microliters PBS and analyzed by flow cytometry. Flow cytometry analysis was performed with a FACS calibur instrument (Becton Dickinson, San Jose, Calif.).

The following antibodies to cell surface markers were used.

TABLE 9-1

Antibodies used in characterizing cell surface markers of UDCs.

| Antibody | Manufacture | Catalog Number |
| --- | --- | --- |
| CD10 | BD Pharmingen (San Diego, CA) | 555375 |
| CD13 | BD Pharmingen | 555394 |
| CD31 | BD Pharmingen | 555446 |
| CD34 | BD Pharmingen | 555821 |
| CD44 | BD Pharmingen | 555478 |
| CD45RA | BD Pharmingen | 555489 |
| CD73 | BD Pharmingen | 550257 |
| CD90 | BD Pharmingen | 555596 |
| CD117 | BD Pharmingen | 340529 |
| CD141 | BD Pharmingen | 559781 |
| PDGFr-alpha | BD Pharmingen | 556002 |
| HLA-A, B, C | BD Pharmingen | 555553 |
| HLA-DR, DP, DQ | BD Pharmingen | 555558 |
| IgG-FITC | Sigma (St. Louis, MO) | F-6522 |
| IgG-PE | Sigma | P-4685 |

Umbilicus-derived cells were analyzed at passages 8, 15, and 20.

To compare differences among donors, umbilical cord tissue-derived cells from different donors were compared to each other.

Umbilicus-derived cells cultured on gelatin-coated flasks were also compared to umbilicus-derived cells cultured on uncoated flasks.

Four treatments used for isolation and preparation of cells were compared. Cells derived from postpartum tissue by treatment with: 1) collagenase; 2) collagenase/dispase; 3) collagenase/hyaluronidase; and 4) collagenase/hyaluronidase/dispase were compared.

Umbilical cord-derived cells at passage 8, 15, and 20 analyzed by flow cytometry all expressed CD10, CD13, CD44, CD73, CD 90, PDGFr-alpha and HLA-A, B, C, indicated by increased fluorescence relative to the IgG control. These cells were negative for CD31, CD34, CD45, CD117, CD141, and HLA-DR, DP, DQ, indicated by fluorescence values consistent with the IgG control.

Umbilical cord-derived cells isolated from separate donors analyzed by flow cytometry each showed positive for the production of CD10, CD13, CD44, CD73, CD 90, PDGFr-alpha and HLA-A, B, C, reflected in the increased values of fluorescence relative to the IgG control. These cells were negative for the production of CD31, CD34, CD45, CD117, CD141, and HLA-DR, DP, DQ with fluorescence values consistent with the IgG control.

The umbilical cord-derived cells expanded on gelatin-coated and uncoated flasks analyzed by flow cytometry were all positive for the production of CD10, CD13, CD44, CD73, CD 90, PDGFr-alpha and HLA-A, B, C, with increased values of fluorescence relative to the IgG control. These cells were negative for the production of CD31, CD34, CD45, CD117, CD141, and HLA-DR, DP, DQ, with fluorescence values consistent with the IgG control.

Analysis of umbilical cord-derived cells by flow cytometry has established an identity of these cell lines. These umbilical cord-derived cells are positive for CD10, CD13, CD44, CD73, CD90, PDGFr-alpha, and HLA-A,B,C; and negative for CD31, CD34, CD45, CD117, CD141 and HLA-DR, DP, DQ. This identity was consistent between variations in variables including the donor, passage, culture vessel surface coating, digestion enzymes, and placental layer. Some variation in individual fluorescence value histogram curve means and ranges were observed, but all positive curves under all conditions tested were normal and expressed fluorescence values greater than the IgG control, thus confirming that the cells comprise a homogeneous population which has positive expression of the markers.

Example 10

Analysis of Cells by Oligonucleotide Array

Oligonucleotide arrays were used to compare gene expression profiles of umbilicus-derived and placenta-derived cells with fibroblasts, human mesenchymal stem cells, and another cell line derived from human bone marrow. This analysis provided a characterization of the postpartum-derived cells and identified unique molecular markers for these cells.

Postpartum Tissue-Derived Cells.

Human umbilical cords and placenta were obtained from National Disease Research Interchange (NDRI, Philadelphia, Pa.) from normal full term deliveries with patient consent. The tissues were received and cells were isolated as described in Example 5 after digestion with a C:D:H mixture. The cells were cultured in growth medium on gelatin-coated plastic tissue culture flasks. The cultures were incubated at 37° C. with 5% $CO_2$.

Fibroblasts.

Human dermal fibroblasts were purchased from Cambrex Incorporated (Walkersville, Md.; Lot number 9F0844) and ATCC CRL-1501 (CCD39SK). Both lines were cultured in DMEM/F12 medium (Invitrogen, Carlsbad, Calif.) with 10% (v/v) fetal bovine serum (Hyclone) and penicillin/streptomycin (Invitrogen)). The cells were grown on standard tissue-treated plastic.

Human Mesenchymal Stem Cells (hMSC).

hMSCs were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human Iliac Crest Bone Marrow Cells (ICBM).

Human iliac crest bone marrow was received from NDRI with patient consent. The marrow was processed according to the method outlined by Ho, et al. (WO03/025149). The marrow was mixed with lysis buffer (155 mM $NH_4Cl$, 10 mM $KHCO_3$, and 0.1 mM EDTA, pH 7.2) at a ratio of 1 part bone marrow to 20 parts lysis buffer. The cell suspension was vortexed, incubated for 2 minutes at ambient temperature, and centrifuged for 10 minutes at 500×g. The supernatant was discarded and the cell pellet was resuspended in Minimal Essential Medium-alpha (Invitrogen) supplemented with 10% (v/v) fetal bovine serum and 4 mM glutamine. The cells were centrifuged again and the cell pellet was resuspended in fresh medium. The viable mononuclear cells were counted using trypan blue exclusion (Sigma, St. Louis, Mo.). The mononuclear cells were seeded in plastic tissue culture flasks at $5 \times 10^4$ cells/cm$^2$. The cells were incubated at 37° C. with 5% $CO_2$ at either standard atmospheric $O_2$ or at 5% $O_2$. Cells were cultured for 5 days without a media change. Media and non-adherent cells were removed after 5 days of culturing. The adherent cells were maintained in culture.

Actively growing cultures of cells were removed from the flasks with a cell scraper in cold phosphate buffered saline (PBS). The cells were centrifuged for 5 minutes at 300×g. The supernatant was removed and the cells were resuspended in fresh PBS and centrifuged again. The supernatant was removed and the cell pellet was immediately frozen and stored at −80° C. Cellular mRNA was extracted and transcribed into cDNA. The cDNA was then transcribed into cRNA and biotin-labeled. The biotin-labeled cRNA was hybridized with Affymetrix GENECHIP HG-U133A oligonucleotide arrays (Affymetrix, Santa Clara, Calif.). The hybridizations and data collection were performed according to the manufacturer's specifications. Data analysis was performed using "Significance Analysis of Microarrays" (SAM) version 1.21 computer software (Tusher, V. G. et al., 2001, *Proc. Natl. Acad. Sci. USA* 98: 5116-5121). Licenses for the analysis software are available through the Office of Technology Licensing, Stanford University, and more information is available on the World Wide Web at Professor Tibshirani's web site in the Dep't of Statistics, Stanford University (www-stat.stanford.edu/~tibs/SAM/).

Fourteen different populations of cells were analyzed in this study. The cells, along with passage information, culture substrate, and culture media are listed in Table 10-1.

TABLE 10-1

Cells analyzed by the microarray study. The cells lines are listed by their identification code along with passage at the time of analysis, cell growth substrate, and growth media.

| Cell Population | Passage | Substrate | Media |
|---|---|---|---|
| Umbilical (022803) | 2 | Gelatin | DMEM, 15% FBS, 2-BME |
| Umbilical (042103) | 3 | Gelatin | DMEM, 15% FBS, 2-BME |
| Umbilical (071003) | 4 | Gelatin | DMEM, 15% FBS, 2-BME |
| Placenta (042203) | 12 | Gelatin | DMEM, 15% FBS, 2-BME |
| Placenta (042903) | 4 | Gelatin | DMEM, 15% FBS, 2-BME |
| Placenta (071003) | 3 | Gelatin | DMEM, 15% FBS, 2-BME |
| ICBM (070203) (5% $O_2$) | 3 | Plastic | MEM 10% FBS |
| ICBM (062703) (std $O_2$) | 5 | Plastic | MEM 10% FBS |
| ICBM (062703) (5% $O_2$) | 5 | Plastic | MEM 10% FBS |
| hMSC (Lot 2F1655) | 3 | Plastic | MSCGM |
| hMSC (Lot 2F1656) | 3 | Plastic | MSCGM |
| hMSC (Lot 2F1657) | 3 | Plastic | MSCGM |
| hFibroblast (9F0844) | 9 | Plastic | DMEM-F12, 10% FBS |
| hFibroblast (CCD39SK) | 4 | Plastic | DMEM-F12, 10% FBS |

The data were evaluated by principle component analysis with SAM software as described above. The analysis revealed 290 genes that were expressed in different relative amounts in the cells tested. This analysis provided relative comparisons between the populations.

Table 10-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes.

TABLE 10-2

The Euclidean Distances for the Cell Pairs. The Euclidean distance was calculated for the cell types using the 290 genes that were expressed differentially between the cell types. Similarity between the cells is inversely proportional to the Euclidean distance.

| CELL PAIR | Euclidean Distance |
|---|---|
| ICBM-HMSC | 24.71 |
| PLACENTA-UMBILICAL | 25.52 |
| ICBM-FIBROBLAST | 36.44 |
| ICBM-PLACENTA | 37.09 |
| FIBROBLAST-MSC | 39.63 |
| ICBM-UMBILICAL | 40.15 |
| Fibroblast-Umbilical | 41.59 |
| MSC-PLACENTA | 42.84 |
| MSC-UMBILICAL | 46.86 |
| ICBM-PLACENTA | 48.41 |

Tables 10-3, 10-4, and 10-5 show the expression of genes increased in placenta-derived cells (Table 10-3), increased in umbilical cord-derived cells (Table 10-4), and reduced in umbilical cord and placenta-derived cells (Table 10-5).

TABLE 10-3

Genes which are specifically increased in expression in the placenta-derived cells as compared to the other cell lines assayed.
Genes Increased in Placenta-Derived Cells

| Probe Set ID | Gene Name | NCBI Accession Number |
|---|---|---|
| 209732_at | C-type (calcium dependent, carbohydrate-recognition domain) lectin, superfamily member 2 (activation-induced) | AF070642 |
| 206067_s_at | Wilms tumor 1 | NM_024426 |
| 207016_s_at | aldehyde dehydrogenase 1 family, member A2 | AB015228 |
| 206367_at | Renin | NM_000537 |
| 210004_at | oxidized low density lipoprotein (lectin-like) receptor 1 | AF035776 |
| 214993_at | *Homo sapiens*, clone IMAGE: 4179671, mRNA, partial cds | AF070642 |
| 202178_at | protein kinase C, zeta | NM_002744 |
| 209780_at | hypothetical protein DKFZp564F013 | AL136883 |
| 204135_at | downregulated in ovarian cancer 1 | NM_014890 |
| 213542_at | *Homo sapiens* mRNA; cDNA DKFZp547K1113 (from clone DKFZp547K1113) | AI246730 |

TABLE 10-4

Genes which are specifically increased in expression in umbilical cord-
derived cells as compared to the other cell lines assayed.
Genes Increased in Umbilicus-Derived Cells

| Probe Set ID | Gene Name | NCBI Accession Number |
| --- | --- | --- |
| 202859_x_at | Interleukin 8 | NM_000584 |
| 211506_s_at | Interleukin 8 | AF043337 |
| 210222_s_at | reticulon 1 | BC000314 |
| 204470_at | chemokine (C-X-C motif) ligand 1 (melanoma growth stimulating activity | NM_001511 |
| 206336_at | chemokine (C-X-C motif) ligand 6 (granulocyte chemotactic protein 2) | NM_002993 |
| 207850_at | Chemokine (C-X-C motif) ligand 3 | NM_002090 |
| 203485_at | reticulon 1 | NM_021136 |
| 202644_s_at | tumor necrosis factor, alpha-induced protein 3 | NM_006290 |

TABLE 10-5

Genes which were decreased in expression in the umbilical cord and
placenta cells as compared to the other cell lines assayed.
Genes Decreased in Umbilicus- and Placenta-Derived Cells

| Probe Set ID | Gene name | NCBI Accession Number |
| --- | --- | --- |
| 210135_s_at | short stature homeobox 2 | AF022654.1 |
| 205824_at | heat shock 27 kDa protein 2 | NM_001541.1 |
| 209687_at | chemokine (C-X-C motif) ligand 12 (stromal cell-derived factor 1) | U19495.1 |
| 203666_at | chemokine (C-X-C motif) ligand 12 (stromal cell-derived factor 1) | NM_000609.1 |
| 212670_at | elastin (supravalvular aortic stenosis, Williams-Beuren syndrome) | AA479278 |
| 213381_at | *Homo sapiens* mRNA; cDNA DKFZp586M2022 (from clone DKFZp586M2022) | N91149 |
| 206201_s_at | mesenchyme homeobox 2 (growth arrest-specific homeobox) | NM_005924.1 |
| 205817_at | Sine oculis homeobox homolog 1 (*Drosophila*) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |
| 205200_at | Tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | Interleukin 11 receptor, alpha | NM_004512.1 |
| 202465_at | Procollagen C-endopeptidase enhancer | NM_002593.2 |
| 203706_s_at | Frizzled homolog 7 (*Drosophila*) | NM_003507.1 |
| 212736_at | hypothetical gene BC008967 | BE299456 |
| 214587_at | Collagen, type VIII, alpha 1 | BE877796 |
| 201645_at | Tenascin C (hexabrachion) | NM_002160.1 |
| 210239_at | iroquois homeobox protein 5 | U90304.1 |
| 203903_s_at | Hephaestin | NM_014799.1 |
| 205816_at | integrin, beta 8 | NM_002214.1 |
| 203069_at | synaptic vesicle glycoprotein 2 | NM_014849.1 |
| 213909_at | *Homo sapiens* cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | Sine oculis homeobox homolog 2 (*Drosophila*) | NM_016932.1 |
| 213435_at | KIAA1034 protein | AB028957.1 |
| 206115_at | early growth response 3 | NM_004430.1 |
| 213707_s_at | distal-less homeobox 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | Biglycan | AA845258 |
| 201261_x_at | Biglycan | BC002416.1 |
| 202132_at | transcriptional co-activator with PDZ-binding motif (TAZ) | AA081084 |
| 214701_s_at | fibronectin 1 | AJ276395.1 |
| 213791_at | Proenkephalin | NM_006211.1 |
| 205422_s_at | Integrin, beta-like 1 (with EGF-like repeat domains) | NM_004791.1 |
| 214927_at | *Homo sapiens* mRNA full length insert cDNA clone EUROIMAGE 1968422 | AL359052.1 |

TABLE 10-5-continued

Genes which were decreased in expression in the umbilical cord and placenta cells as compared to the other cell lines assayed.
Genes Decreased in Umbilicus- and Placenta-Derived Cells

| Probe Set ID | Gene name | NCBI Accession Number |
|---|---|---|
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | Homo sapiens mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | Insulin-like growth factor binding protein 2, 36 kDa | NM_000597.1 |

Tables 10-6, 10-7, and 10-8 show the expression of genes increased in human fibroblasts (Table 10-6), ICBM cells (Table 10-7), and MSCs (Table 10-8).

TABLE 10-6

Genes which were increased in expression in fibroblasts as compared to the other cell lines assayed.
Genes increased in fibroblasts dual specificity phosphatase 2
KIAA0527 protein
Homo sapiens cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
Homo sapiens cDNA: FLJ23564 fis, clone LNG10773
Homo sapiens mRNA; cDNA DKFZp564A072 (from clone DKFZp564A072)
LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [Homo sapiens]
transforming growth factor, beta 2
hypothetical protein MGC29643
antigen identified by monoclonal antibody MRC OX-2
putative X-linked retinopathy protein

TABLE 10-7

Genes which were increased in expression in the ICBM-derived cells as compared to the other cell lines assayed.
Genes Increased In ICBM Cells cardiac ankyrin repeat protein
MHC class I region ORF
integrin, alpha 10
hypothetical protein FLJ22362
UDP-N-acetyl-alpha-D-galactosamine:polypeptide N-acetylgalactosaminyltransferase 3 (GalNAc-T3)
interferon-induced protein 44
SRY (sex determining region Y)-box 9 (campomelic dysplasia, autosomal sex-reversal)
keratin associated protein 1-1

TABLE 10-7-continued

Genes which were increased in expression in the ICBM-derived cells as compared to the other cell lines assayed.
Genes Increased In ICBM Cells hippocalcin-like 1
jagged 1 (Alagille syndrome)
proteoglycan 1, secretory granule

TABLE 10-8

Genes which were increased in expression in the MSC cells as compared to the other cell lines assayed.
Genes Increased In MSC Cells interleukin 26
maltase-glucoamylase (alpha-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1
Homo sapiens cDNA FLJ12232 fis, clone MAMMA1001206
Homo sapiens cDNA FLJ34668 fis, clone LIVER2000775
jun B proto-oncogene
B-cell CLL/lymphoma 6 (zinc finger protein 51)
zinc finger protein 36, C3H type, homolog (mouse)

The present example was performed to provide a molecular characterization of the cells derived from umbilical cord and placenta. This analysis included cells derived from three different umbilical cords and three different placentas. The study also included two different lines of dermal fibroblasts, three lines of mesenchymal stem cells, and three lines of iliac crest bone marrow cells. The mRNA that was expressed by these cells was analyzed on a GENECHIP oligonucleotide array that contained oligonucleotide probes for 22,000 genes.

The analysis revealed that transcripts for 290 genes were present in different amounts in these five different cell types. These genes include ten genes that are specifically increased in the placenta-derived cells and seven genes specifically increased in the umbilical cord-derived cells. Fifty-four genes were found to have specifically lower expression levels in placenta-derived and umbilical cord tissue-derived cells.

The expression of selected genes has been confirmed by PCR, as shown in Example 11. Postpartum-derived cells generally, and umbilical derived cells, in particular, have distinct gene expression profiles, for example, as compared to other human cells, such as the bone marrow-derived cells and fibroblasts tested here.

Example 11

Cell Markers

Gene expression profiles of cells derived from human umbilical cord were compared with those of cells derived from other sources using an Affymetrix GENECHIP. Six "signature" genes were identified: oxidized LDL receptor 1, interleukin-8 (IL-8), renin, reticulon, chemokine receptor ligand 3 (CXC ligand 3), and granulocyte chemotactic protein 2 (GCP-2). These "signature" genes were expressed at relatively high levels in umbilicus-derived cells.

The procedures described in this example were conducted to verify the microarray data and compare data for gene and protein expression, as well as to establish a series of reliable assays for detection of unique identifiers for umbilicus-derived cells.

Umbilicus-derived cells (four isolates), and normal human dermal fibroblasts (NHDF; neonatal and adult) were grown in growth medium in gelatin-coated T75 flasks. Mesenchymal stem cells (MSCs) were grown in mesenchymal stem cell growth Medium Bullet kit (MSCGM; Cambrex, Walkerville, Md.).

For IL-8 experiments, cells were thawed from liquid nitrogen and plated in gelatin-coated flasks at 5,000 cells/$cm^2$, grown for 48 hours in growth medium and then grown further for 8 hours in 10 milliliters of serum starvation medium [DMEM—low glucose (Gibco, Carlsbad, Calif.), penicillin (50 Units/milliliter), streptomycin (50 micrograms/milliliter)(Gibco) and 0.1% (w/v) Bovine Serum Albumin (BSA; Sigma, St. Louis, Mo.)]. RNA was then extracted and the supernatants were centrifuged at 150×g for 5 minutes to remove cellular debris. Supernatants were frozen at −80° C. until ELISA analysis.

Umbilical cord tissue-derived cells, as well as human fibroblasts derived from human neonatal foreskin, were cultured in growth medium in gelatin-coated T75 flasks. The cells were frozen at passage 11 in liquid nitrogen. The cells were thawed and transferred to 15 milliliter centrifuge tubes. After centrifugation at 150×g for 5 minutes, the supernatant was discarded. Cells were resuspended in 4 milliliters culture medium and counted. The cells were grown in a 75 $cm^2$ flask containing 15 milliliters of growth medium at 375,000 cell/flask for 24 hours. The medium was changed to a serum starvation medium for 8 hours. The serum starvation medium was collected at the end of incubation, centrifuged at 14,000×g for 5 minutes and stored at −20° C.

To estimate the number of cells in each flask, 2 milliliters of trypsin/EDTA (Gibco, Carlsbad, Calif.) were added to each flask. After cells detached from the flask, trypsin activity was neutralized with 8 milliliters of growth medium. The cells were transferred to a 15 milliliter centrifuge tube and centrifuged at 150×g for 5 minutes. The supernatant was removed and 1 milliliter growth medium was added to each tube to resuspend the cells. The cell number was determined with a hemocytometer.

The amount of IL-8 secreted by the cells into the serum starvation medium was analyzed using ELISA assays (R&D Systems, Minneapolis, Minn.). All assays were conducted according to the instructions provided by the manufacturer.

RNA was extracted from confluent umbilical cord-derived cells and fibroblasts, or for IL-8 expression, from cells treated as described above. Cells were lysed with 350 microliters buffer RLT containing beta-mercaptoethanol (Sigma, St. Louis, Mo.) according to the manufacturer's instructions (RNeasy Mini Kit; Qiagen, Valencia, Calif.). RNA was extracted according to the manufacturer's instructions (RNeasy Mini Kit; Qiagen, Valencia, Calif.) and subjected to DNase treatment (2.7 Units/sample) (Sigma St. Louis, Mo.). RNA was eluted with 50 microliters DEPC-treated water and stored at −80° C. RNA was also extracted from human umbilical cord. Tissue (30 milligrams) was suspended in 700 microliters of buffer RLT containing beta-mercaptoethanol. Samples were mechanically homogenized and the RNA extraction proceeded according to manufacturer's specification. RNA was extracted with 50 microliters of DEPC-treated water and stored at −80° C.

RNA was reverse-transcribed using random hexamers with the TaqMan reverse transcription reagents (Applied Biosystems, Foster City, Calif.) at 25° C. for 10 minutes, 37° C. for 60 minutes, and 95° C. for 10 minutes. Samples were stored at −20° C.

Genes identified by cDNA microarray as uniquely regulated in umbilical cord cells (signature genes—including oxidized LDL receptor, interleukin-8, renin, and reticulon), were further investigated using real-time and conventional PCR.

PCR was performed on cDNA samples using gene expression products sold under the tradename Assays-on-Demand (Applied Biosystems) gene expression products. Oxidized LDL receptor (Hs00234028); renin (Hs00166915); reticulon (Hs00382515); CXC ligand 3 (Hs00171061); GCP-2 (Hs00605742); IL-8 (Hs00174103); and GAPDH were mixed with cDNA and TaqMan Universal PCR master mix according to the manufacturer's instructions (Applied Biosystems) using a 7000 sequence detection system with ABI Prism 7000 SDS software (Applied Biosystems). Thermal cycle conditions were initially 50° C. for 2 minutes and 95° C. for 10 minutes, followed by 40 cycles of 95° C. for 15 seconds and 60° C. for 1 minute. PCR data were analyzed according to manufacturer's specifications (User Bulletin #2 from Applied Biosystems for ABI Prism 7700 Sequence Detection System).

Conventional PCR was performed using an ABI PRISM 7700 (Perkin Elmer Applied Biosystems, Boston, Mass.) to confirm the results from real-time PCR. PCR was performed using 2 microliters of cDNA solution (1× Taq polymerase (tradename AMPLITAQ GOLD) universal mix PCR reaction buffer (Applied Biosystems) and initial denaturation at 94° C. for 5 minutes. Amplification was optimized for each primer set. For IL-8, CXC ligand 3, and reticulon (94° C. for 15 seconds, 55° C. for 15 seconds and 72° C. for 30 seconds for 30 cycles); for renin (94° C. for 15 seconds, 53° C. for 15 seconds and 72° C. for 30 seconds for 38 cycles); for oxidized LDL receptor and GAPDH (94° C. for 15 seconds, 55° C. for 15 seconds and 72° C. for 30 seconds for 33 cycles). Primers used for amplification are listed in Table 11-1. Primer concentration in the final PCR reaction was 1 micromolar except for GAPDH which was 0.5 micromolar. GAPDH primers were the same as for real-time PCR, except that the manufacturer's TaqMan probe was not added to the final PCR reaction. Samples were separated on 2% (w/v) agarose gel and stained with ethidium bromide (Sigma, St. Louis, Mo.). Images were captured on 667 film (Universal Twinpack, VWR International, South Plainfield, N.J.) using a fixed focal-length POLAROID camera (VWR International, South Plainfield, N.J.).

TABLE 11-1

Primers used

| a. Primer name | Primers |
|---|---|
| Oxidized LDL receptor | S: 5'-GAGAAATCCAAAGAGCAAATGG-3' (SEQ ID NO: 1)<br>A: 5'-AGAATGGAAAACTGGAATAGG-3' (SEQ ID NO: 2) |
| Renin | S: 5'-TCTTCGATGCTTCGGATTCC-3' (SEQ ID NO: 3)<br>A: 5'-GAATTCTCGGAATCTCTGTTG-3' (SEQ ID NO: 4) |
| Reticulon | S: 5'-TTACAAGCAGTGCAGAAAACC-3' (SEQ ID NO: 5)<br>A: 5'-AGTAAACATTGAAACCACAGCC-3' (SEQ ID NO: 6) |
| Interleukin-8 | S: 5'-TCTGCAGCTCTGTGTGAAGG-3' (SEQ ID NO: 7)<br>A: 5'-CTTCAAAAACTTCTCCACAACC-3' (SEQ ID NO: 8) |
| Chemokine (CXC) ligand 3 | S: 5'-CCCACGCCACGCTCTCC-3' (SEQ ID NO: 9)<br>A: 5'-TCCTGTCAGTTGGTGCTCC-3' (SEQ ID NO: 10) |

Umbilical cord-derived cells were fixed with cold 4% (w/v) paraformaldehyde (Sigma-Aldrich, St. Louis, Mo.) for 10 minutes at room temperature. One isolate each of umbilical cord-derived cells at passage 0 (P0) (directly after isolation) and passage 11 (P11) (two isolates of Umbilical cord-derived cells) and fibroblasts (P11) were used. Immunocytochemistry was performed using antibodies directed against the following epitopes: vimentin (1:500, Sigma, St. Louis, Mo.), desmin (1:150; Sigma—raised against rabbit; or 1:300; Chemicon, Temecula, Calif.—raised against mouse), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested on passage 11 umbilical cord-derived cells: anti-human GROalpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGA-A (1:100; Santa Cruz, Biotech).

Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the process. Primary antibodies, diluted in blocking solution, were then applied to the cultures for a period of 1 hour at room temperature. The primary antibody solutions were removed and the cultures were washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150, Santa Cruz Biotech). Cultures were then washed and 10 micromolar DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution (no 1° control). Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and re-suspended 3% (v/v) FBS in PBS at a cell concentration of $1\times10^7$/milliliter. One hundred microliter aliquots were delivered to conical tubes. Cells stained for intracellular antigens were permeabilized with Perm/Wash buffer (BD Pharmingen, San Diego, Calif.). Antibody was added to aliquots as per the manufacturer's specifications, and the cells were incubated for in the dark for 30 minutes at 4° C. After incubation, cells were washed with PBS and centrifuged to remove excess antibody. Cells requiring a secondary antibody were resuspended in 100 microliter of 3% FBS. Secondary antibody was added as per the manufacturer's specification, and the cells were incubated in the dark for 30 minutes at 4° C. After incubation, the cells were washed with PBS and centrifuged to remove excess secondary antibody. The washed cells were resuspended in 0.5 milliliter PBS and analyzed by flow cytometry. The following antibodies were used: oxidized LDL receptor 1 (sc-5813; Santa Cruz, Biotech), GROa (555042; BD Pharmingen, Bedford, Mass.), Mouse IgG1 kappa, (P-4685 and M-5284; Sigma), and Donkey against Goat IgG (sc-3743; Santa Cruz, Biotech.). Flow cytometry analysis was performed with FACScalibur (Becton Dickinson San Jose, Calif.).

Results of real-time PCR for selected "signature" genes performed on cDNA from cells derived from human umbilical cord, adult and neonatal fibroblasts, and Mesenchymal Stem Cells (MSCs) indicate that both reticulon and oxidized LDL receptor expression were higher in umbilicus-derived cells as compared to the other cells. The data obtained from real-time PCR were analyzed by the ΔΔCT method and expressed on a logarithmic scale. No significant differences in the expression levels of CXC ligand 3 and GCP-2 were found between the postpartum cells and controls. The results of real-time PCR were confirmed by conventional PCR. Sequencing of PCR products further validated these observations. No significant difference in the expression level of CXC ligand 3 was found between the postpartum cells and the controls using conventional PCR CXC ligand 3 primers listed in Table 11-1.

The expression of the cytokine, IL-8 in umbilical cord tissue-derived cells was elevated in both growth medium-cultured and serum-starved umbilical cord tissue-derived cells. All real-time PCR data were validated with conventional PCR and by sequencing PCR products.

After growth in serum-free media, the conditioned media were examined for the presence of IL-8. The greatest amounts of IL-8 were detected in media in which umbilical cells had been grown (Table 11-2). No IL-8 was detected in medium in which human dermal fibroblasts had been grown.

TABLE 11-2

IL-8 protein expression measured by ELISA

| Cell type | IL-8 |
|---|---|
| Human fibroblasts | ND |
| Placenta Isolate 1 | ND |
| UMBC Isolate 1 | 2058.42 ± 144.67 |
| Placenta Isolate 2 | ND |
| UMBC Isolate 2 | 2368.86 ± 22.73 |
| Placenta Isolate 3 (normal $O_2$) | 17.27 ± 8.63 |
| Placenta Isolate 3 (low $O_2$, W/O BME) | 264.92 ± 9.88 |

Results of the ELISA assay for interleukin-8 (IL-8) performed on placenta-and umbilical cord-derived cells as well as human skin fibroblasts. Values are presented here are picogram/million cells, n = 2, sem.
ND: Not Detected Cells derived from the human umbilical cord at passage 0 were probed for the production of selected proteins by immunocytochemical analysis. Immediately after isolation (passage 0), cells were fixed with 4% paraformaldehyde and exposed to antibodies for six proteins: von Willebrand Factor, CD34, cytokeratin 18, desmin, alpha-smooth muscle actin, and vimentin. Umbilical cord-derived cells were positive for alpha-smooth muscle actin and vimentin, with the staining pattern consistent through passage 11.

The production of GROalpha, GCP-2, oxidized LDL receptor 1 and reticulon (NOGO-A) in umbilical cord-derived cells at passage 11 was investigated by immunocytochemistry. Umbilical cord-derived cells were GCP-2 positive, but GRO alpha production was not detected by this method. Furthermore, cells were NOGO-A positive.

Accordance between gene expression levels measured by microarray and PCR (both real-time and conventional) has been established for four genes: oxidized LDL receptor 1, renin, reticulon, and IL-8. The expression of these genes was differentially regulated at the mRNA level in umbilical cord-derived cells, with IL-8 also differentially regulated at the protein level. Differential expression of GCP-2 and CXC ligand 3 was not confirmed at the mRNA level. Although this result does not support data originally obtained from the microarray experiment, this may be due to a difference in the sensitivity of the methodologies.

Cells derived from the human umbilical cord at passage 0 were probed for the expression of alpha-smooth muscle actin and vimentin, and were positive for both. The staining pattern was preserved through passage 11.

In conclusion, the complete mRNA data at least partially verifies the data obtained from the microarray experiments.

Example 12

Immunohistochemical Characterization of Cellular Phenotypes

The phenotypes of cells found within human umbilical cord tissue were analyzed by immunohistochemistry.

Human umbilical cord tissue was harvested and immersion fixed in 4% (w/v) paraformaldehyde overnight at 4° C. Immunohistochemistry was performed using antibodies directed against the following epitopes (see Table 12-1): vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 microns thick) using a standard cryostat (Leica Microsystems) and mounted onto glass slides for staining.

Immunohistochemistry was performed similar to previous studies. (E.g., Messina et al., Exper. Neurol., 2003; 184: 816-829). Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150; Santa Cruz Biotech). Cultures were washed, and 10 micromolar DAPI (Molecular Probes) was applied for 10 minutes to visualize cell nuclei.

Following immunostaining, fluorescence was visualized using the appropriate fluorescence filter on an Olympus inverted epifluorescent microscope (Olympus, Melville, N.Y.). Positive staining was represented by fluorescence signal above control staining Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

TABLE 12-1

Summary of Primary Antibodies Used

| Antibody | Concentration | Vendor |
|---|---|---|
| Vimentin | 1:500 | Sigma, St. Louis, MO |
| Desmin (rb) | 1:150 | Sigma |
| Desmin (m) | 1:300 | Chemicon, Temecula, CA |
| alpha-smooth muscle actin (SMA) | 1:400 | Sigma |
| Cytokeratin 18 (CK18) | 1:400 | Sigma |
| von Willebrand factor (vWF) | 1:200 | Sigma |
| CD34 III | 1:100 | DakoCytomation, Carpinteria, CA |
| GROalpha-PE | 1:100 | BD, Franklin Lakes, NJ |
| GCP-2 | 1:100 | Santa Cruz Biotech |

TABLE 12-1-continued

Summary of Primary Antibodies Used

| Antibody | Concentration | Vendor |
|---|---|---|
| Ox-LDL R1 | 1:100 | Santa Cruz Biotech |
| NOGO-A | 1:100 | Santa Cruz Biotech |

Vimentin, desmin, SMA, CK18, vWF, and CD34 markers were expressed in a subset of the cells found within umbilical cord (data not shown). In particular, vWF and CD34 expression were restricted to blood vessels contained within the cord. CD34+ cells were on the innermost layer (lumen side). Vimentin expression was found throughout the matrix and blood vessels of the cord. SMA was limited to the matrix and outer walls of the artery and vein, but not contained within the vessels themselves. CK18 and desmin were observed within the vessels only, desmin being restricted to the middle and outer layers.

None of these markers were observed within umbilical cord (data not shown).

Vimentin, desmin, alpha-smooth muscle actin, cytokeratin 18, von Willebrand Factor, and CD 34 are expressed in cells within human umbilical cord. Based on in vitro characterization studies showing that only vimentin and alpha-smooth muscle actin are expressed, the data suggests that the current process of umbilical cord-derived cell isolation harvests a subpopulation of cells or that the cells isolated change expression of markers to express vimentin and alpha-smooth muscle actin.

Example 13

Secretion of Trophic Factors

The secretion of selected trophic factors from umbilicus-derived cells was measured. Factors were selected that have angiogenic activity e.g., hepatocyte growth factor (HGF) (Rosen et al., Ciba Found. Symp., 1997; 212:215-26); monocyte chemotactic protein 1 (MCP-1) (Salcedo et al., Blood, 2000; 96; 34-40); interleukin-8 (IL-8) (Li et al., J. Immunol., 2003; 170:3369-76); keratinocyte growth factor (KGF); basic fibroblast growth factor (bFGF); vascular endothelial growth factor (VEGF) (Hughes et al., Ann. Thorac. Surg. 2004; 77:812-8); tissue inhibitor of matrix metalloproteinase 1 (TIMP1); angiopoietin 2 (ANG2); platelet derived growth factor (PDGFbb); thrombopoietin (TPO); heparin-binding epidermal growth factor (HB-EGF); stromal-derived factor 1alpha (SDF-1alpha), neurotrophic/neuroprotective activity (brain-derived neurotrophic factor (BDNF) (Cheng et al., Dev. Biol., 2003; 258; 319-33); interleukin-6 (IL-6); granulocyte chemotactic protein-2 (GCP-2); transforming growth factor beta2 (TGFbeta2)); or chemokine activity (macrophage inflammatory protein 1alpha (MIP1alpha); macrophage inflammatory protein 1 beta (MIPlbeta); monocyte chemoattractant-1 (MCP-1); Rantes (regulated on activation, normal T cell expressed and secreted); 1309; thymus and activation-regulated chemokine (TARC); Eotaxin; macrophage-derived chemokine (MDC); and (IL-8).

Cells derived from umbilical cord, as well as human fibroblasts derived from human neonatal foreskin, were cultured in growth medium on gelatin-coated T75 flasks. Cells were cryopreserved at passage 11 and stored in liquid nitrogen. After thawing, growth medium was added to the cells, followed by transfer to a 15 milliliter centrifuge tube and centrifugation of the cells at 150×g for 5 minutes. The cell pellet was resuspended in 4 milliliters growth medium, and the cells were counted. Cells were seeded at 5,000 cells/cm$^2$ in T75 flasks each containing 15 milliliters of growth medium, and cultured for 24 hours. The medium was changed to a serum-free medium (DMEM-low glucose (Gibco), 0.1% (w/v) bovine serum albumin (Sigma), penicillin (50 Units/milliliter) and streptomycin (50 micrograms/milliliter, Gibco)) for 8 hours. Conditioned serum-free medium was collected at the end of incubation by centrifugation at 14,000×g for 5 minutes and stored at −20° C.

To estimate the number of cells in each flask, the cells were washed with phosphate-buffered saline (PBS) and detached using 2 milliliters trypsin/EDTA (Gibco). Trypsin activity was inhibited by addition of 8 milliliters growth medium. The cells were centrifuged at 150×g for 5 minutes. The supernatant was removed, and the cells were resuspended in 1 milliliter Growth Medium. The cell number was estimated with a hemocytometer.

Cells were grown at 37° C. in 5% carbon dioxide and atmospheric oxygen. The amount of MCP-1, IL-6, VEGF, SDF-1alpha, GCP-2, IL-8, and TGF-beta2 produced by each cell sample was determined by ELISA (R&D Systems, Minneapolis, Minn.). All assays were performed according to the manufacturer's instructions. Values presented are picograms per milliliter per million cells (n=2, sem).

Chemokines (MIP1alpha, MIP1beta, MCP-1, Rantes, 1309, TARC, Eotaxin, MDC, IL8), BDNF, and angiogenic factors (HGF, KGF, bFGF, VEGF, TIMP1, ANG2, PDGFbb, TPO, HB-EGF were measured using SearchLight Proteome Arrays (Pierce Biotechnology Inc.). The Proteome Arrays are multiplexed sandwich ELISAs for the quantitative measurement of two to sixteen proteins per well. The arrays are produced by spotting a 2×2, 3×3, or 4×4 pattern of four to sixteen different capture antibodies into each well of a 96-well plate. Following a sandwich ELISA procedure, the entire plate is imaged to capture the chemiluminescent signal generated at each spot within each well of the plate. The signal generated at each spot is proportional to the amount of target protein in the original standard or sample.

MCP-1 and IL-6 were secreted by umbilicus-derived PPDCs and dermal fibroblasts (Table 13-1). SDF-1alpha and GCP-2 were secreted by fibroblasts. GCP-2 and IL-8 were secreted by umbilicus-derived PPDCs. TGF-beta2 was not detected from either cell type by ELISA.

TABLE 13-1

| | ELISA Results: Detection of Trophic Factors | | | | | | |
|---|---|---|---|---|---|---|---|
| | MCP-1 | IL-6 | VEGF | SDF-1 | GCP-2 | IL-8 | TGF-beta |
| Fibroblast | 17 ± 1 | 61 ± 3 | 29 ± 2 | 19 ± 1 | 21 ± 1 | ND | ND |
| Umbilical (022803) | 1150 ± 74 | 4234 ± 289 | ND | ND | 160 ± 11 | 2058 ± 145 | ND |
| Umbilical (071003) | 2794 ± 84 | 1356 ± 43 | ND | ND | 2184 ± 98 | 2369 ± 23 | ND |

Key:
ND: Not Detected.,
=/− sem

Searchlight™ Multiplexed ELISA assay. TIMP1, TPO, KGF, HGF, FGF, HBEGF, BDNF, MIP1beta, MCPJ, RANTES, I309, TARC, MDC, and IL-8 were secreted from umbilicus-derived PPDCs (Tables 13-2 and 13-3). No Ang2, VEGF, or PDGFbb were detected.

TABLE 13-2

Searchlight ™ Multiplexed ELISA assay results

| | TIMP1 | ANG2 | PDGFbb | TPO | KGF | HGF | FGF | VEGF | HBEGF | BDNF |
|---|---|---|---|---|---|---|---|---|---|---|
| hFB | 19306.3 | ND | ND | 230.5 | 5.0 | ND | ND | 27.9 | 1.3 | ND |
| U1 | 57718.4 | ND | ND | 1240.0 | 5.8 | 559.3 | 148.7 | ND | 9.3 | 165.7 |
| U3 | 21850.0 | ND | ND | 1134.5 | 9.0 | 195.6 | 30.8 | ND | 5.4 | 388.6 |

Key:
hFB (human fibroblasts),
U1 (umbilicus-derived PPDC (022803)),
U3 (umbilicus-derived PPDC (071003)).
ND: Not Detected.

TABLE 13-3

Searchlight ™ Multiplexed ELISA assay results

| | MIP1a | MIP1b | MCP1 | RANTES | I309 | TARC | Eotaxin | MDC | IL8 |
|---|---|---|---|---|---|---|---|---|---|
| hFB | ND | ND | 39.6 | ND | ND | 0.1 | ND | ND | 204.9 |
| U1 | ND | 8.0 | 1694.2 | ND | 22.4 | 37.6 | ND | 18.9 | 51930.1 |
| U3 | ND | 5.2 | 2018.7 | 41.5 | 11.6 | 21.4 | ND | 4.8 | 10515.9 |

Key:
hFB (human fibroblasts),
U1 (umbilicus-derived PPDC (022803)),
U3 (umbilicus-derived PPDC (071003)).
ND: Not Detected.

Umbilicus-derived cells secreted a number of trophic factors. Some of these trophic factors, such as HGF, bFGF, MCP-1 and IL-8, play important roles in angiogenesis. Other trophic factors, such as BDNF and IL-6, have important roles in neural regeneration or protection.

Example 14

In Vitro Immunology

Umbilical cord cell lines were evaluated in vitro for their immunological characteristics in an effort to predict the immunological response, if any, these cells would elicit upon in vivo transplantation. Postpartum cell lines were assayed by flow cytometry for the expression of HLA-DR, HLA-DP, HLA-DQ, CD80, CD86, and B7-H2. These proteins are expressed by antigen-presenting cells (APC) and are required for the direct stimulation of naive $CD4^+$ T cells (Abbas & Lichtman, Cellular and Molecular Immunology, 5th Ed. (2003) Saunders, Philadelphia, p. 171). The cell lines were also analyzed by flow cytometry for the expression of HLA-G (Abbas & Lichtman, supra); CD178 (Coumans et. al., *Journal of Immunological Methods*, 1999; 224: 185-196); and PD-L2 (Abbas & Lichtman, supra; Brown et. al., *The Journal of Immunology*, 2003; 170: 1257-1266). To predict the extent to which postpartum umbilicus-derived cell lines elicit an immune response in vivo, the cell lines were tested in a one-way mixed lymphocyte reaction (MLR).

Cells were cultured in growth medium in T75 flasks (Corning, Corning, N.Y.) coated with 2% gelatin (Sigma, St. Louis, Mo.) until confluent.

Cells were washed in phosphate buffered saline (PBS) (Gibco, Carlsbad, Calif.) and detached with Trypsin/EDTA (Gibco, Carlsbad, Mo.). Cells were harvested, centrifuged, and resuspended in 3% (v/v) FBS in PBS at a cell concentration of $1 \times 10^7$ per milliliter. Antibody (Table 14-1) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACSCalibur instrument (Becton Dickinson, San Jose, Calif.).

TABLE 14-1

Antibodies

| Antibody | Manufacture | Catalog Number |
|---|---|---|
| HLA-DR,DP,DQ | BD Pharmingen (San Diego, CA) | 555558 |
| CD80 | BD Pharmingen | 557227 |
| CD86 | BD Pharmingen | 555665 |
| B7-H2 | BD Pharmingen | 552502 |
| HLA-G | Abcam (Cambridgeshire, UK) | ab 7904-100 |
| CD178 | Santa Cruz (San Cruz, CA) | sc-19681 |
| PD-L2 | BD Pharmingen | 557846 |
| Mouse IgG2alpha | Sigma (St. Louis, MO) | F-6522 |
| Mouse IgG1kappa | Sigma | P-4685 |

Cryopreserved vials of passage 10 umbilicus-derived PPDCs labeled as cell line "A" were packaged on dry ice and sent to CTBR (Senneville, Quebec) to conduct a mixed lymphocyte reaction using CTBR SOP no. CAC-031. Peripheral blood mononuclear cells (PBMCs) were collected from multiple male and female volunteer donors. Six human volunteer blood donors were screened to identify a single allogeneic donor that exhibited a robust proliferation response in a mixed lymphocyte reaction with the other five blood donors. This donor was selected as the allogeneic positive control donor. The remaining five blood donors were selected as recipients. Stimulator (donor) allogeneic PBMC, autologous PBMC, and postpartum cell lines were treated with mitomycin C. Autologous and mitomycin C-treated stimulator cells were added to responder (recipient) PBMCs and cultured for 4 days. After incubation, [$^3$H]thymidine was added to each sample and cultured for 18 hours. Following harvest of the cells, radiolabeled DNA was extracted, and [$^3$H]-thymidine incorporation was measured using a scintillation counter. Reactions were performed in triplicate using two-cell culture plates with three receivers per plate The stimulation index for the allogeneic donor (SIAD) was calculated as the mean proliferation of the receiver plus mitomycin C-treated allogeneic donor divided by the baseline proliferation of the receiver. The stimulation index of the postpartum cells was calculated as the mean proliferation of the receiver plus mitomycin C-treated postpartum cell line divided by the baseline proliferation of the receiver.

Six human volunteer blood donors were screened to identify a single allogeneic donor that will exhibit a robust proliferation response in a mixed lymphocyte reaction with the other five blood donors. This donor was selected as the allogeneic positive control donor. The remaining five blood donors were selected as recipients. The allogeneic positive control donor and umbilical cord-derived cell lines were mitomycin C-treated and cultured in a mixed lymphocyte reaction with the five individual allogeneic receivers. Reactions were performed in triplicate using two cell culture plates with three receivers per plate (Table 14-2). The average stimulation index ranged from 6.5 (plate 1) to 9 (plate 2) and the allogeneic donor positive controls ranged from 42.75 (plate 1) to 70 (plate 2) (Table 14-3).

TABLE 14-3

Average stimulation index of umbilical cells and an allogeneic donor in a mixed lymphocyte reaction with five individual allogeneic receivers.
Average Stimulation Index

|  | Recipient | Umbilicus |
|---|---|---|
| Plate 1 (receivers 1-4) | 42.75 | 6.5 |
| Plate 2 (receiver 5) | 70 | 9 |

Histograms of umbilical cord-derived cells analyzed by flow cytometry show negative expression of HLA-DR, DP, DQ, CD80, CD86, and B7-H2, as noted by fluorescence value consistent with the IgG control, indicating that umbilical cord-derived cell lines lack the cell surface molecules required to directly stimulate allogeneic PBMCs (e.g., $CD4^+$ T cells).

The umbilical cells analyzed by flow cytometry were positive for expression of PD-L2, as reflected in the increase in fluorescence relative to the IgG control. The cells were negative for expression of CD178 and HLA-G, as noted by fluorescence values consistent with the IgG control.

TABLE 14-2

Mixed Lymphocyte Reaction Data - Cell Line A (Umbilical Cord)
DPM for Proliferation Assay

| Analytical number | Culture System | Replicates | | | Mean | SD | CV |
|---|---|---|---|---|---|---|---|
| | | 1 | 2 | 3 | | | |
| Plate ID: Plate 1 | | | | | | | |
| IM04-2478 | Proliferation baseline of receiver | 1074 | 406 | 391 | 623.7 | 390.07 | 62.5 |
| | Control of autostimulation (Mitomycin C treated autologous cells) | 672 | 510 | 1402 | 861.3 | 475.19 | 55.2 |
| | MLR allogenic donor IM04-2477 (Mitomycin C treated) | 43777 | 48391 | 38231 | 43466.3 | 5087.12 | 11.7 |
| | MLR with cell line (Mitomycin C treated cell type A) | 2914 | 5622 | 6109 | 4881.7 | 1721.36 | 35.3 |
| SI (donor) | | | | | 70 | | |
| SI (cell line) | | | | | 8 | | |
| IM04-2479 | Proliferation baseline of receiver | 530 | 508 | 527 | 521.7 | 11.93 | 2.3 |
| | Control of autostimulation (Mitomycin C treated autologous cells) | 701 | 567 | 1111 | 793.0 | 283.43 | 35.7 |
| | MLR allogenic donor IM04-2477 (Mitomycin C treated) | 25593 | 24732 | 22707 | 24344.0 | 1481.61 | 6.1 |
| | MLR with cell line (Mitomycin C treated cell type A) | 5086 | 3932 | 1497 | 3505.0 | 1832.21 | 52.3 |
| SI (donor) | | | | | 47 | | |
| SI (cell line) | | | | | 7 | | |
| IM04-2480 | Proliferation baseline of receiver | 1192 | 854 | 1330 | 1125.3 | 244.90 | 21.8 |
| | Control of autostimulation (Mitomycin C treated autologous cells) | 2963 | 993 | 2197 | 2051.0 | 993.08 | 48.4 |
| | MLR allogenic donor IM04-2477 (Mitomycin C treated) | 25416 | 29721 | 23757 | 26298.0 | 3078.27 | 11.7 |
| | MLR with cell line (Mitomycin C treated cell type A) | 2596 | 5076 | 3426 | 3699.3 | 1262.39 | 34.1 |
| SI (donor) | | | | | 23 | | |
| SI (cell line) | | | | | 3 | | |
| IM04-2481 | Proliferation baseline of receiver | 695 | 451 | 555 | 567.0 | 122.44 | 21.6 |
| | Control of autostimulation (Mitomycin C treated autologous cells) | 738 | 1252 | 464 | 818.0 | 400.04 | 48.9 |
| | MLR allogenic donor IM04-2477 (Mitomycin C treated) | 13177 | 24885 | 15444 | 17835.3 | 6209.52 | 34.8 |
| | MLR with cell line (Mitomycin C treated cell type A) | 4495 | 3671 | 4674 | 4280.0 | 534.95 | 12.5 |
| SI (donor) | | | | | 31 | | |
| SI (cell line) | | | | | 8 | | |
| Plate ID: Plate 2 | | | | | | | |
| IM04-2482 | Proliferation baseline of receiver | 432 | 533 | 274 | 413.0 | 130.54 | 31.6 |
| | Control of autostimulation (Mitomycin C treated autologous cells) | 1459 | 633 | 598 | 896.7 | 487.31 | 54.3 |
| | MLR allogenic donor IM04-2477 (Mitomycin C treated) | 24286 | 30823 | 31346 | 28818.3 | 3933.82 | 13.7 |
| | MLR with cell line (Mitomycin C treated cell type A) | 2762 | 1502 | 6723 | 3662.3 | 2724.46 | 74.4 |
| SI (donor) | | | | | 70 | | |
| SI (cell line) | | | | | 9 | | |
| IM04-2477 (allogenic donor) Cell line type A | Proliferation baseline of receiver | 312 | 419 | 349 | 360.0 | 54.34 | 15.1 |
| | Control of autostimulation (Mitomycin treated autologous cells) | 567 | 604 | 374 | 515.0 | 123.50 | 24.0 |
| | Proliferation baseline of receiver | 5101 | 3735 | 2973 | 3936.3 | 1078.19 | 27.4 |
| | Control of autostimulation (Mitomycin treated autologous cells) | 1924 | 4570 | 2153 | 2882.3 | 1466.04 | 50.9 |

In the mixed lymphocyte reactions conducted with umbilical cell lines the average stimulation index ranged from 6.5 to 9, while that of the allogeneic positive controls ranged from 42.75 to 70. Umbilical cell lines did not express detectable amounts of the stimulating proteins HLA-DR, HLA-DP, HLA-DQ, CD80, CD86, and B7-H2, as measured by flow cytometry. Umbilical cell lines also did not express the immuno-modulating proteins HLA-G and CD178, but expression of PD-L2 was detected by flow cytometry. Allogeneic donor PBMCs contained antigen-presenting cells expressing HLA-DR, DQ, CD8, CD86, and B7-H2, thereby allowing for the stimulation of allogeneic lymphocytes. The absence on umbilicus-derived cells of antigen-presenting cell surface molecules required for the direct stimulation of naïve CD4$^+$ T cells, as well as the presence of PD-L2, an immunomodulating protein, could account for the low stimulation index exhibited by these cells in a MLR as compared to allogeneic controls.

The present invention is not limited to the embodiments described and exemplified above. The invention is capable of variation and modification within the scope of the appended claims.

Example 15

Assay for Telomerase Activity

Telomerase functions to synthesize telomere repeats that serve to protect the integrity of chromosomes and to prolong the replicative life span of cells (Liu, K, et al., *PNAS*, 1999; 96:5147-5152). Telomerase consists of two components, telomerase RNA template (hTER) and telomerase reverse transcriptase (hTERT). Regulation of telomerase is determined by transcription of hTERT but not hTER. Real-time polymerase chain reaction (PCR) for hTERT mRNA thus is an accepted method for determining telomerase activity of cells.

Cell Isolation

Real-time PCR experiments were performed to determine telomerase production of human umbilical cord tissue-derived cells. Human umbilical cord tissue-derived cells were prepared in accordance with Examples 5-7 and the examples set forth in U.S. application Ser. No. 10/877,012 (the '012 application), which issued as U.S. Pat. No. 7,510,873. Generally, umbilical cords obtained from National Disease Research Interchange (Philadelphia, Pa.) following a normal delivery were washed to remove blood and debris and mechanically dissociated. The tissue was then incubated with digestion enzymes including collagenase, dispase and hyaluronidase in culture medium at 37° C. Human umbilical cord tissue-derived cells were cultured according to the methods set forth in the examples of the '012 application. Mesenchymal stem cells and normal dermal skin fibroblasts (cc-2509 lot #9F0844) were obtained from Cambrex, Walkersville, Md. A pluripotent human testicular embryonal carcinoma (teratoma) cell line nTera-2 cells (NTERA-2 cl.D1) (See, Plaia et al., *Stem Cells*, 2006; 24(3):531-546) was purchased from ATCC (Manassas, Va.) and was cultured according to the methods set forth in the '012 application.

Total RNA Isolation

RNA was extracted from the cells using RNeasy® kit (Qiagen, Valencia, Ca.). RNA was eluted with 50 microliters DEPC-treated water and stored at −80° C. RNA was reverse transcribed using random hexamers with the TaqMan® reverse transcription reagents (Applied Biosystems, Foster City, Calif.) at 25° C. for 10 minutes, 37° C. for 60 minutes and 95° C. for 10 minutes. Samples were stored at −20° C.

Real-Time PCR

PCR was performed on cDNA samples using the Applied Biosystems Assays-On-Demand™ (also known as TaqMan® Gene Expression Assays) according to the manufacturer's specifications (Applied Biosystems). This commercial kit is widely used to assay for telomerase in human cells. Briefly, hTERT (human telomerase gene) (Hs00162669) and human GAPDH (an internal control) were mixed with cDNA and TaqMan® Universal PCR master mix using a 7000 sequence detection system with ABI prism 7000 SDS software (Applied Biosystems). Thermal cycle conditions were initially 50° C. for 2 min and 95° C. for 10 min followed by 40 cycles of 95° C. for 15 sec and 60° C. for 1 min. PCR data was analyzed according to the manufacturer's specifications.

Human umbilical cord tissue-derived cells (ATCC Accession No. PTA-6067), fibroblasts, and mesenchymal stem cells were assayed for hTERT and 18S RNA. As shown in Table 22-1, hTERT, and hence telomerase, was not detected in human umbilical cord tissue-derived cells.

TABLE 22-1

|  | hTERT | 18S RNA |
|---|---|---|
| Umbilical cells (022803) | ND | + |
| Fibroblasts | ND | + |

ND—not detected;
+ signal detected

Human umbilical cord tissue-derived cells (isolate 022803, ATCC Accession No. PTA-6067) and nTera-2 cells were assayed and the results showed no expression of the telomerase in two lots of hUTC while the teratoma cell line revealed high level of expression (Table 22-1).

What is claimed is:

1. A method of reducing vascular leak, edema, or inflammation in a lung of a patient having hyperoxia or acute lung injury comprising systemically administering to the patient an effective amount of umbilical cord tissue-derived cells, wherein the umbilical cord tissue-derived cells are isolated from human umbilical cord tissue substantially free of blood, are capable of self-renewal and expansion in culture, have the potential to differentiate into cells of at least a lung tissue, and do not express CD117, hTERT or telomerase, and
wherein the levels of keratinocyte factor, gamma interferon-inducible cytokine, interleukin 1-alpha and monocyte chemotactic factor-1 are reduced in the lung of the patient having hyperoxia or acute lung injury.

2. The method of claim 1, wherein the cells are induced in vitro to differentiate into a lung tissue.

3. The method of claim 1, wherein the cells are administered with at least one other cell type.

4. The method of claim 3, wherein the other cell type is a lung tissue cell selected from the group consisting of lung progenitor cell, vascular smooth muscle cell, vascular smooth muscle progenitor cell, pericyte, vascular endothelial cell, vascular endothelium progenitor cell, and other multipotent or pluripotent stem cell.

5. The method of claim 1, wherein the cells are administered with at least one other agent.

6. The method of claim 5, wherein the agent is selected from the group consisting of an antithrombogenic agent, an anti-inflammatory agent, an immunosuppressive agent, an immunomodulatory agent, a pro-angiogenic agent, and an antiapoptotic agent.

7. The method of claim 1, wherein the umbilical cord tissue-derived cells are administered by injection, infusion, a device implanted in the patient, or by implantation of a matrix or scaffold containing the cells.

8. The method of claim 1, wherein the cells exert a trophic effect on the lung tissue of the patient.

9. The method of claim 1, wherein the cells exert a trophic effect on the vascular smooth muscle of the patient.

10. The method of claim 9, wherein the trophic effect is proliferation of the vascular smooth muscle cells.

11. The method of claim 1, wherein the cells exert a trophic effect on the vascular endothelium of the patient.

12. The method of claim 11, wherein the trophic effect is proliferation of the vascular endothelial cells.

13. The method of claim 1, wherein the cells induce migration of vascular endothelial cells to the sites of the lung disease, disorder or injury.

14. The method of claim 1, wherein the cells induce migration of vascular endothelium progenitor cells to the sites of the lung disease, disorder or injury.

15. The method of claim 1, wherein the cells induce migration of vascular smooth muscle cells to the sites of the lung disease, disorder or injury.

16. The method of claim 1, wherein the cells induce migration of vascular smooth muscle progenitor cells to the sites of the lung disease, disorder or injury.

17. The method of claim 1, wherein the cells induce migration of pericytes to the sites of the lung disease, disorder or injury.

18. The method of claim 1, wherein the cells further comprise the following characteristics:
increased expression for a gene encoding interleukin 8 or reticulon 1, relative to a human cell that is a fibroblast, a mesenchymal stem cell, or an iliac crest bone marrow cell;

express CD10, CD13, CD44, CD73, CD90, PDGFr-alpha, PD-L2 and HLA-A, B,C; and do not express CD31, CD34, CD45, CD80, CD86, CD141, CD178, B7-H2, HLA-G and HLA-DR,DP,DQ.

19. The method of claim 1, wherein the method reduces edema.

20. The method of claim 1, wherein the method reduces vascular leak.

21. A method of reducing vascular leak, edema, or inflammation in a lung of a patient having hyperoxia or acute lung injury comprising administering umbilical cord tissue-derived cells to the patient, wherein the umbilical cord tissue-derived cells are isolated from human umbilical cord tissue substantially free of blood, are capable of self-renewal and expansion in culture, have the potential to differentiate into cells of at least a lung tissue, and do not express CD117, hTERT or telomerase, wherein the cells exert a trophic effect on the lung tissue of the patient, and wherein the levels of keratinocyte factor, gamma interferon-inducible cytokine, interleukin 1-alpha and monocyte chemotactic factor-1 are reduced in the lung of the patient having hyperoxia or acute lung injury.

22. The method of claim 21, wherein the method reduces vascular leak.

23. The method of claim 21, wherein the method reduces edema.

24. The method of claim 21, wherein the cells further comprise the following characteristics:

increased expression for a gene encoding interleukin 8 or reticulon 1, relative to a human cell that is a fibroblast, a mesenchymal stem cell, or an iliac crest bone marrow cell;

express CD10, CD13, CD44, CD73, CD90, PDGFr-alpha, PD-L2 and HLA-A,B,C; and do not express CD31, CD34, CD45, CD80, CD86, CD141, CD178, B7-H2, HLA-G and HLA-G, DR,DP, DQ.

25. The method of claim 1, wherein the cells are allogeneic.

26. The method of claim 21, wherein the cells are allogeneic.

27. The method of claim 1, wherein the patient has hyperoxia.

28. The method of claim 1, wherein the patient has acute lung injury.

29. The method of claim 21, wherein the patient has hyperoxia.

30. The method of claim 21, wherein the patient has acute lung injury.

31. The method of claim 1, wherein the method reduces inflammation in a lung of the patient having hyperoxia or acute lung injury.

32. The method of claim 21, wherein the method reduces inflammation in a lung of the patient having hyperoxia or acute lung injury.

* * * * *

UNITED STATES PATENT AND TRADEMARK OFFICE
CERTIFICATE OF CORRECTION

PATENT NO. : 10,557,116 B2  
APPLICATION NO. : 12/642774  
DATED : February 11, 2020  
INVENTOR(S) : Colter et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 618 days.

Signed and Sealed this  
Twenty-third Day of November, 2021

Drew Hirshfeld  
*Performing the Functions and Duties of the  
Under Secretary of Commerce for Intellectual Property and  
Director of the United States Patent and Trademark Office*